(12) United States Patent
Johnson et al.

(10) Patent No.: US 6,967,199 B2
(45) Date of Patent: *Nov. 22, 2005

(54) SUBSTITUTED DIAMINE DERIVATIVES USEFUL AS MOTILIN ANTAGONISTS

(75) Inventors: Sigmond G. Johnson, Flemington, NJ (US); Ralph A. Rivero, North Wales, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/291,133

(22) Filed: Nov. 8, 2002

(65) Prior Publication Data

US 2003/0203906 A1 Oct. 30, 2003

Related U.S. Application Data

(62) Division of application No. 09/829,767, filed on Apr. 10, 2001, now Pat. No. 6,511,980.
(60) Provisional application No. 60/202,131, filed on May 5, 2000.

(51) Int. Cl.$^7$ .................. A61K 31/5375; C07D 265/30
(52) U.S. Cl. .................. 514/238.8; 544/162; 544/165; 544/358; 546/184; 546/246; 548/566; 548/567; 514/428
(58) Field of Search .................. 548/566, 567; 514/428, 238.8; 544/162, 165, 358; 546/184, 246

(56) References Cited

U.S. PATENT DOCUMENTS

| 3,625,972 | A | | 12/1971 | Schulenberg | |
|---|---|---|---|---|---|
| 3,960,886 | A | | 6/1976 | Schulenberg | |
| 5,994,368 | A | | 11/1999 | Oku | |
| 6,511,980 | B2 | * | 1/2003 | Johnson et al. | .......... 514/239.2 |

FOREIGN PATENT DOCUMENTS

| EP | 0 585 500 A1 | 3/1994 |
|---|---|---|
| WO | WO 97/19682 A1 | 6/1997 |
| WO | WO 99/01127 A1 | 1/1999 |
| WO | WO 99/09053 A1 | 2/1999 |
| WO | WO 99/21846 A1 | 5/1999 |
| WO | WO 00/17231 A1 | 3/2000 |

OTHER PUBLICATIONS

Peeters, Theo L. "Motilin and the Discovery and Development of Motilinomimetics" Old Herborn University Seminar Monograph; vol. 9, No. 9, 1997, pp. 77–87.

PCT International Search Report—Application No. PCT/US01/11821.

* cited by examiner

*Primary Examiner*—Golam M M Shameem
(74) *Attorney, Agent, or Firm*—Ellen Ciambrone Coletti; Evelyn D. Shen; Jeremy K. McKown

(57) ABSTRACT

The present invention relates to novel substituted diamine derivatives for the formula

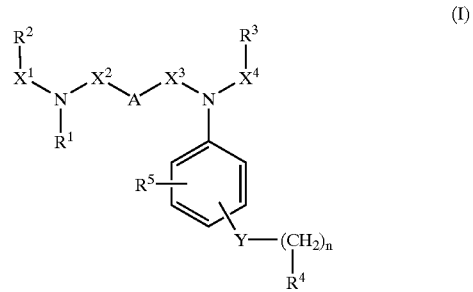

(I)

wherein $R^1$, $R^2$, $R^3$, $R^4$, $X^1$, $X^2$, $X^3$, $X^4$, A, Y and n are as described in the specification, pharmaceutical compositions containing them and intermediates used in their manufacture. More particularly, the compounds of the invention are motilin receptor antagonists useful for the treatment of associated conditions and disorders such as gastrointestinal reflux disorders, eating disorders leading to obesity and irritable bowel syndrome.

17 Claims, No Drawings

SUBSTITUTED DIAMINE DERIVATIVES USEFUL AS MOTILIN ANTAGONISTS

CROSS REFERENCE TO RELATED APPLICATION

This application is a divisional application of U.S. application Ser. No. 09/829,767, filed Apr. 10, 2001, now issued as U.S. Pat. No. 6,511,980, which claims priority from U.S. provisional application Ser. No. 60/202,131, filed May 5, 2000, the contents of which are hereby incorporated by reference.

FIELD OF THE INVENTION

The present invention relates to novel substituted diamine derivatives, pharmaceutical compositions containing them and intermediates used in their manufacture. More particularly, the compounds of the invention are motilin receptor antagonists useful for the treatment of associated conditions and disorders such as gastrointestinal reflux disorders, eating disorders leading to obesity and irritable bowel syndrome.

BACKGROUND OF THE INVENTION

In mammals, the digestion of nutrients and the elimination of waste are controlled by the gastrointestinal system. Within this system, there are a number of natural peptides, ligands, enzymes, and receptors which play a vital role and are potential targets for drug discovery. Modifying the production of, or responses to these endogenous substances can have an effect upon the physiological responses such as diarrhea, nausea, and abdominal cramping. One example of an endogenous substance which affects the gastrointestinal system is motilin.

Motilin is a peptide of 22 amino acids which is produced in the gastrointestinal system of a number of species. Although the sequence of the peptide varies from species to species, there are a great deal of similarities. For example, human motilin and porcine motilin are identical; while motilin isolated from the dog and the rabbit differ by five and four amino acids respectively. Motilin induces smooth muscle contractions in the stomach tissue of dogs, rabbits, and humans as well as in the colon of rabbits. Apart from local gastrointestinal intestinal tissues, motilin and its receptors have been found in other areas. For example motilin has been found in circulating plasma, where a rise in the concentration of motilin has been associated with gastric effects which occur during fasting in dogs and humans. Itoh, Z. et al. *Scand. J. Gastroenterol.* 11:93–110, (1976); Vantrappen, G. et al. *Dig. Dis Sci* 24, 497–500 (1979). In addition, when motilin was intravenously administered to humans it was found to increase gastric emptying and gut hormone release. Christofides, N. D. et al. *Gastroenterology* 76:903–907, 1979.

Aside from motilin itself, there are other substances which are agonists of the motilin receptor and which elicit gastrointestinal emptying. One of those agents is the antibiotic erythromycin. Even though erythromycin is a useful drug, a great number of patients are affected by the drug's gastrointestinal side effects. Studies have shown that erythromycin elicits biological responses that are comparable to motilin itself and therefore may be useful in the treatment of diseases such as chronic idiopathic intestinal pseudo-obstruction and gastroparesis. Weber, F. et al., *The American Journal of Gastroenterology*, 88:4, 485–90 (1993).

Although motilin and erythromycin are agonists of the motilin receptor, there is a need for antagonists of this receptor as well. The nausea, abdominal cramping, and diarrhea which are associated with motilin agonists are unwelcome physiological events. The increased gut motility induced by motilin has been implicated in diseases such as Irritable Bowel Syndrome and esophageal reflux. Therefore researchers have been searching for motilin antagonists.

One such antagonist is OHM-11526. This is a peptide derived from porcine motilin which competes with both motilin and erythromycin for the motilin receptor in a number of species, including rabbits and humans. In addition, this peptide is an antagonist of the contractile smooth muscle response to both erythromycin and motilin in an in vitro rabbit model. Depoortere, I. et al., *European Journal of Pharmacology*, 286, 241–47, (1995). Although this substance is potent in that model ($IC_{50}$ 1.0 nM) it is a peptide and as such offers little hope as an oral drug since it is susceptible to the enzymes of the digestive tract. Zen Itoh, *Motilin*, xvi (1990). Therefore it is desirable to find other non-peptidic agents which act as motilin antagonists. The compounds of this invention are such agents.

The compounds of this invention are non-peptidyl motilin antagonists with potencies and activities comparable to known peptidyl motilin antagonists. These compounds compete with motilin and erythromycin for the motilin receptor site in vitro. In addition, these compounds suppress smooth muscle contractions induced by motilin and erythromycin with activities and potencies comparable to OHM 11526 in an in vitro model.

SUMMARY OF THE INVENTION

The present invention is directed to compounds of the formula (I):

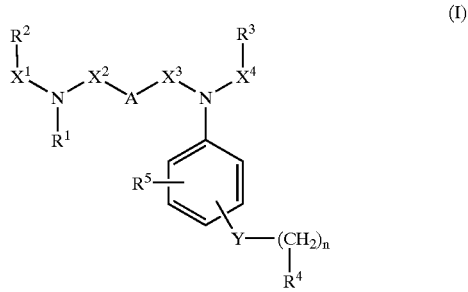

wherein $R^1$ is selected from the group consisting of hydrogen, aryl, aralkyl, heterocyclyl, diarylalkyl, heterocyclyl-alkyl, and lower alkyl; wherein the alkyl, aryl or heterocyclyl moieties in the foregoing groups may be substituted with one or more substituents independently selected from halogen, hydroxy, nitro, carboxy, cyano, amino, dialkylamino, lower alkoxy, lower alkyl, tri-halomethyl, alkylamino, carboxy and alkoxycarbonyl;

$R^2$ is selected from the group consisting of aryl, aralkyl, cycloalkyl, cycloalkyl-alkyl, heterocyclyl, heterocyclyl-alkyl, diarylalkyl, aminoalkyl, tri-halomethyl, arylamino and lower alkyl; wherein the alkyl, aryl, heterocyclyl-alkyl, heterocyclyl, or amino moieties in the foregoing groups may be substituted with one or more substituents independently selected from halogen, hydroxy, nitro, cyano, amino, dialkylamino, lower alkoxy, lower alkyl, tri-halomethyl, alkylamino, phenyl, carboxy, carboxyalkyl and alkoxycarbonyl;

$X^1$, $X^2$, $X^3$ and $X^4$ are independently absent or selected from the group consisting of CO and $SO_2$; provided that at least one of $X^1$ or $X^2$ and at least one of $X^3$ or $X^4$ is CO or $SO_2$;

alternatively $R^1$, $R^2$ and $X^1$ can be taken together (with the amine nitrogen) to form a monocyclic or fused bicyclic or tricyclic secondary amine ring structure; wherein the monocyclic or fused bicyclic or tricyclic secondary amine ring structure may be optionally substituted with one or more substituents independently selected from halogen, oxo, nitro, cyano, amino, alkylamino, dialkylamino, trialkylamino, lower alkoxy, lower alkyl, tri-halomethyl, carboxy, acetyloxy, alkoxycarbonyl, aryl, aralkyl andr heterocyclyl;

A is selected from the group consisting of lower alkyl, lower alkenyl, cycloalkyl, cycloalkyl-alkyl, alkyl-cycloalkyl, cycloalkenyl, cycloalkenyl-alkyl, alkyl-cycloalkenyl, alkyl-cycloalkyl-alkyl; alkyl-aryl-alkyl, alkyl-aryl, aryl-alkyl and phenyl; where, in each case, the A group may optionally be substituted with one or more substituents selected from $R^7$;

where $R^7$ is selected from alkyl, tri-halomethyl, cycloalkyl, aryl, aralkyl, heterocyclyl, heterocyclyl-alkyl, diarylalkyl, aminoalkyl, or arylamino; wherein the alkyl, aryl, heterocyclyl-alkyl, heterocyclyl, or amino moieties in the foregoing groups may be substituted with one or more substituents independently selected from halogen, hydroxy, nitro, cyano, amino, dialkylamino, lower alkoxy, lower alkyl, tri-halomethyl, alkylamino, phenyl, carboxy and alkoxycarbonyl;

provided that A is not -1,3-cyclopentyl-1-ene-alkyl;

$R^3$ is selected from the group consisting of hydrogen, aryl, heterocyclyl, aralkyl, diarylalkyl, heterocyclo-alkyl, tri-halomethyl, alkylamino, arylamino and lower alkyl; wherein the aryl, heterocyclyl, aralkyl, diarylalkyl, heterocyclyl-alkyl, alkylamino, arylamino or lower alkyl group may be substituted with one or more substituents independently selected from halogen, nitro, cyano, amino, dialkylamino, lower alkoxy, lower alkyl, tri-halomethyl, carboxy and alkoxycarbonyl;

Y is selected from the group consisting of —O—, —NH—, —S— and —$SO_2$—;

n is an integer from 0 to 5;

$R^4$ is selected from the group consisting of hydrogen, amino, alkylamino, dialkylamino, N-alkyl-N-aralkyl-amino, trialkylamino, dialkylaminoalkoxyalkyl, heterocyclyl, heterocyclyl-alkyl, oxo-substituted heterocyclyl and lower alkyl-substituted heterocyclyl;

$R^5$ is selected from the group consisting of hydrogen, halogen, nitro, cyano, amino, alkylamino, dialkylamino, trialkylamino, lower alkoxy, lower alkyl, tri-halomethyl, carboxy and alkoxycarbonyl;

and the pharmaceutically acceptable salts, esters and pro-drug forms thereof.

DETAILED DESCRIPTION OF THE INVENTION

Relative to the above generic description, certain compounds of the general formula are preferred.

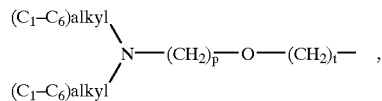

where p and t are integers from 1–6. More preferably, $R^4$ is selected from the group consisting of hydrogen, 4-morpholinyl, 1-pyrrolidinyl, 2-oxo-pyrrolidin-1-yl, 2-(1-methylpyrrolidinyl), 1-piperazinyl, 1-piperidinyl, di(methyl)aminoethyloxyethyl, N-methyl-N-benzyl-amino, di(methyl)amino and diethylamino. More preferably still, $R^4$ is selected from the group consisting of hydrogen, 4-morpholinyl, 1-pyrrolidinyl, 1-piperazinyl, 1-piperidinyl, di(methyl)amino and di(ethyl)amino. More referably still, $R^4$ is selected from the group consisting of hydrogen, 4-morpholinyl, 1-pyrrolidinyl, 1-piperidinyl and di(methyl) amino. Most preferably, $R^4$ is selected from the group consisting of hydrogen, 4-morpholinyl, 1-pyrrolidinyl and 1-piperidinyl;

Preferably $R^5$ is selected from the group consisting of hydrogen and lower alkyl. More preferably $R^5$ is selected from the group consisting of hydrogen and methyl.

In a preferred embodiment of the present invention are those compounds of general formula (I) wherein:

$R^1$ is selected from the group consisting of hydrogen, aralkyl, heterocyclyl and heterocyclyl-alkyl; where the aralkyl, heterocyclyl or heterocyclyl-alkyl may be substituted with one or more substituents independently selected from halogen, lower alkyl, lower alkoxy, tri-halomethyl, hydroxy or nitro;

$R^2$ is selected from the group consisting of alkyl, tri-halomethyl, aryl, aralkyl, arylamino, biphenyl, cycloalkyl, cycloalkyl-alkyl, heterocyclyl and heterocyclyl-alkyl; where the aryl, aralkyl or heterocyclyl group may be substituted with one or more substituents independently selected from halogen, lower alkoxy, nitro, carboxy, carboxyalkyl, hydroxy, phenyl, diphenylmethyl, tri-halomethyl or trihaloalkylacetyl;

$X^1$, $X^2$, $X^3$ and $X^4$ are independently absent or selected from the group consisting of CO and $SO_2$; such that at least one of $X^1$ or $X^2$ and at least one of $X^3$ or $X^4$ is CO or $SO_2$;

A is selected from the group consisting of lower alkyl, alkyl-cycloalkyl, cycloalkyl-alkyl, -cycloalkyl, -cycloalkenyl-, cycloalkenyl-alkyl- and -aryl-alkyl-;

where the alkyl moiety in the foregoing groups may be substituted with one or more substituents independently selected from aralkyl or cycloalkyl;

provided that A is not -1,3-cyclopentyl-1-ene-alkyl;

$R^3$ is selected from the group consisting of hydrogen, aryl, aralkyl and arylamino; where the aryl or aralkyl group may be substituted with one or more substituents independently selected from halogen, lower alkyl, lower alkoxy or tri-halomethyl;

Y is —O—;

n is an integer from 0 to 3;

$R^4$ is selected from the group consisting of hydrogen, heterocyclyl, oxo-substituted heterocyclyl, lower alkyl-substituted heterocyclyl, di(lower alkyl)amino, N-lower alkyl-N-aralkyl-amino and di(lower alkyl)amino alkoxy alkyl;

$R^5$ is selected from the group consisting of hydrogen and lower alkyl;

and the pharmaceutically acceptable salts, esters and pro-drug forms thereof.

In a preferred embodiment are compounds of the general formula (I) wherein:

$R^1$ is selected from the group consisting of hydrogen, phenyl ($C_1$–$C_6$) alkyl-, naphthyl($C_{1-6}$)alkyl and heterocyclyl ($C_1$–$C_6$)alkyl- where the heterocyclyl group is selected from pyridyl and where the phenyl, naphthyl or heterocyclyl moiety is optionally substituted with one to three substituents selected from halogen, lower alkyl, lower alkoxy, tri-halomethyl, hydroxy and nitro;

$R^2$ is selected from the group consisting of ($C_1$–$C_6$) branched or unbranched alkyl, phenyl, phenyl($C_1$–$C_6$)alkyl-, tri-halomethyl, phenylamino-, biphenyl, diphenyl($C_1$–$C_6$) alkyl-, $C_{5-8}$cycloalkyl, $C_{5-8}$cycloalkyl-alkyl, heterocyclyl and heterocyclyl($C_1$–$C_6$)alkyl- wherein the heterocyclyl moiety is selected from naphthyl, furyl, pyridyl, pyrrolidinyl and thienyl and wherein the phenyl or heterocyclyl group may be substituted with one to four substitutuents selected from halogen, lower alkoxy, nitro, carboxy, carboxy($C_{1-4}$) alkyl, hydroxy, phenyl, diphenylmethyl, trihalomethyl and trihaloalkylacetyl;

$X^1$, $X^2$, $X^3$ and $X^4$ are independently absent or selected from the group consisting of CO and $SO_2$; such that at least one of $X^1$ or $X^2$ and at least one of $X^3$ or $X^4$ is CO or $SO_2$;

A is selected from the group consisting of lower alkyl, loweralkyl-cycloalkyl, cycloalkyl-loweralkyl, -cycloalkyl, -cycloalkenyl-, cycloalkenyl-loweralkyl- and -phenyl-loweralkyl- and -benzyl-loweralkyl, provided that A is not -1,3-cyclopentyl-1-ene-alkyl;

$R^3$ is selected from the group consisting of hydrogen, phenyl, benzyl and phenylamino-; where the phenyl or benzyl moieties may be substituted with one to three substituents selected from halogen, lower alkyl, lower alkoxy and trihalomethyl;

Y is —O—;

n is an integer from 0 to 3;

$R^4$ is selected from the group consisting of hydrogen, heterocyclyl, oxo substituted heterocyclyl, lower alkyl-substituted heterocyclyl, di(loweralkyl) amino, N-lower alkyl-N-aralkyl-amino and a moiety of the formula:

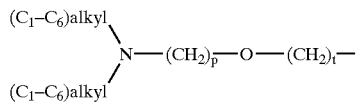

where p and t are integers from 1–6;

$R^5$ is selected from hydrogen and lower alkyl;

and the pharmaceutically acceptable salts esters and pro-drug forms thereof.

In a more preferred embodiment of the present invention are compounds of the general formula (I) wherein $R^1$ is selected from the group consisting of hydrogen, benzyl, 2-(phenyl)ethyl, 4-methylbenzyl, 3-methoxybenzyl, 3-nitrobenzyl, 3-chlorobenzyl, 3-fluorobenzyl, 4-chlorobenzyl, 2,3-dichlorobenzyl, 3,4-dichlorobenzyl, 3,5-dichlorobenzyl, 3,4-difluorobenzyl, 3-trifluoromethylbenzyl, 1-naphthyl-methyl, 2-pyridyl-methyl and 4-(1-hydroxy)pyridyl;

$R^2$ is selected from the group consisting of methyl, ethyl, t-butyl, 2,2-dimethylpropyl, benzyl, 2-(phenyl)ethyl, 3-(phenyl)propyl, 1-(phenyl)propyl, 3-carboxy-n-propyl, 3-carboxy-3-methyl-n-butyl, 2,2-dimethyl-3-carboxy-n-propyl, trichloromethyl, trifluoromethyl, 2-naphthyl, phenylamino, 3-methoxyphenyl, 3-hydroxyphenyl, 4-fluorobenzyl, 3-carboxybenzyl, 3-methoxybenzyl, 4-methoxybenzyl, 3,4-dimethoxybenzyl, 2-(4-methoxyphenyl)ethyl, 4-fluorophenyl, 2-(4-chlorophenyl)ethyl, 3-nitrophenyl, 3,5-di(trifluoromethyl)phenyl, 3,3,3-trifluoropropan-2-oyl, diphenylmethyl, 4-biphenyl, 3-carboxymethyl-1,2,2-trimethyl-cyclopentyl, cyclopentylethyl, (1-carboxymethyl-cyclopentyl)-methyl, 2-furyl, 2-pyridyl-(2-ethyl), 1-pyrrolidinyl-(2-ethyl), 2-theinylmethyl and 2-thienylethyl;

$X^1$, $X^2$, $X^3$ and $X^4$ are independently absent or selected from the group consisting of CO and $SO_2$; such that one of $X^1$ or $X^2$ and one of $X^3$ or $X^4$ is CO or $SO_2$;

A is selected from the group consisting of 1,2-ethyl, 1,3-propyl, 1,4-butyl, 2-methyl-1,3-propyl, 1,1,-dimethyl-(1,3-propyl), 2-cyclopentyl-1,3-n-propyl, 1S,3R-cyclopentyl-methyl, 1,2-cyclopent-1-enyl, 1,4-cyclopentyl-2-ene-methyl, methyl-1,3-cyclohexyl, 1,2-cyclohexyl-methyl-, 1,3-cyclohexyl-methyl-, 1S,3R-cyclohexyl-methyl-, 1R,3S-cyclohexyl-methyl, 1,4-cyclohexyl-methyl-, 1,2-cyclohex-4-enyl, 1,3-phenyl-methyl and 1-benzyl-methyl-;

$R^3$ is selected from the group consisting of hydrogen, phenylamino, 4-methylphenyl, 4-fluorophenyl, 2-fluorobenzyl, 3-fluorobenzyl, 4-fluorobenzyl, 4-chlorobenzyl, 4-methoxybenzyl and 4-trifluoromethylbenzyl;

Y is selected from the group consisting of -3-O— and -4-O—;

n is an integer selected from 0, 2 or 3;

$R^4$ is selected from the group consisting of hydrogen, 4-morpholinyl, 1-pyrrolidinyl, 2-oxo-pyrrolidin-1-yl, 2-(1-methylpyrrolidinyl), 1-piperazinyl, 1-piperidinyl, di(methyl)aminoethyloxyethyl, N-methyl-N-benzyl-amino, di(methyl)amino and diethylamino;

$R^5$ is selected from the group consisting of hydrogen, 2-methyl and 6-methyl;

and the pharmaceutically acceptable salts, esters and pro-drug forms thereof.

In another preferred embodiment of the present invention are compounds of the formula (I) wherein $R^1$, $R^2$ and $X^1$ are taken together (with the amine nitrogen) to form an optionally substituted, monocyclic or fused bicyclic or tricyclic secondary amine ring structure selected from the group consisting of 1-phenyl-1,2,3,4-tetrahydroisoquinolinyl, 4-[(4-chlorophenyl)phenylmethyl]piperazin-1-yl, 2-[1-benzyl-6-methoxy-1,2,3,4-tetrahydro]naphthyl, isoindole-1,3-dione, 5-t-butyl-isoindole-1,3-dione, 5-fluoro-isoindole-1,3-dione, 5-methyl-isoindole-1,3-dione, 5,6-dichloro-isoindole-1,3-dione, 4,7-dichloro-isoindole-1,3-dione, 5-bromo-isoindole-1,3-dione, 5-acetyloxy-isoindole-1,3-dione, benzo[e]isoindole-1,3-dione, 8-fluorobenzo[e] isoindole-1,3-dione, 4,4-dimethyl-piperidine-2,6-dione, 3-aza-bicyclo[3.1.0]hexane-2,6-dione and 8-aza-spiro[4.5] decane-7,9-dione; and the pharmaceutically acceptable salts, esters and pro-drug forms thereof.

In a particularly preferred embodiment $R^1$, $R^2$ and $X^1$ are taken together (with the amine nitrogen) to form 1-phenyl-1,2,3,4-tetrahydroisquinolinyl, $X^2$ is C(O), A is 1,3-propyl, $X^3$ is C(O), $R^3$ is 4-fluorobenzyl, Y is 3-O—, n is 2 and $R^4$ is 4-morpholinyl.

In another preferred embodiment $R^1$, $R^2$ and $X^1$ are taken together (with the amine nitrogen) to form 4-[(4-chlorophenyl)phenylmethyl]piperazin-1-yl, $X^2$ is C(O), A is 1,3-n-propyl, $X^3$ is absent, $R^3$ is 4-fluorophenyl, $X^4$ is C(O), Y is 3-O—, n is 2 and $R^4$ is 4-morpholinyl.

In still another preferred embodiment, $R^1$, $R^2$ and $X^1$ are taken together (with the amine nitrogen) to form 2-[1-benzyl-6-methoxy-1,2,3,4-tetrahydro]-naphthyl, $X^2$ is C(O), A is 1,3-n-propyl, $X^3$ is absent, $R^3$ is 4-fluorophenyl, $X^4$ is C(O), Y is 3-O—, n is 2 and $R^4$ is 4-morpholinyl.

In a class of the invention are compounds of the formula (I) wherein $R^1$ is selected from the group consisting of benzyl, 2-(phenyl)ethyl, 3-nitrobenzyl, 3-chlorobenzyl, 3,4-dichlorobenzyl, 3,4-difluorobenzyl, 3,5-dichlorobenzyl, 3-trifluoromethylbenzyl and 2-pyridyl-methyl;

$R^2$ is selected from the group consisting of t-butyl, 2-(phenyl)ethyl, trichloromethyl, 3-carboxybenzyl, 3-methoxybenzyl, 2-(4-methoxyphenyl)ethyl, 2-(4-chlorophenyl)ethyl, diphenylmethyl, 2-(2-pyridyl)ethyl, 2-(1-pyrrolidinyl)ethyl and 2-(2-thienyl)ethyl;

$X^1$, $X^2$, $X^3$ and $X^4$ are independently absent or CO; such that one of $X^1$ or $X^2$ and one of $X^3$ or $X^4$ is CO;

A is selected from the group consisting of 1,2-ethyl, 1,3-propyl, 2-methyl-1,3-propyl, 1,1,-dimethyl-(1,3- propyl), 2-cyclopentyl-1,3-n-propyl, 1S,3R-cyclopentyl-methyl, 1,3-cyclohexyl-methyl, 1S,3R-cyclohexyl-methyl- and 1R,3S-cyclohexyl-methyl-;

$R^3$ is selected from the group consisting of phenylamino, 4-fluorophenyl, 3-fluorobenzyl, 2-fluorobenzyl, 4-fluorobenzyl, 4-chlorobenzyl, 4-methoxybenzyl and 4-trifluoromethylbenzyl;

Y is selected from the group consisting of -3-O— and -4-O—;

n is an integer selected from 2 or 3;

$R^4$ is selected from the group consisting of hydrogen, 4-morpholinyl, 1-pyrrolidinyl, 1-piperazinyl, 1-piperidinyl, di(methyl)amino and di(ethyl)amino;

$R^5$ is selected from the group consisting of hydrogen, 2-methyl and 6-methyl;

and the pharmaceutically acceptable salts, esters and pro-drug forms thereof.

In another class of the invention are compounds of the formula (I) wherein $R^1$ is selected from the group consisting of benzyl, 2-(phenyl)ethyl, 3-nitrobenzyl, 3-chlorobenzyl, 3,4-dichlorobenzyl, 3,4-difluorobenzyl, 3,5-dichlorobenzyl and 3-trifluoromethylbenzyl;

$R^2$ is selected from the group consisting of t-butyl, 2-(phenyl)ethyl, trichloromethyl, 3-carboxybenzyl, 3-methoxybenzyl, 2-(2-pyridyl)ethyl and 2-(2-thienyl)ethyl;

$X^1$, $X^2$, $X^3$ and $X^4$ are independently absent or CO; such that one of $X^1$ or $X^2$ and one of $X^3$ or $X^4$ is CO;

A is selected from the group consisting of 1,3-propyl, 1S,3R-cyclopentyl-methyl, 1,3-cyclohexyl-methyl-, 1S,3R-cyclohexyl-methyl- and 1R,3S-cyclohexyl-methyl-;

$R^3$ is selected from the group consisting of phenylamino, 4-fluorophenyl, 3-fluorobenzyl and 4-fluorobenzyl;

Y is -3-O—;

n is 2;

$R^4$ is selected from the group consisting of hydrogen, 4-morpholinyl, 1-pyrrolidinyl, 1-piperidinyl and di(methyl)amino;

$R^5$ is selected from the group consisting of hydrogen, 2-methyl and 6-methyl;

and the pharmaceutically acceptable salts, esters and pro-drug forms thereof.

Particularly preferred are compounds of the formula (I) wherein $R^1$ is selected from the group consisting of benzyl, 3-nitrobenzyl, 3-chlorobenzyl, 3,4-dichlorobenzyl, 3,4-difluorobenzyl and 3-trifluoromethylbenzyl;

$R^2$ is selected from the group consisting of t-butyl, 2-(phenyl)ethyl, trichloromethyl, 2-(2-pyridyl)ethyl and 2-(2-thienyl)ethyl;

$X^1$, $X^2$, $X^3$ and $X^4$ are independently absent or CO; such that one of $X^1$ or $X^2$ and one of $X^3$ or $X^4$ is CO;

A is selected from the group consisting of 1,3-propyl, 1S,3R-cyclopentyl-methyl, 1,3-cyclohexyl-methyl-, 1S,3R-cyclohexyl-methyl- and 1R,3S-cyclohexyl-methyl-;

$R^3$ is selected from the group consisting of phenylamino, 4-fluorophenyl, 3-fluorobenzyl and 4-fluorobenzyl;

Y is -3-O—;

n is 2;

$R^4$ is selected from the group consisting of hydrogen, 4-morpholinyl, 1-pyrrolidinyl and 1-piperidinyl;

$R^5$ is selected from the group consisting of hydrogen and 2-methyl;

and the pharmaceutically acceptable salts, esters and pro-drug forms thereof.

In still another particularly preferred embodiment of the present invention are compounds of the formula (I) wherein $R^1$ is 3-chlorobenzyl, $R^2$ is trichloromethyl, $X^1$ is CO, $X^2$ is absent, $X^3$ is absent, $X^4$ is CO, A is 1S,3R-cyclohexyl-methyl-, $R^3$ is 4-fluorophenyl, Y is -3-O—, n is 2, $R^4$ is 1-piperidinyl, $R^5$ is hydrogen and the pharmaceutically acceptable salts, esters and pro-drug forms thereof.

In still another particularly preferred embodiment of the present invention are compounds of the formula (I) wherein $R^1$ is 3-chlorobenzyl, $R^2$ is trichloromethyl, $X^1$ is CO, $X^2$ is absent, $X^3$ is absent, $X^4$ is CO, A is 1R,3S-cyclohexyl-methyl-, $R^3$ is 4-fluorophenyl, Y is -3-O—, n is 2, $R^4$ is 1-piperidinyl, $R^5$ is hydrogen and the pharmaceutically acceptable salts, esters and pro-drug forms thereof.

Listed in Tables 1–16 are specific compounds of the present invention.

TABLE 1

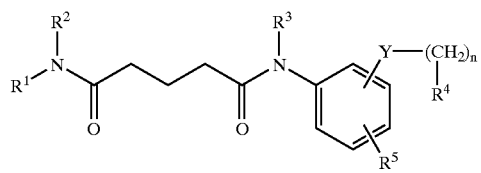

| ID # | $R^1$ | $R^2$ | $R^3$ |
|---|---|---|---|
| 128 | benzyl | 2-(phenyl)ethyl | 4-fluorobenzyl |
| 163 | 3-chlorobenzyl | 2-(phenyl)ethyl | 4-fluorobenzyl |
| 164 | benzyl | 2-(phenyl)ethyl | 3-fluorobenzyl |
| 165 | benzyl | 2-(phenyl)ethyl | 2-fluorobenzyl |
| 166 | benzyl | 2-(phenyl)ethyl | 4-methoxybenzyl |
| 167 | benzyl | 2-(phenyl)ethyl | 4-trifluoromethylbenzyl |
| 168 | benzyl | 2-(phenyl)ethyl | 4-chlorobenzyl |

TABLE 2

| ID | $R^1$ | $R^2$ | $R^3$ | Y | n | $R^4$ | $R^5$ |
|---|---|---|---|---|---|---|---|
| 129 | benzyl | 2-(phenyl)ethyl | 4-fluorobenzyl | 3-O | 2 | 4-morpholinyl | H |
| 159 | benzyl | 3-(phenyl)propyl | 4-fluorobenzyl | 3-O | 2 | 4-morpholinyl | H |

TABLE 2-continued

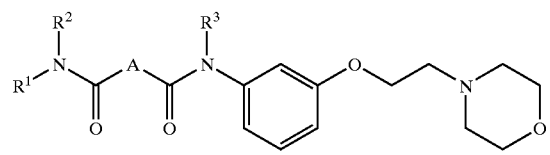

| ID | R¹ | R² | R³ | Y | n | R⁴ | R⁵ |
|---|---|---|---|---|---|---|---|
| 162 | 3-chlorobenzyl | 2-(phenyl)ethyl | 4-fluorobenzyl | 3-O | 2 | 4-morpholinyl | H |
| 169 | benzyl | 2-(phenyl)ethyl | 3-fluorobenzyl | 3-O | 2 | 4-morpholinyl | H |
| 170 | benzyl | 2-(phenyl)ethyl | 2-fluorobenzyl | 3-O | 2 | 4-morpholinyl | H |
| 171 | benzyl | 2-(phenyl)ethyl | 4-methoxybenzyl | 3-O | 2 | 4-morpholinyl | H |
| 172 | benzyl | 2-(phenyl)ethyl | 4-trifluoromethylbenzyl | 3-O | 2 | 4-morpholinyl | H |
| 173 | benzyl | 2-(phenyl)ethyl | 4-chlorobenzyl | 3-O | 2 | 4-morpholinyl | H |
| 175 | benzyl | 2-(phenyl)ethyl | 4-fluorobenzyl | 3-O— | 0 | H | H |
| 176 | benzyl | 2-(phenyl)ethyl | 4-fluorobenzyl | 3-O | 2 | 2-oxo-pyrrolidin-1-yl | H |
| 177 | benzyl | 2-(phenyl)ethyl | 4-fluorobenzyl | 3-O | 2 | dimethylamino ethyloxyethyl | H |
| 178 | benzyl | 2-(phenyl)ethyl | 4-fluorobenzyl | 3-O | 2 | diethylamino | H |
| 179 | benzyl | 2-(phenyl)ethyl | 4-fluorobenzyl | 3-O | 2 | 1-piperazinyl | H |
| 180 | benzyl | 2-(phenyl)ethyl | 4-fluorobenzyl | 3-O | 2 | 1-pyrrolidinyl | H |
| 181 | benzyl | 2-(phenyl)ethyl | 4-fluorobenzyl | 3-O | 2 | dimethylamino | H |
| 182 | benzyl | 2-(phenyl)ethyl | 4-fluorobenzyl | 3-O | 2 | 1-piperidinyl | H |
| 187 | benzyl | 2-(phenyl)ethyl | 4-fluorobenzyl | 3-O | 3 | dimethylamino | H |
| 188 | benzyl | 2-(phenyl)ethyl | 4-fluorobenzyl | 3-O | 3 | 1-piperidinyl | H |
| 191 | benzyl | 2-(phenyl)ethyl | 4-fluorobenzyl | 4-O | 2 | 1-pyrrolidinyl | H |
| 192 | benzyl | 2-(phenyl)ethyl | 4-fluorobenzyl | 4-O | 2 | 4-morpholinyl | H |
| 193 | benzyl | 2-(phenyl)ethyl | 4-fluorobenzyl | 4-O | 3 | 1-piperidinyl | H |
| 194 | benzyl | 2-(phenyl)ethyl | 4-fluorobenzyl | 4-O | 2 | dimethylamino | H |
| 195 | benzyl | 2-(phenyl)ethyl | 4-fluorobenzyl | 4-O | 2 | diethylamino | H |
| 196 | benzyl | 2-(phenyl)ethyl | 4-fluorobenzyl | 3-O | 2 | 1-pyrrolidinyl | 2-methyl |
| 197 | 3-nitrobenzyl | 2-(phenyl)ethyl | 4-fluorobenzyl | 3-O | 2 | 1-pyrrolidinyl | H |
| 198 | 3-chlorobenzyl | 3-methoxybenzyl | 4-fluorobenzyl | 3-O | 2 | 1-pyrrolidinyl | H |
| 199 | 3,5-dichlorobenzyl | 2-(phenyl)ethyl | 4-fluorobenzyl | 3-O | 2 | 1-pyrrolidinyl | H |
| 200 | 3-trifluoromethylbenzyl | 2-(phenyl)ethyl | 4-fluorobenzyl | 3-O | 2 | 1-pyrrolidinyl | H |
| 201 | 3-chlorobenzyl | 2-(2-pyridyl)ethyl | 4-fluorobenzyl | 3-O | 2 | 1-pyrrolidinyl | H |
| 202 | 3-chlorobenzyl | 2-(4-chlorophenyl)ethyl | 4-fluorobenzyl | 3-O | 2 | 1-pyrrolidinyl | H |
| 203 | 3-chlorobenzyl | 2-(1-pyrrolidinyl)ethyl | 4-fluorobenzyl | 3-O | 2 | 1-pyrrolidinyl | H |
| 204 | 3-chlorobenzyl | 2-(2-thienyl)ethyl | 4-fluorobenzyl | 3-O | 2 | 1-pyrrolidinyl | H |
| 205 | 3-nitrobenzyl | 2-(phenyl)ethyl | 4-fluorobenzyl | 3-O | 2 | 4-morpholinyl | H |
| 206 | 3-chlorobenzyl | 3-methoxybenzyl | 4-fluorobenzyl | 3-O | 2 | 4-morpholinyl | H |
| 207 | benzyl | 2-(phenyl)ethyl | 4-fluorobenzyl | 3-O | 2 | 1-pyrrolidinyl | 6-methyl |
| 215 | 2-(phenyl)ethyl | 3-carboxybenzyl | 4-fluorobenzyl | 3-O | 2 | 1-pyrrolidinyl | 2-methyl |
| 234 | benzyl | 2-phenyl)ethyl | 4-fluorobenzyl | 3-O | 2 | 4-morpholinyl | 2-methyl |

TABLE 3

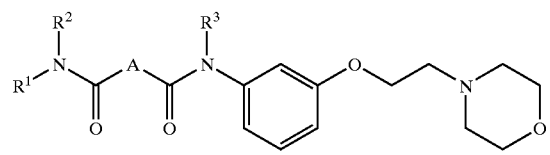

| ID | R¹ | R² | A | R³ |
|---|---|---|---|---|
| 154 | benzyl | 2-(phenyl)ethyl | 2-cyclopentenyl-1,3-n-propyl | 4-fluorobenzyl |
| 155 | benzyl | 2-(phenyl)ethyl | cis-1,2-cyclohex-4-enyl | 4-fluorobenzyl |
| 156 | benzyl | 2-(phenyl)ethyl | 1,2-cylopentenyl | H |
| 160 | benzyl | 2-(phenyl)ethyl | 1,3-n-butyl | 4-fluorobenzyl |
| 189 | benzyl | 2-(phenyl)ethyl | 2-methyl-(1,3-propyl) | 4-fluorobenzyl |
| 190 | benzyl | 2-(phenyl)ethyl | 1,1-dimethyl-(1,3-propyl) | 4-fluorobenzyl |

TABLE 4

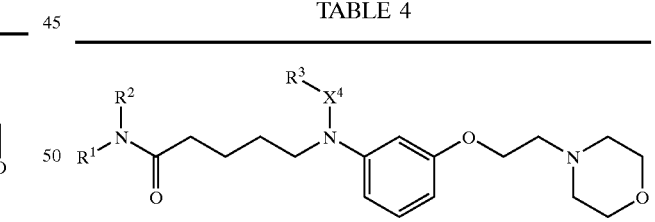

| ID | R¹ | R² | X⁴ | R³ |
|---|---|---|---|---|
| 5 | benzyl | 2-(phenyl)ethyl | CO | phenylamino |
| 6 | benzyl | 2-(phenyl)ethyl | CO | 4-methylphenyl |
| 7 | benzyl | 2-(phenyl)ethyl | CO | 4-fluorophenyl |
| 12 | benzyl | ethyl | SO₂ | 4-methylphenyl |
| 13 | benzyl | ethyl | CO | 4-methylphenyl |
| 14 | benzyl | ethyl | CO | 4-fluorophenyl |
| 19 | benzyl | methyl | CO | phenylamino |
| 20 | benzyl | methyl | SO₂ | 4-methylphenyl |

TABLE 4-continued

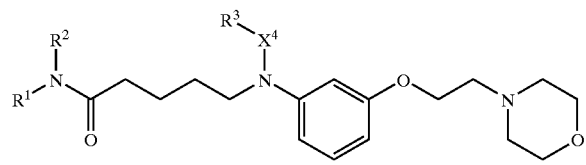

| ID | R¹ | R² | X⁴ | R³ |
|---|---|---|---|---|
| 21 | benzyl | methyl | CO | 4-methylphenyl |
| 22 | benzyl | methyl | CO | 4-fluorophenyl |
| 26 | benzyl | benzyl | CO | phenylamino |
| 27 | benzyl | benzyl | SO₂ | 4-methylphenyl |
| 28 | benzyl | benzyl | CO | 4-methylphenyl |
| 29 | benzyl | benzyl | CO | 4-fluorophenyl |
| 34 | 4-methylbenzyl | ethyl | CO | phenylamino |
| 35 | 4-methylbenzyl | ethyl | SO₂ | 4-methylphenyl |
| 36 | 4-methylbenzyl | ethyl | CO | 4-methylphenyl |
| 37 | 4-methylbenzyl | ethyl | CO | 4-fluorophenyl |

TABLE 5

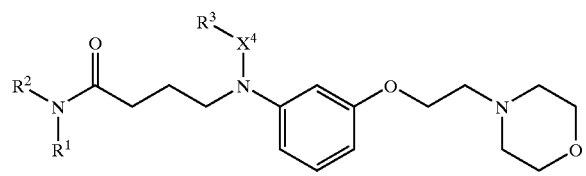

| ID | R¹ | R² | X⁴ | R³ |
|---|---|---|---|---|
| 1 | benzyl | 2-(phenyl)ethyl | CO | phenylamino |
| 2 | benzyl | 2-(phenyl)ethyl | SO₂ | 4-methylphenyl |
| 3 | benzyl | 2-(phenyl)ethyl | CO | 4-methylphenyl |
| 4 | benzyl | 2-(phenyl)ethyl | CO | 4-fluorophenyl |
| 8 | benzyl | ethyl | CO | phenylamino |
| 9 | benzyl | ethyl | SO₂ | 4-methylphenyl |
| 10 | benzyl | ethyl | CO | 4-methylphenyl |

TABLE 5-continued

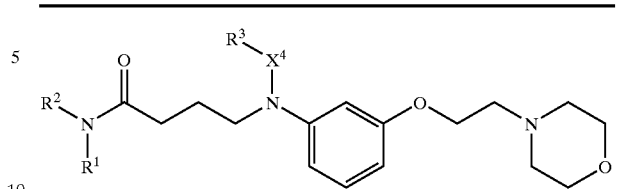

| ID | R¹ | R² | X⁴ | R³ |
|---|---|---|---|---|
| 11 | benzyl | ethyl | CO | 4-fluorophenyl |
| 15 | benzyl | methyl | CO | phenylamino |
| 16 | benzyl | methyl | SO₂ | 4-methylphenyl |
| 17 | benzyl | methyl | CO | 4-methylphenyl |
| 18 | benzyl | methyl | CO | 4-fluorophenyl |
| 23 | benzyl | benzyl | CO | phenylamino |
| 24 | benzyl | benzyl | SO₂ | 4-methylphenyl |
| 25 | benzyl | benzyl | CO | 4-methylphenyl |
| 30 | 4-methyl-benzyl | ethyl | CO | phenylamino |
| 31 | 4-methyl-benzyl | ethyl | SO₂ | 4-methylphenyl |
| 32 | 4-methyl-benzyl | ethyl | CO | 4-methylphenyl |
| 33 | 4-methyl-benzyl | ethyl | CO | 4-fluorophenyl |
| 143 | H | diphenylmethyl | CO | 4-fluorophenyl |
| 144 | benzyl | 3-(phenyl)propyl | CO | 4-fluorophenyl |
| 145 | benzyl | 2,2-dimethylpropyl | CO | 4-fluorophenyl |
| 146 | benzyl | 2-(4-methoxyphenyl)ethyl | CO | 4-fluorophenyl |
| 147 | 3-chloro-benzyl | 2-(4-methoxyphenyl)ethyl | CO | 4-fluorophenyl |

TABLE 6

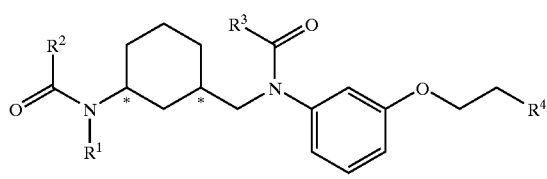

| ID | R¹ | R² | Stereo# | R³ | R⁴ |
|---|---|---|---|---|---|
| 232 | 3-chlorobenzyl | t-butyl | cis racemate | 4-fluorophenyl | N-methyl-N-benzyl-amino |
| 233 | 3-chlorobenzyl | t-butyl | cis racemate | 4-fluorophenyl | di(ethyl)amino |
| 235 | 3-chlorobenzyl | t-butyl | cis racemate | 4-fluorophenyl | 2-(1-methyl)pyrrolidinyl |
| 236 | 3-chlorobenzyl | trichloromethyl | cis racemate | 4-fluorophenyl | 2-(1-methyl)pyrrolidinyl |
| 237 | 3-chlorobenzyl | t-butyl | cis racemate | 4-fluorophenyl | 1-piperidinyl |
| 238 | 3-chlorobenzyl | trichloromethyl | cis racemate | 4-fluorophenyl | 1-piperidinyl |
| 239[a] | 3-chlorobenzyl | trichloromethyl | 1S, 3R | 4-fluorophenyl | 1-piperidinyl |
| 240[b] | 3-chlorobenzyl | trichloromethyl | 1R, 3S | 4-fluorophenyl | 1-piperidinyl |
| 264 | hydrogen | 3-carboxy-n-propyl | cis racemate | 4-fluorophenyl | 1-piperidinyl |
| 265 | hydrogen | 3-carboxy-1,2,2-trimethylcyclopentyl | cis racemate | 4-fluorophenyl | 1-piperidinyl |
| 266 | hydrogen | 3-methyl-3-carboxy-n-butyl | cis racemate | 4-fluorophenyl | 1-piperidinyl |
| 267 | hydrogen | (1-carboxymethyl-cyclopentyl)-methyl | cis racemate | 4-fluorophenyl | 1-piperidinyl |
| 268 | hydrogen | 3-carboxy-2,2-dimethyl-n-propyl | cis racemate | 4-fluorophenyl | 1-piperidinyl |

The term "cis racemate" denotes a mixture of four possible diastereomers, with the two cis diastereomers predominately present.

TABLE 7

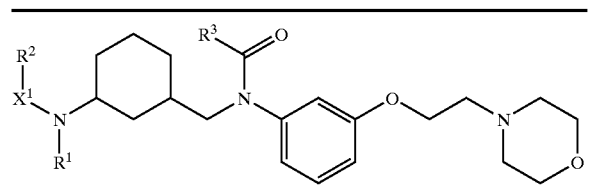

| ID | R¹ | X¹ | R² | R³ |
|---|---|---|---|---|
| 40 | benzyl | CO | phenylamino | phenylamino |
| 41 | benzyl | CO | 3-methoxyphenyl | phenylamino |
| 42 | benzyl | CO | t-butyl | phenylamino |
| 43 | benzyl | CO | 2-(phenyl)ethyl | phenylamino |
| 44 | benzyl | CO | 2-naphthyl | phenylamino |
| 45 | benzyl | CO | 3-nitrophenyl | phenylamino |
| 46 | benzyl | CO | diphenylmethyl | phenylamino |
| 47 | 3-chlorobenzyl | CO | trichloromethyl | phenylamino |
| 48 | benzyl | CO | 2-furyl | phenylamino |
| 49 | 3-chlorobenzyl | CO | 3,5-di-trifluoromethylphenyl | phenylamino |
| 50 | 3-chlorobenzyl | CO | 4-biphenyl | phenylamino |
| 51 | 3-chlorobenzyl | CO | 3-methoxyphenyl | phenylamino |
| 52 | 3-chlorobenzyl | CO | t-butyl | phenylamino |
| 53 | 3-chlorobenzyl | CO | 2-(phenyl)ethyl | phenylamino |
| 54 | 3-chlorobenzyl | CO | 2-naphthyl | phenylamino |
| 55 | 3-chlorobenzyl | CO | 3-nitrophenyl | phenylamino |
| 56 | 3-chlorobenzyl | CO | diphenyl methyl | phenylamino |
| 57 | benzyl | SO₂ | 2-naphthyl | phenylamino |
| 58 | 3-fluorobenzyl | CO | trichloromethyl | phenylamino |
| 59 | 3,4-dichlorobenzyl | CO | trichloromethyl | phenylamino |
| 60 | 3,5-dichlorobenzyl | CO | trichloromethyl | phenylamino |
| 61 | 3-methoxybenzyl | CO | trichloromethyl | phenylamino |
| 62 | 3-trifluoromethylbenzyl | CO | trichloromethyl | phenylamino |
| 63 | 4-chlorobenzyl | CO | trichloromethyl | phenylamino |
| 64 | 1-naphthyl-methyl | CO | trichloromethyl | phenylamino |
| 65 | 3-nitrobenzyl | CO | trichloromethyl | phenylamino |
| 66 | 2,3-dichlorobenzyl | CO | trichloromethyl | phenylamino |
| 67 | benzyl | CO | trichloromethyl | phenylamino |
| 68 | 2-pyridyl-methyl | CO | trichloromethyl | phenylamino |
| 69 | H | CO | phenynamino | phenylamino |
| 70 | H | CO | 2-furyl | phenylamino |
| 71 | H | SO₂ | 2-naphthyl | phenylamino |
| 72 | H | CO | trichloromethyl | phenylamino |
| 73 | H | CO | trifluoromethyl | phenylamino |
| 74 | H | CO | 3,5-di-trifluoromethylphenyl | phenylamino |
| 75 | H | CO | 4-biphenyl | phenylamino |
| 76 | H | CO | 3-methoxyphenyl | phenylamino |
| 77 | H | CO | t-butyl | phenylamino |
| 78 | H | CO | 2-(phenyl)ethyl | phenylamino |
| 79 | H | CO | 2-naphthyl | phenylamino |
| 80 | H | CO | 3-nitrophenyl | phenylamino |
| 81 | H | CO | diphenylmethyl | phenylamino |
| 82 | benzyl | CO | 3,5-di(trifluoromethyl)phenyl | phenylamino |
| 83 | benzyl | CO | 4-biphenyl | phenylamino |
| 86 | 3-chlorobenzyl | CO | 3-hydroxyphenyl | phenylamino |
| 90 | 2-pyridyl-methyl | CO | trichloromethyl | 4-fluorophenyl |
| 91 | H | CO | trichloromethyl | 4-fluorophenyl |
| 92 | 2,3-dichlorobenzyl | CO | trichloromethyl | 4-fluorophenyl |
| 93 | 3-nitrobenzyl | CO | trichloromethyl | 4-fluorophenyl |
| 94 | 1-naphthyl-methyl | CO | trichloromethyl | 4-fluorophenyl |
| 95 | 4-chlorobenzyl | CO | trichloromethyl | 4-fluorophenyl |
| 96 | 3-trifluoromethylbenzyl | CO | trichloromethyl | 4-fluorophenyl |
| 97 | 3-methoxybenzyl | CO | trichloromethyl | 4-fluorophenyl |
| 98 | 3,5-dichlorobenzyl | CO | trichloromethyl | 4-fluorophenyl |
| 99 | 3,4-dichlorobenzyl | CO | trichloromethyl | 4-fluorophenyl |

TABLE 7-continued

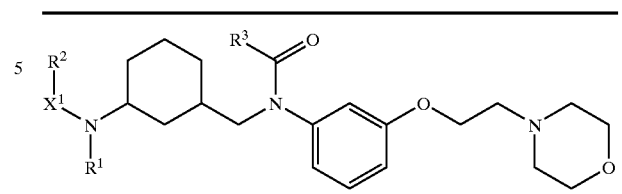

| ID | R¹ | X¹ | R² | R³ |
|---|---|---|---|---|
| 100 | 3-fluorobenzyl | CO | trichloromethyl | 4-fluorophenyl |
| 101 | 3-chlorobenzyl | CO | diphenylmethyl | 4-fluorophenyl |
| 102 | 3-chlorobenzyl | CO | 3-nitrophenyl | 4-fluorophenyl |
| 103 | 3-chlorobenzyl | CO | 2-naphthyl | 4-fluorophenyl |
| 104 | 3-chlorobenzyl | CO | 2-(phenyl)ethyl | 4-fluorophenyl |
| 105 | 3-chlorobenzyl | CO | t-butyl | 4-fluorophenyl |
| 106 | 3-chlorobenzyl | CO | 3-methoxyphenyl | 4-fluorophenyl |
| 107 | 3-chlorobenzyl | CO | 3,5-di-trifluoromethylphenyl | 4-fluorophenyl |
| 108 | 3-chlorobenzyl | CO | trifluoromethyl | 4-fluorophenyl |
| 109 | 3-chlorobenzyl | CO | 4-biphenyl | 4-fluorophenyl |
| 110 | 3-chlorobenzyl | CO | 3,3,3-trifluoropropan-2-onyl | 4-fluorophenyl |
| 111 | 3-chlorobenzyl | CO | trichloromethyl | 4-fluorophenyl |
| 112 | benzyl | CO | diphenylmethyl | 4-fluorophenyl |
| 113 | benzyl | CO | 3-nitrophenyl | 4-fluorophenyl |
| 114 | benzyl | CO | 2-naphthyl | 4-fluorophenyl |
| 115 | benzyl | CO | 2-(phenyl)ethyl | 4-fluorophenyl |
| 116 | benzyl | CO | t-butyl | 4-fluorophenyl |
| 117 | benzyl | CO | 3-methoxyphenyl | 4-fluorophenyl |
| 118 | benzyl | CO | 4-biphenyl | 4-fluorophenyl |
| 119 | benzyl | CO | 3,5-ditrifluoromethylphenyl | 4-fluorophenyl |
| 120 | benzyl | CO | trifluoromethyl | 4-fluorophenyl |
| 121 | benzyl | CO | 3,3,3-trifluoropropan-2-onyl | 4-fluorophenyl |
| 122 | benzyl | CO | trichloromethyl | 4-fluorophenyl |
| 123 | benzyl | SO₂ | 2-naphthyl | 4-fluorophenyl |
| 124 | benzyl | CO | 2-furyl | 4-fluorophenyl |
| 125 | benzyl | CO | phenylamino | 4-fluorophenyl |
| 241 | 3-chlorobenzyl | CO | 3-methoxybenzyl | 4-fluorophenyl |
| 242 | 3-chlorobenzyl | CO | 2-cyclopentylethyl | 4-fluorophenyl |
| 243 | 3-chlorobenzyl | CO | 4-methoxybenzyl | 4-fluorophenyl |
| 244 | 3-chlorobenzyl | CO | Benzyl | 4-fluorophenyl |
| 245 | 3-chlorobenzyl | CO | 3,4-dimethoxybenzyl | 4-fluorophenyl |
| 246 | 3-chlorobenzyl | CO | t-butylmethyl | 4-fluorophenyl |
| 247 | 3-chlorobenzyl | CO | 1(1-phenyl)propyl | 4-fluorophenyl |
| 248 | 3-chlorobenzyl | CO | 2-thienylmethyl | 4-fluorophenyl |
| 249 | 3-chlorobenzyl | CO | 4-fluorobenzyl | 4-fluorophenyl |

TABLE 8

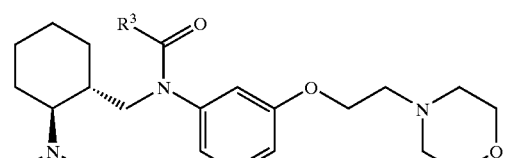

| ID | R¹ | R² | R³ |
|---|---|---|---|
| 158 | H | trichloromethyl | 4-fluorophenyl |
| 161 | 3-chlorobenzyl | t-butyl | 4-fluorophenyl |
| 157 | benzyl | trifluoromethyl | 4-fluorophenyl |

TABLE 9

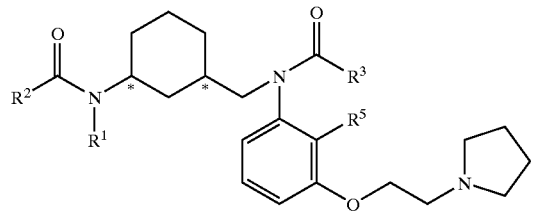

| ID | R¹ | R² | Stereo# | R³ | R⁵ |
|---|---|---|---|---|---|
| 208 | 3-nitrobenzyl | trichloromethyl | 1S, 3R | 4-fluorophenyl | $CH_3$ |
| 209 | 3-chlorobenzyl | trichloromethyl | 1S, 3R | 4-fluorophenyl | $CH_3$ |
| 210 | benzyl | trichloromethyl | 1S, 3R | 4-fluorophenyl | $CH_3$ |
| 223 | 3-chlorobenzyl | trichloromethyl | cis racemate | phenylamino | H |
| 224 | benzyl | trichloromethyl | cis racemate | phenylamino | H |
| 225 | benzyl | t-butyl | cis racemate | phenylamino | H |
| 226 | 3-chlorobenzyl | t-butyl | cis racemate | 4-fluorophenyl | H |
| 227 | 3,4-dichlorobenzyl | t-butyl | cis racemate | 4-fluorophenyl | H |
| 228 | 3,4-difluorobenzyl | t-butyl | cis racemate | 4-fluorophenyl | H |
| 229 | benzyl | t-butyl | 1S, 3R | 4-fluorophenyl | H |
| 230 | benzyl | t-butyl | 1R, 3S | 4-fluorophenyl | H |
| 211 | 3-nitrobenzyl | trichloromethyl | cis racemate | 4-fluorophenyl | H |
| 212 | 3-chlorobenzyl | trichloromethyl | cis racemate | 4-fluorophenyl | H |
| 213 | benzyl | trichloromethyl | cis racemate | 4-fluorophenyl | H |
| 214 | benzyl | t-butyl | cis racemate | 4-fluorophenyl | H |

The term "cis racemate" denotes a mixture of four possible diastereomers, with the two cis diastereomers predominately present.

TABLE 10

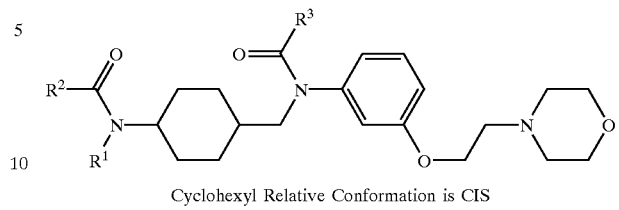

Cyclohexyl Relative Conformation is CIS

| ID | R¹ | R² | R³ |
|---|---|---|---|
| 174 | 2-pyridylmethyl | trichloromethyl | 4-fluorophenyl |
| 183 | benzyl | benzyl | phenylamino |
| 184 | 3-chlorobenzyl | 3-methoxyphenyl | phenylamino |

TABLE 10-continued

Cyclohexyl Relative Conformation is CIS

| ID | R¹ | R² | R³ |
|---|---|---|---|
| 185 | 3-chlorobenzyl | 2-furyl | phenylamino |
| 186 | 3-nitrobenzyl | 3-methoxyphenyl | phenylamino |

TABLE 11

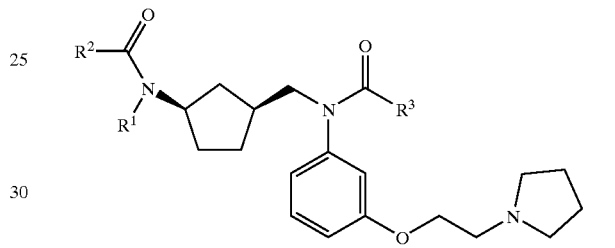

| ID | R¹ | R² | Stereo | R³ |
|---|---|---|---|---|
| 216 | benzyl | t-butyl | 1S, 3R | 4-fluorophenyl |
| 217 | 3-chlorobenzyl | t-butyl | 1S, 3R | 4-fluorophenyl |
| 218 | benzyl | trichloromethyl | 1S, 3R | 4-fluorophenyl |
| 219 | 3-nitrobenzyl | trichloromethyl | 1S, 3R | 4-fluorophenyl |
| 220 | 3,4-difluorobenzyl | t-butyl | 1S, 3R | 4-fluorophenyl |
| 231 | benzyl | trichloromethyl | 1R, 3S | 4-fluorophenyl |

TABLE 12

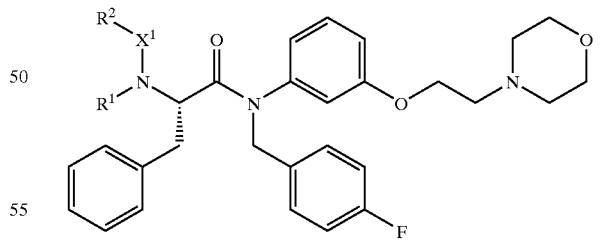

| ID | R¹ | X¹ | R² |
|---|---|---|---|
| 130 | H | CO | 2-(phenyl)ethyl |
| 131 | H | CO | trichloromethyl |
| 132 | H | CO | 4-biphenyl |
| 133 | H | CO | diphenylmethyl |
| 134 | H | CO | 3-methoxybenzyl |
| 135 | H | $SO_2$ | 4-biphenyl |
| 151 | benzyl | CO | trichloromethyl |
| 152 | benzyl | CO | 2-(phenyl)ethyl |

TABLE 13

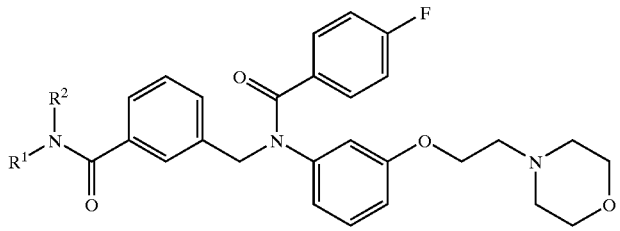

| ID | R¹ | R² |
|---|---|---|
| 136 | benzyl | 2-(phenyl)ethyl |
| 137 | H | diphenylmethyl |
| 138 | H | 2-(phenyl)ethyl |
| 139 | benzyl | 3-(phenyl)propyl |
| 140 | benzyl | 2,2-dimethylpropyl |
| 141 | 3-chlorobenzyl | 2,2-dimethylpropyl |

TABLE 14

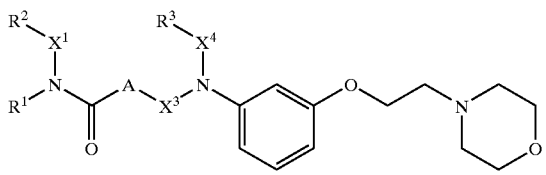

| ID | R¹, R² and X¹ Taken Together (with the amine nitrogen) | A | X³ | X⁴ | R³ |
|---|---|---|---|---|---|
| 142 | 1-phenyl-1,2,3,4-tetrahydroisoquinolin-2-yl | 1,3-phenyl-methyl | absent | CO | 4-fluoro phenyl |
| 148 | 1-phenyl-1,2,3,4-tetrahydroisoquinolin-2-yl | 1,3-n-propyl | absent | CO | 4-fluoro phenyl |
| 149 | 4-[(4-chlorophenyl)phenylmethyl]-piperazin-1-yl | 1,3-n-propyl | absent | CO | 4-fluoro phenyl |
| 150 | 2-[1-benzyl-6-methoxy-1,2,3,4-tetrahydro]-naphthyl | 1,3-n-propyl | absent | CO | 4-fluoro phenyl |
| 153 | 1-phenyl-1,2,3,4-tetrahydroisoquinolinyl | 1,3-n-propyl | CO | absent | 4-fluoro benzyl |

TABLE 15

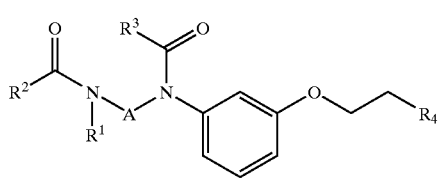

| ID | R¹ | R² | A | R³ | R⁴ |
|---|---|---|---|---|---|
| 39 | 3-chloro benzyl | trichloro methyl | methyl-1,3-cyclopentyl | phenyl amino | 4-morpholinyl |
| 221 | benzyl | t-butyl | 1,4-cyclopentyl-2-ene-methyl | 4-fluoro phenyl | 1-pyrrolidinyl |

TABLE 16

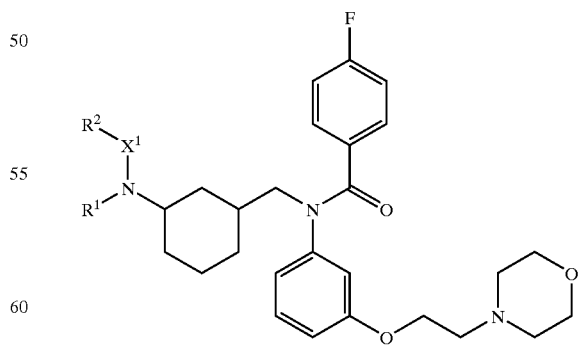

| ID | R¹, R² and X¹ Taken Together (with the amine nitrogen) |
|---|---|
| 250 | 5-t-butyl-isoindole-1,3-dione |
| 251 | 5-fluoro-isoindole-1,3-dione |

| | |
|---|---|
| 252 | benzo[e]isoindole-1,3-dione |
| 253 | 5-methyl-isoindole-1,3-dione |
| 254 | 8-aza-spiro[4.5]decane-7,9-dione |
| 255 | 5,6-dichloro-isoindole-1,3-dione |
| 256 | 5-methyl-isoindole-1,3-dione |
| 257 | isoindole-1,3-dione |
| 258 | 4,4-dimethyl-piperidine-2,6-dione |
| 259 | 5-bromo-isoindole-1,3-dione |
| 260 | 5-acetyloxy-isoindole-1,3-dione |
| 261 | 8-fluoro-benzo[e]isoindole-1,3-dione |
| 262 | 3-aza-bicyclo[3.1.0]hexane-2,4-dione |
| 263 | 4,7-dichloro-isoindole-1,3-dione |

Particularly preferred intermediates in the preparation of compounds of formula (I) are listed in Table 17 below.

TABLE 17

| ID # | $R^1$ | $R^2$ | $R^3$ | $R^4$ |
|---|---|---|---|---|
| 84 | benzyl | H | phenylamino | 4-morpholino |
| 85 | 3-chlorobenzyl | H | phenylamino | 4-morpholino |
| 87 | 3,5-dichlorobenzyl | H | phenylamino | 4-morpholino |
| 88 | 1-naphthylmethyl | H | phenylamino | 4-morpholino |
| 89 | 4-(1-hydroxy)-pyridyl | H | phenylamino | 4-morpholino |
| 222 | benzyl | benzyl | 4-fluorophenyl | 1-pyrrolidinyl |

Illustrative of the invention is a pharmaceutical composition comprising a pharmaceutically acceptable carrier and any of the compounds described above. Illustrating the invention is a pharmaceutical composition made by mixing any of the compounds described above and a pharmaceutically acceptable carrier. A further illustration of the invention is a process for making a pharmaceutical composition comprising mixing any of the compounds described above and a pharmaceutically acceptable carrier.

Included in the invention is the use of any of the compounds described above for the preparation of a medicament for treating a disorder mediated by the motilin receptor, in a subject in need thereof.

Also included in the invention is the use of any of the compounds described above for the preparation of a medicament for treating a condition selected from gastrointestinal reflux disorders, eating disorders leading to obesity and irritable bowel syndrome in a subject in need thereof.

Exemplifying the invention are methods of treating a disorder mediated by the motilin receptor, in a subject in need thereof, comprising administering to the subject a therapeutically effective amount of any of the compounds or pharmaceutical compositions described above.

An example of the invention is a method for treating a condition selected from gastrointestinal reflux disorders, eating disorders leading to obesity and irritable bowel syndrome in a subject in need thereof, comprising administering to the subject an effective amount of any of the compounds or pharmaceutical compositions described above.

Another example of the invention is the use of any of the compounds described above in the preparation of a medicament for: (a) treating gastrointestinal reflux disorders, (b) treating irritable bowel syndrome, (c) treating eating disorders leading to obesity, in a subject in need thereof.

Listed below are definitions of various terms used to describe this invention. These definitions apply to the terms as they are used throughout this specification, unless otherwise limited in specific instances, either individually or as part of a larger group.

The term "halogen" or "halo" refers to fluorine, chlorine, bromine and iodine.

The term "alkyl", unless otherwise specified, refers to straight or branched chain unsubstituted hydrocarbon groups of 1 to 20 carbon atoms, preferably 1 to 8 carbon atoms. The expression "lower alkyl" refers to straight or branched chain unsubstituted alkyl groups of 1 to 6 carbon atoms. For example, alkyl radicals include, methyl, ethyl, n-propyl, isopropyl, n-butyl, isobutyl, sec-butyl, t-butyl, n-pentyl, 3-methylbutyl, 2-pentyl, 2-methylpropyl, 2-methylbutyl, 3,3-dimethylpropyl, neo-pentyl, n-hexyl, 2-hexyl and 2-methylpentyl. Similarly, the term "alkenyl", unless otherwise specified, refers to straight or branched chain alkene groups of 2 to 10 carbon atoms. The term "lower alkenyl" refers to straight or branched chain alkene groups of 2 to 6 carbon atoms.

The term "substituted alkyl", unless otherwise specified, refers to an alkyl group substituted by, for example, one to four substituents, such as, halo, trifluoromethyl, trifluoromethoxy, hydroxy, alkoxy, cycloalkyoxy, heterocyclyloxy, oxo, alkanoyl, aryloxy, alkanoyloxy, amino, alkylamino, arylamino, aralkylamino, cycloalkylamino, heterocycloamino, disubstituted amines in which the amino substituents are independently selected from alkyl, aryl or aralkyl, alkanoylamine, aroylamino, aralkanoylamino, substituted alkanoylamino, substituted arylamino, substituted aralkanoylamino, thiol, alkylthio, arylthio, aralkylthio, cycloalkylthio, heterocyclothio, alkylthiono, arylthiono, aralkylthiono, alkylsulfonyl, arylsulfonyl, aralkylsulfonyl, sulfonamido (e.g. $SO_2NH_2$), substituted sulfonamido, nitro, cyano, carboxy, carbamyl (e.g. $CONH_2$) substituted carbamyl (e.g. CONH alkyl, CONH aryl, CONH aralkyl or cases where there are two substituents on the nitrogen selected from alkyl, aryl or aralkyl), alkoxycarbonyl, aryl, substituted aryl, guanidino and heterocyclos, such as indolyl, imidazolyl, furyl, thienyl, thiazolyl, pyrrolidyl, pyridyl, pyrimidyl and the like.

The term "cycloalkyl", unless otherwise specified, refers to saturated unsubstituted cyclic hydrocarbon ring systems, preferably containing 1 to 3 rings and 3 to 8 carbon atoms per ring. For example, cycloalkyl radicals include cyclopropyl, cyclobutyl, cyclopentyl, cyclohexyl, cycloheptyl, and the like. Similarly, the term "cycloalkenyl" refers to partially unsaturated, unsubstituted cyclic hydrocarbon groups of 3 to 20 carbon atoms, preferably 3 to 8 carbon atoms. Suitable examples of cycloalkenyl groups include cyclobutenyl, cyclopentenyl, cyclohexenyl, cyclooctyl, cyclodecyl, cyclododecyl, adamantyl, and the like.

The term "alkoxy", unless otherwise specified, refers to oxygen ether radical of the above described straight or branched chain alkyl groups. The expression "lower alkoxy" refers to unsubstituted alkoxy groups of 1 to 6 carbon atoms. Suitable examples of alkoxy groups include methoxy, ethoxy, n-propoxy, sec-butoxy, t-butoxy, n-hexyloxy and the like.

The term "aryl", unless otherwise specified, refers to monocyclic or bicyclic aromatic hydrocarbon groups having 6 to 12 carbon atoms in the ring portion, such as phenyl, naphthyl, biphenyl and diphenyl, each of which may be optionally substituted.

The term "aralkyl", unless otherwise specified, refers to an aryl group bonded directly through an alkyl group, such as benzyl, 2-(phenyl)ethyl, 3-(phenyl)propyl, naphthylmethyl and the like.

The term "substituted aryl" refers to an aryl group substituted by, for example, one to five substituents such as alkyl; substituted alkyl, halo, trifluoromethoxy, trifluoromethyl, hydroxy, alkoxy, cycloalkyloxy, heterocyclooxy, alkanoyl, alkanoyloxy, amino, alkylamino, aralkylamino, cycloalkylamino, heterocycloamino, dialkylamino, alkanoylamino, thiol, alkylthio, cycloalkylthio, heterocyclothio, ureido nitro, cyano, carboxy, carboxyalkyl, carbamyl, alkoxycarbonyl, alkylthiono, arylthiono, alkysulfonyl, sulfonamido, aryloxy and the like.

The term "diarylalkyl", unless otherwise specified, refers to an alkyl group substituted with two independently selected aryl groups. Suitable examples include diphenylmethyl, 1,1-diphenylethyl, and the like.

The term "heteroatom" shall include oxygen, sulfur and nitrogen.

The terms "heterocyclyl", "heterocyclic" and "heterocyclo", unless otherwise specified, refer to a saturated, unsaturated, partially unsaturated, aromatic, partially aromatic or non-aromatic cyclic group. Such a group, for example, can be a 4 to 7 membered monocyclic or a 7 to 11 bicyclic ring system which contains at least one heteroatom in at least one carbon atom containing ring. Each ring of the heterocyclic group containing a heteroatom may have 1, 2, 3 or 4 heteroatoms selected from nitrogen atoms, oxygen atoms and sulfur atoms, where the nitrogen and sulfur heteroatoms may also optionally be oxidized and where the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropryanyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane, tetrahydro-1, 1-dioxothienyl, dioxanyl, isothiazolidinyl, thietanyl, thiiranyl, triazinyl, triazolyl, tetrazolyl and the like.

Exemplary bicyclic heterocyclic groups include benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl, or furo[2,3-b] pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

The term "monocylic or fused bicyclic or tricyclic secondary amine ring structure" shall mean any 4 to 8 monocyclic or 7 to 11 fused bicyclic or 13 to 14 tricyclic ring structure; wherein the ring structure is saturated, partially unsaturated or benzo-fuzed; wherein the ring structure contains at least one nitrogen atom through which the ring structure is bound directly to the other portions of the compound; and wherein the ring structure may optionally containing one to three additional heteroatoms selected from nitrogen, oxygen or sulfur.

Suitable examples include 1,2,3,4-tetrahydroisoquinolinyl, 1-piperazinyl, 1,2,3,4-tetrahydronaphthyl, isoindolyl, benzo[e]isoindolyl, 8-aza-spiro[4.5]decane, 3-aza-bicyclo[3.1.o]hexane, and the like.

The monocylic, bicyclic or tricyclic secondary amine ring structure may optionally be substituted with one to five substituents independently selected from alkyl, substituted alkyl, halo, trifluoromethoxy, trifluoromethyl, hydroxy, alkoxy, cycloalkyloxy, heterocyclooxy, alkanoyl, alkanoyloxy, amino, alkylamino, aralkylamino, cycloalkylamino, heterocycloamino, dialkylamino, alkanoylamino, thiol, alkylthio, cycloalkylthio, heterocyclothio, ureido nitro, cyano, oxo, carboxy, carboxyalkyl, carbamyl, alkoxycarbonyl, alkylthiono, arylthiono, alkysulfonyl, sulfonamido, aryloxy, aryl, aralkyl, heterocyclyl, and the like.

The term "tri-halomethyl" refers to trichloromethyl, trifluoromethyl, tribromomethyl and triiodomethyl.

Under standard nomenclature used throughout this disclosure, the terminal portion of the designated side chain is described first, followed by the adjacent functionality toward the point of attachment. Thus, for example, a "phenyl (alkyl)amido(alkyl)" substituent refers to a group of the formula

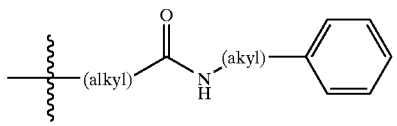

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

As used herein, the term "cis racemate" indicates a mixture of four possible diastereomers, more particularly, two cis diastereomers and two trans diastereomers, with the two cis diastereomers present in a amount equal to greater than about 75%, preferably in an amount greater than about 90%, more preferably in an amount greater than about 95%.

When a particular group is "substituted" (e.g., aryl, heteroaryl, heterocyclyl), that group may have one or more substituents, preferably from one to five substituents, more preferably from one to three substituents, most preferably from one to two substituents, independently selected from the list of substituents. Where the group has a plurality of moieties, such as "alkylamino" or "heterocyclyl-alkyl" the substitution may be on any or all of the moieties independently, e.g. in the case of "alkylamino" the substitution may be on the alkyl or amino moiety, or both.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

Suitable protecting groups as referred to within this specification include the standard hydroxy and amino protecting groups, as applicable. The terms "hydroxy protecting group" and "amino protecting group" as used herein mean any of the known protecting groups used in the art of organic synthesis, for example as described in Protective Groups in Organic Synthesis, 2$^{nd}$ Ed., T. W. Greene and P. G. M. Wuts, John Wiley & Sons, New York, 1991, hereby incorporated by reference.

Examples of hydroxy-protecting groups P, include, but are not limited to, methyl, benzyl, tetrahydropyranyl, tri($C_1$–$C_6$) alkylsilyl such as t-butyldimethylsilyl, t-butyl, 2-methoxyethoxymethyl (MEM), 4-dimethylcarbamoylbenzyl and O-phenoxyacetyl ethers. The hydroxy-protecting group selected is preferably one that is easily removable in the reaction process.

Examples of suitable amino protecting groups include, but are not limited to, acetyl (Ac), benzoyl (Bz), trifluoroacetyl (Tfa), toluenesulfonyl (Tos), benzyl (Bn), triphenylmethyl (Trt), o-nitrophenyl-sulfenyl (Nps), benzyloxycarbonyl (Cbz or Z), t-butoxycarbonyl (Boc), allyloxycarbonyl (alloc), 9-fluorenylmethyloxycarbonyl (Fmoc), 2-bromo-benzyloxycarbonyl (2-Br-Z), 2-chloro-benzyloxycarbonyl (2-Cl-Z), t-butyl-dimethylsilyloxycarbonyl, [2-(3,5-dimethoxyphenyl)-propyl-2-oxycarbonyl] (Ddz), 2,2,2-trichloroethyloxycarbonyl (Troc), biphenylylisopropyloxycarbonyl (Bpoc), and o-nitrobenzyloxycarbonyl.

Throughout this specification, certain abbreviations are employed having the following meanings, unless specifically indicated otherwise.

AcOH=Acetic Acid
ADDP=1,1'-(azodicarbonyl)dipiperidine
BSA=Bovine Serum Albumin
DCM=Dichloromethane
DEAD=Diethyl azodicarboxylate
DIEA=Diisopropylethylamine
DMAP=Di(methyl)aminopyridine
DMF=N,N-dimethylformamide
DMSO=Dimethylsulfoxide
EA=Ethyl acetate
EDCl=1-ethyl-3-(3-dimethylaminopropyl) carbodiimide
EDTA=Ethylenediamine tetraacetic acid
EGTA=Ethylene glycol-bis(β-aminoethyl ether)-N,N,N', N'-tetraacetic acid
$Et_2O$=Diethyl ether
EtOAc=Ethyl acetate
EtOH=Ethanol
$Et_3N$=Triethylamine
HEPES=N-(2-hydroxyethyl)piperazine-N-ethanesulfonic acid
LAH=Lithium Aluminum Hydride
MeOH=Methanol
MeI=Methyl Iodide
Oms=Mesylate
Otos=Tosylate
Phe=Phenyl
Pt=Protecting Group PyBOP=Benzotriazole-1-yl-oxy-tris-pyrrolidino-phosphonium hexafluorophosphate
TBAF=Tetrabutylammonium fluoride
TEA=Triethylamine
TFA=Trifluoroacetic Acid
THF=Tetrahydrofuran
Tris-HCl=Tris[hydroxymethyl]aminomethyl hydrochloride The synthesis of substituted N-benzyl-m-anisidines, compounds of formula (II), intermediates used in the synthetic route for select compounds of the invention, are known in the art.

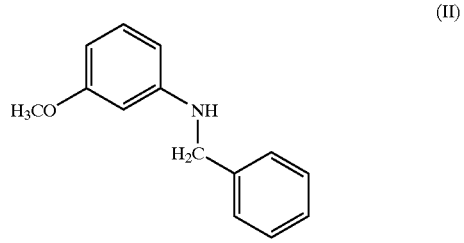

(II)

Routes for synthesis of substituted N-benzyl-m-anisidines include alkylation (Hoerlein; Chem. Ber.; 87; 1954; 463, 467, 468), reductive amination (Nussbaumer, P.; et. al.; J Med Chem.; 37; 24; 1994; 4079–4084) and reduction of the corresponding N-benzoyl-m-anisidine (Pratt; McGovern; J. Org. Chem.; 29; 1964; 1540, 1542). Additionally, N-benzyl-N-phenyl-malonamic acid methyl ester, a compound of formula (III) below, is a known compound, a variant of one of the intermediates elucidated in the synthesis that follows (Wee, A.; Tetrahedron, 50; 3; 1994; 609–626).

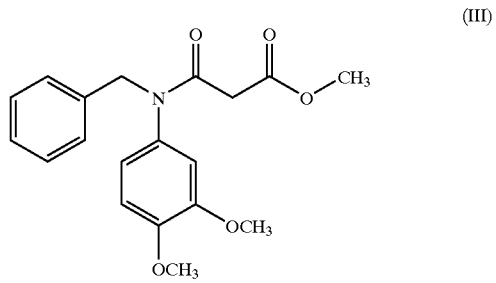

(III)

Routes to the synthesis of 4-phenyl-1,2,3,4-tetrahydroisoquinolines are also known in the literature (Maryanoff, B., et. al., J. Org. Chem., 46, 1981, 355–360; Schwan, T. et. al., J. Heterocycl. Chem., 1974, 11, 807; and references therein).

Schemes 1–8 below depict synthesis routes for producing compounds of the formula (I).

Compounds of formula (I) wherein $X^2$ and $X^3$ are each carbonyl, $X^1$ and $X^4$ are each absent and $R^3$ is —$CH_2$—$R^6$, may be produced according to the process outlined in Scheme 1. The process of Scheme 1 is particularly preferred for preparation of compounds of formula (I) wherein A is incorporated into the molecule via reaction with a suitably selected unsymmetrically substituted anhydride; wherein A is a substituted alkyl; and wherein it is desired to have the substituent closer to the $R^1X^1R^2N$ portion of the compound of formula (I).

SCHEME 1

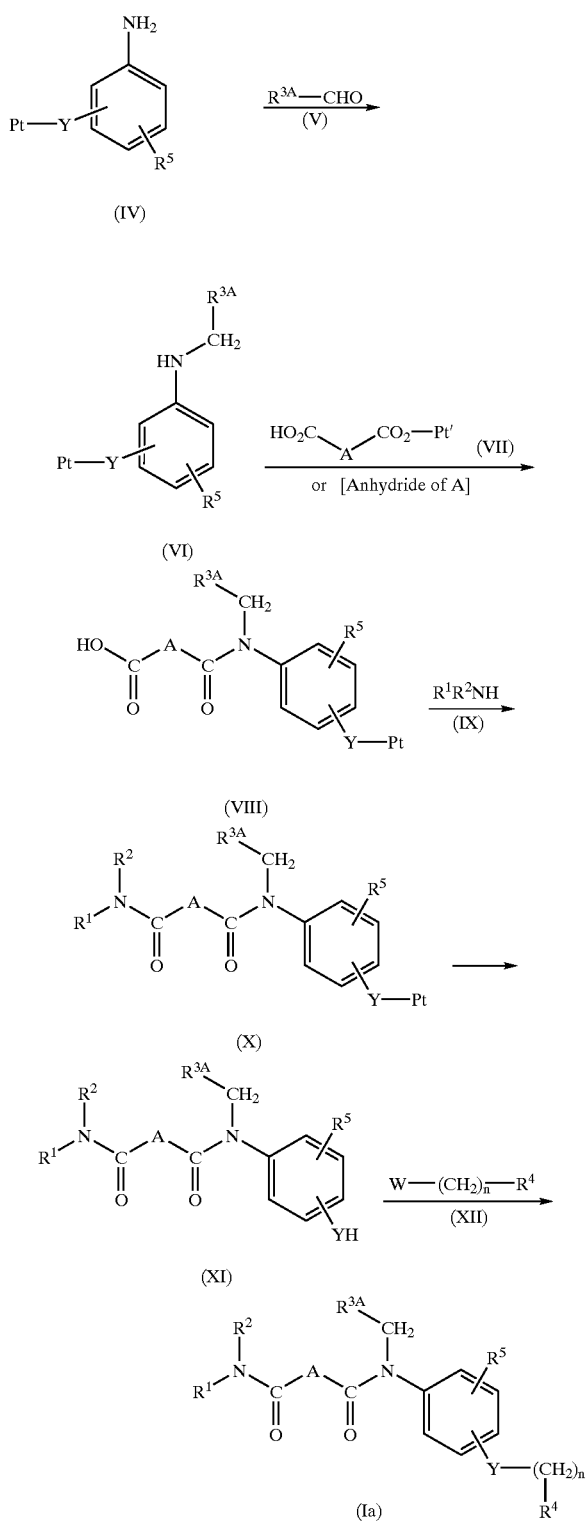

More specifically, a protected aniline derivative of formula (IV), wherein Pt represents a protecting group, a known compound or compound prepared by known methods, is reacted with a suitably substituted aldehyde of the formula (V), wherein $R^{3A}$ is selected from hydrogen, aryl, heterocyclyl, aralkyl, diarylalkyl, heterocyclo-alkyl, tri-halomethyl, alkylamino, dialkylamino, alkylaminoalkyl, arylamino, diarylamino or lower alkyl; in the presence of a reducing agent such as sodium cyanoborohydride, sodium triacetoxyborohydride, and the like, under dehydrating conditions, for example, in an acid alcohol solution such as acidic methanol or in a solution of titanium tetraisopropoxide in DCM, to produce the corresponding secondary aniline derivative of formula (VI).

The secondary aniline derivative of formula (VI) is coupled with a suitably selected, protected dicarboxylic acid of formula (VII), wherein Pt' is a protecting group or with an anhydride of the desired substituent A, to produce the corresponding acid-amide of formula (VIII).

When the secondary aniline derivative of formula (VI) is coupled with a cyclic anhydride of the desired substituent A, such as glutaric anhydride and the like, the anhydride ring is subjected to ring opening, preferably at a temperature between about room temperature and about 110° C., in an organic solvent such as chloroform, toluene, and the like.

When the secondary aniline derivative of formula (VI) is coupled with a protected dicarboxylic acid of formula (VII), the protecting group is then removed by hydrolysis, using an inorganic base such as lithium hydroxide, sodium hydroxide, potassium hydroxide, and the like, in an alcohol or in an organic solvent/water mixture such as methanol, ethanol, THF/water, preferably lithium hydroxide in THF/water.

The acid-amide compound of formula (VIII) is activated using a known coupling agent, such as EDCl and the like, and coupled with a suitably substituted amine of formula (IX), in an organic base such as TEA, DIEA, and the like, in the presence-of an organic solvent such as THF, DMF, DCM and the like, to produce the corresponding diamide of formula (X).

Alternatively, the acid-amine compound of formula (VIII) may be converted to the corresponding acid chloride with a reagent such thionyl chloride, oxalyl chloride, and the like, and then coupled to the substituted amine of formula (IX) to produce the diamide of formula (X).

The compound of formula (X) is deprotected by known methods [for example, when the protecting group is methyl ether, the methyl group is removed with boron tribromide in dichloromethane at −78° C.; when the protecting group is t-butyldimethylsilylether, the silyl group is removed with tetrabutylammonium fluoride in THF] to produce the corresponding compound of formula (XI).

The compound of formula (XI) is reacted with a suitably substituted compound of formula (XII), wherein W represents a leaving group such as halogen, OMS, OTos, and the like, in the presence of a base such as sodium hydride, potassium carbonate, and the like, in an organic solvent such as DMF, THF, and the like, to produce the corresponding compound of formula (Ia). Alternatively, when W is OH, the compound of formula (XI) may be reacted directly, under Mitsunobu conditions, to a suitably substituted compound of formula (XII).

Compounds of formula (I) wherein $X^2$ and $X^3$ are each carbonyl, $X^1$ and $X^4$ are each absent and $R^3$ is —$CH_2$—$R^6$ may alternatively be prepared according to the process outlined in Scheme 2.

SCHEME 2

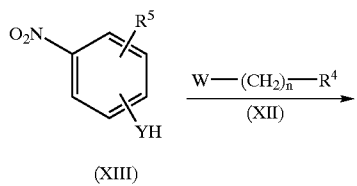

(XIII)

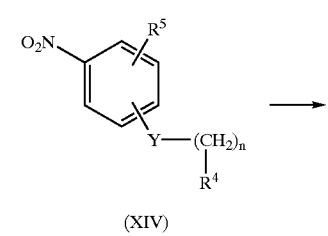

(XIV)

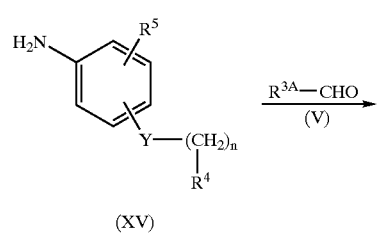

(XV)

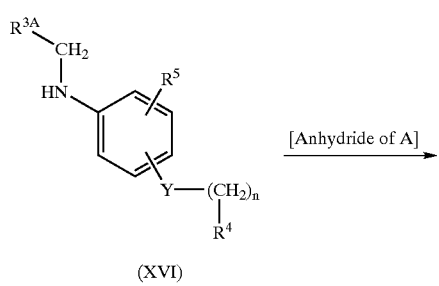

(XVI)

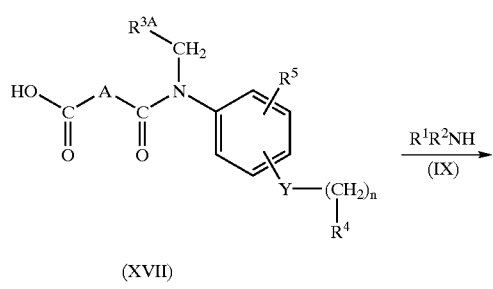

(XVII)

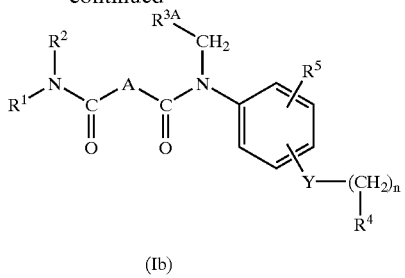

(Ib)

Accordingly, a suitably substituted nitrobenzene of formula (XIII), a compound prepared by known methods, is reacted with a suitably substituted compound of formula (XII), wherein W represents a leaving group such as halogen, OMS, OTos, and the like, in the presence of a base such as sodium hydride, triethylamine, and the like, in an organic solvent such as DMF, THF, and the like, to produce the corresponding compound of formula (XIV).

The nitro group on the compound of formula (XIV) is reduced by known methods, for example by hydrogenation over palladium on carbon in ethyl acetate, to produce the corresponding compound of formula (XV).

The compound of formula (XV) is reacted with a suitably substituted aldehyde of formula (V), wherein $R^{3A}$ is as previously defined, in the presence of a reducing agent such as sodium cyanoborohydride, sodium triacetoxyborohydride, and the like, under dehydrating conditions, for example, in an acid alcohol solution such as acidic methanol or in a solution of titanium tetraisopropoxide in DCM, to produce the corresponding compound of formula (XVI).

The compound of formula (XVI) is reacted with a suitably selected anhydride of the desired A substituent, optionally in an organic solvent such as THF, DMF, DCM, and the like, to produce the corresponding compound of formula (XVII). When reacting with a cyclic anhydride of the desired substituent A, such as glutaric anhydride and the like, the anhydride ring is subjected to ring opening, preferably at a temperature between about room temperature and about 110° C., in an organic solvent such as chloroform, toluene, and the like.

The compound of formula (XVII) is coupled with a suitably substituted amine of formula (IX), in the presence of a coupling agent, such as PyBOP, and the like, in an organic solvent such as THF, DMF, DCM, and the like, to produce the corresponding compound of formula (Ib).

Compounds of formula (I) wherein $X^2$ and $X^3$ are each carbonyl, $X^1$ and $X^4$ are each absent and $R^3$ is —$CH_2$—$R^6$, may alternatively be prepared according to the process outlined in Scheme 3. This process is particularly preferred for preparation of compounds of formula (I) wherein A is incorporated into the molecule via reaction with a suitably selected, unsymmetrically substituted anhydride; wherein A is a substituted alkyl; and wherein it is desired to have the substituent distal to the $R^1X^1R^2N$ portion of the compound of formula (I).

SCHEME 3

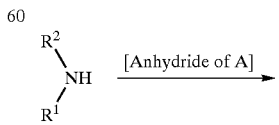

(IX)

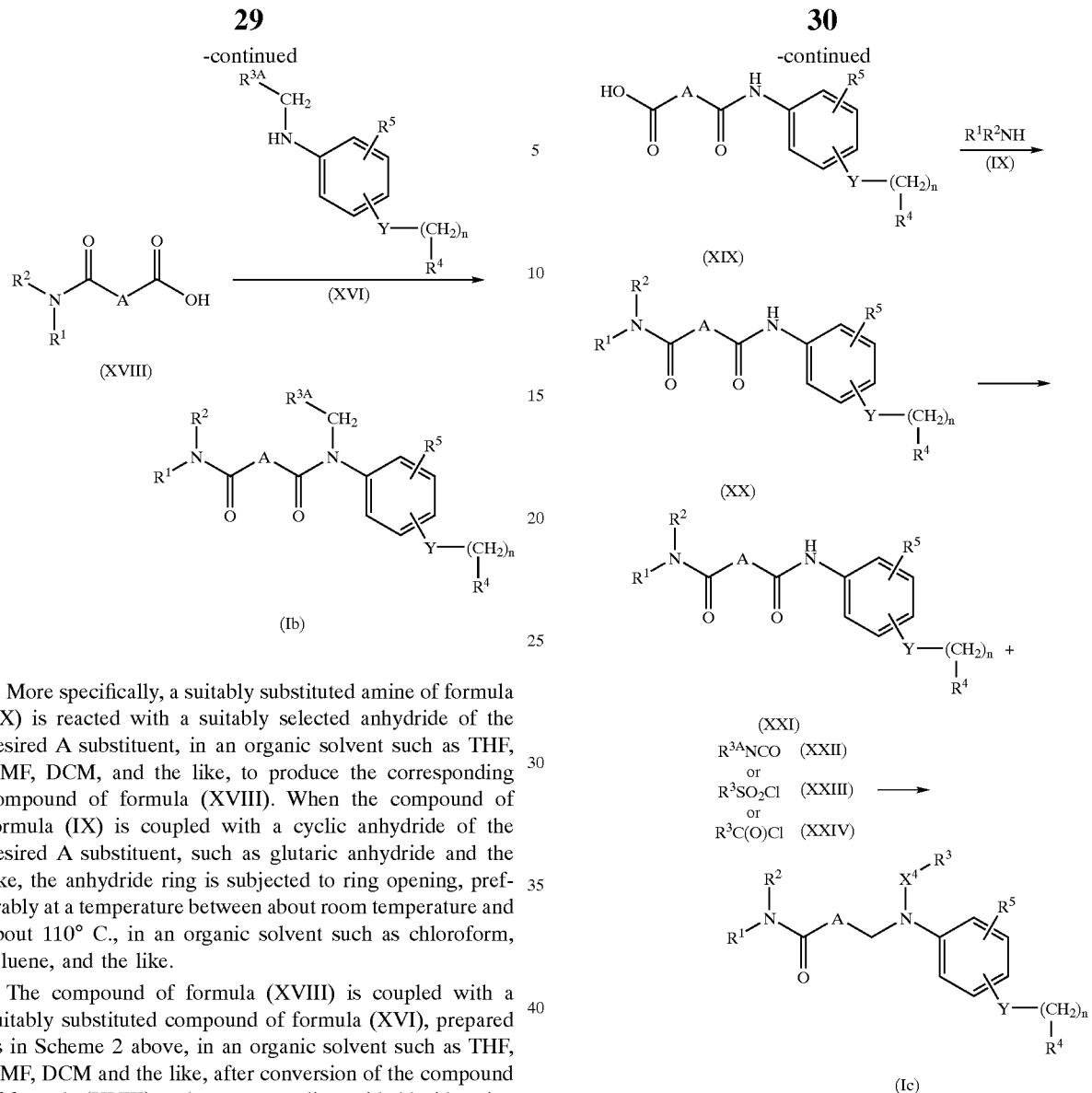

More specifically, a suitably substituted amine of formula (IX) is reacted with a suitably selected anhydride of the desired A substituent, in an organic solvent such as THF, DMF, DCM, and the like, to produce the corresponding compound of formula (XVIII). When the compound of formula (IX) is coupled with a cyclic anhydride of the desired A substituent, such as glutaric anhydride and the like, the anhydride ring is subjected to ring opening, preferably at a temperature between about room temperature and about 110° C., in an organic solvent such as chloroform, toluene, and the like.

The compound of formula (XVIII) is coupled with a suitably substituted compound of formula (XVI), prepared as in Scheme 2 above, in an organic solvent such as THF, DMF, DCM and the like, after conversion of the compound of formula (XVIII) to the corresponding acid chloride using a reagent such as thionyl chloride, oxalyl chloride, and the like, to produce the corresponding compound of formula (Ib).

Alternatively, the compound of formula (XVIII) may be coupled directly with a suitably substituted compound of formula (XVI), optionally in the presence of a coupling agent such as PyBrop, and the like, in an organic solvent such as THF, DMF, DCM, and the like.

Compounds of formula (I) wherein $X^1$ and $X^3$ are each absent, $X^2$ is carbonyl, and $X^4$ is carbonyl or sulfonyl, may be prepared according to the process outlined in Scheme 4.

SCHEME 4

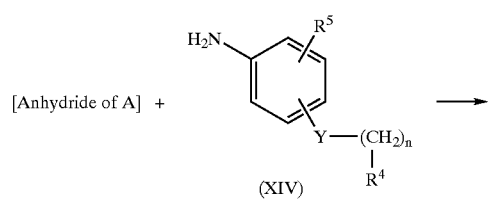

More specifically, an anhydride of the desired substituent A is reacted with a suitably substituted compound of formula (XIV), prepared as outlined in scheme 2, in an organic solvent such as THF, DMF, DCM and the like, to produce the corresponding compound of formula (XIX).

The compound of formula (XIX) is coupled with a suitably substituted amine of formula (IX), in the presence of a coupling agent, such as PyBOP, and the like, in an organic solvent such as THF, DMF, DCM and the like, to produce the corresponding compound of formula (XX).

The compound of formula (XX) is selectively reduced, by known methods, for example, by reacting with sodium cyanoborohydride in AcOH (Tetrahedron Letters, 10, 763–66, 1976), to produce the corresponding compound of formula (XXI).

The compound of formula (XXI) is reacted with an appropriately selected and suitably substituted isocyanate of formula (XXII), wherein $R^{3A}$ is a previously defined, or a sulfonyl chloride of formula (XXIII) or a carbonyl chloride of formula (XXIV), in an organic solvent such as THF, DMF, DCM and the like, to produce the corresponding compound of formula (Ic).

Compounds of formula (I) wherein $X^1$ and $X^4$ are each carbonyl or sulfonyl and $X^2$ and $X^3$ are each absent, may be prepared according to the process outlined in Scheme 5. This process is particularly preferred for the preparation of compounds of formula (I) wherein A is -cyclohexyl-methyl-, -cyclopentyl-methyl and -cyclopentenyl-methyl-.

SCHEME 5

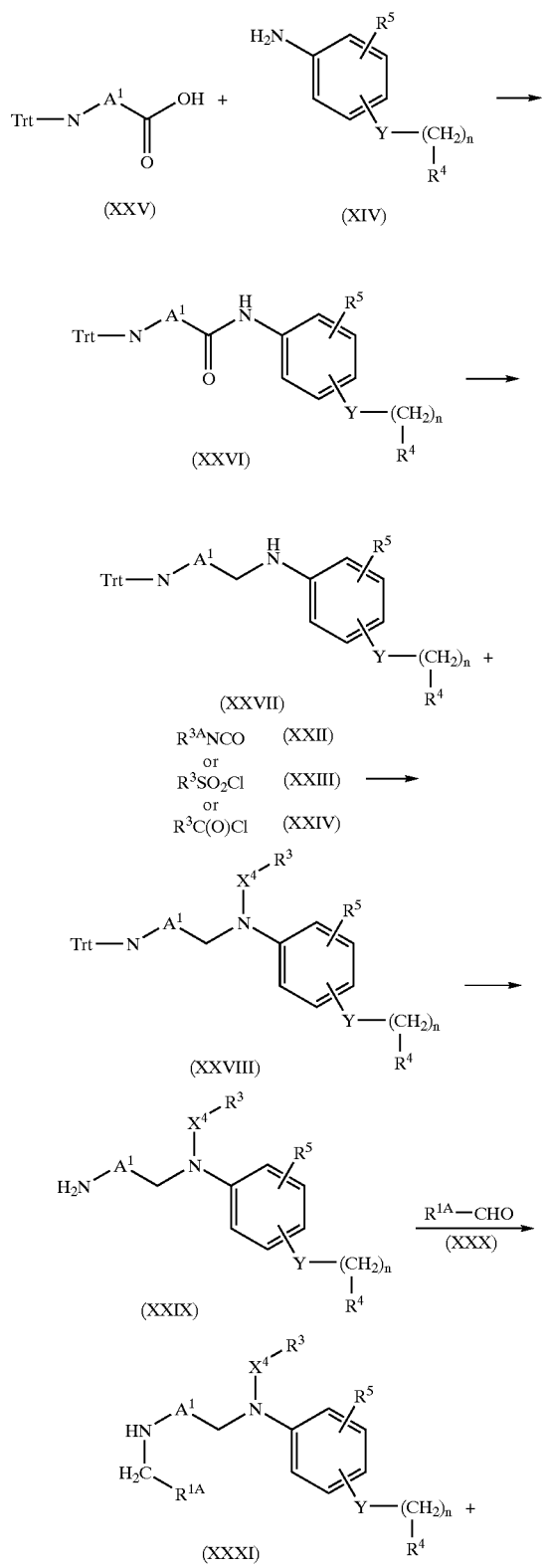

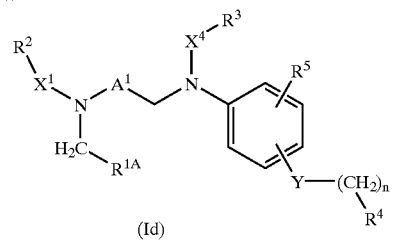

Accordingly, a trityl-protected compound of formula (XXV), wherein $A^1$ is cycloalkyl, cycloalkenyl, alkyl-cycloalkyl, aryl or alkyl-aryl, a known compound or compound prepared by known methods, [for example by the method disclosed in K. Barlos, D. Theodoropoulos, and D. Papaioannou in J. Org. Chem. 1982, 47, 1324–1326], is coupled to a suitably substituted compound of formula (XIV), prepared according to Scheme 2 above, using a coupling agent such as PyBOP, and the like, to produce the corresponding compound of formula (XXVI).

The compound of formula (XXVI) is subjected to reduction of the carbonyl group using known reducing agents, for example borane dimethylsulfide at reflux, lithium aluminum hydride in THF, and the like, to produce the corresponding compound of formula (XXVII).

The compound of formula (XXVII) is reacted with an appropriately selected and suitably substituted isocyanate of formula (XXII), wherein $R^{3A}$ is as previously defined, sulfonyl chloride of formula (XXIII) or carbonyl chloride of formula (XXIV), in an organic solvent such as DCM, toluene, chloroform, and the like, to produce the corresponding compound of formula (XXVIII).

The compound of formula (XXVIII) is deprotected by removal of the trityl protecting group, using a solution of trifluoroacetic acid in dichloromethane, to produce the corresponding compound of formula (XXIX).

The compound of formula (XXIX) is reacted with a suitably substituted aldehyde of formula (XXX), wherein $R^{1A}$ is selected from the group consisting of hydrogen, aryl, aralkyl, heterocyclyl, diarylalkyl, heterocyclyl-alkyl, and lower alkyl; wherein the alkyl, aryl, heterocyclyl or amino group may be substituted with one or more substituents independently selected from halogen, hydroxy, nitro, carboxy, cyano, amino, dialkylamino, lower alkoxy, lower alkyl, tri-halomethyl, alkylamino, carboxy or alkoxycarbonyl; by known methods, [for example by reductive amination or by the method of R. Mattson, et. al., in J. Org. Chem. 1990, 55, 2552–2554 using stepwise addition of titanium tetraisopropoxide neat or in a dichloromethane, followed by addition of methanol and sodiumcyanoborohydride], to produce the corresponding compound of formula (XXXI).

The compound of formula (XXXI) is reacted with an appropriately selected and suitably substituted isocyanate of formula (XXXII), wherein $R^{2A}$ is selected from aryl, aralkyl, heterocyclyl, heterocyclyl-alkyl, diarylalkyl, tri-halomethyl, arylamino or lower alkyl, or a sulfonyl chloride of formula (XXXIII) or a carbonyl chloride of formula (XXXIV), or an anhydride of formula (XXXXVII) in an organic solvent such as DCM, toluene, and the like, to produce the corresponding compound of formula (Id). When the compound of formula (XXXI) is reacted with a sulfonyl chloride of formula (XXXIII) or a carbonyl chloride of formula (XXXIV), the reaction is carried out with further addition of an organic base such as TEA, DIPEA, and the like.

Compounds of formula (I) wherein A is a substituted alkyl may alternatively be prepared according to the process outlined in Scheme 6.

SCHEME 6

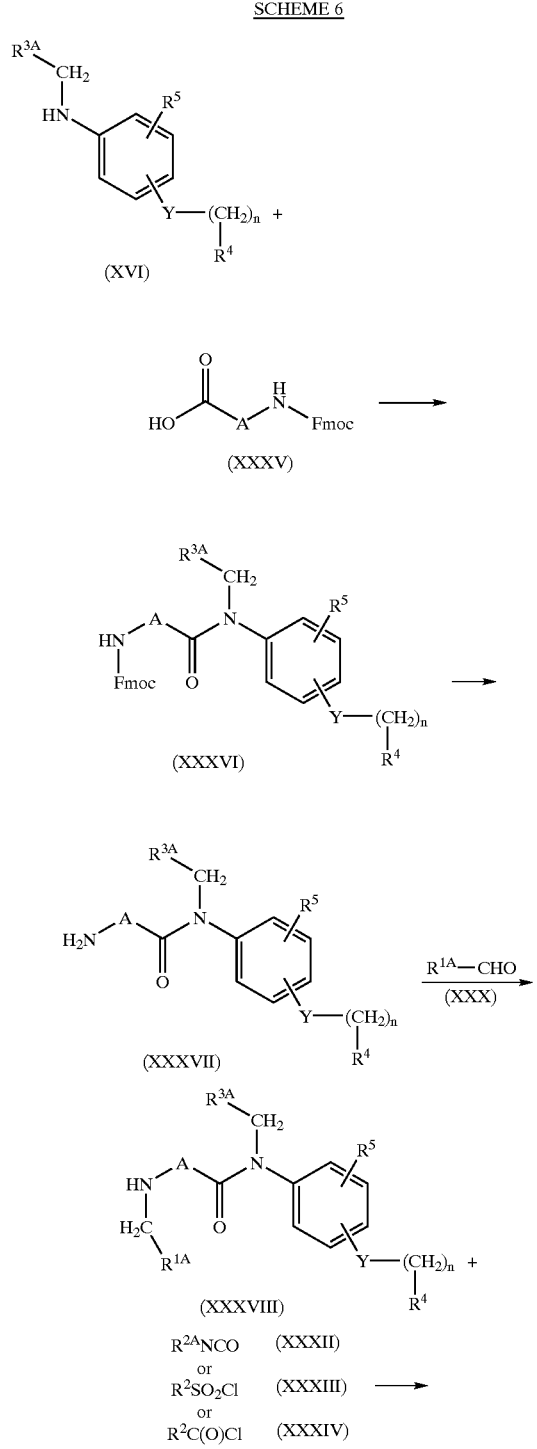

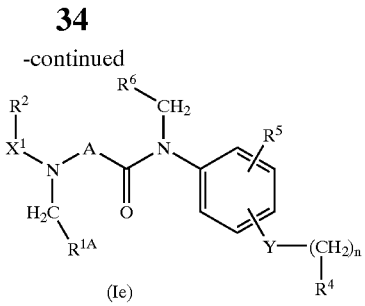

(Ie)

More specifically, a suitably substituted compound of formula (XVI), prepared as described in Scheme 2 above, is coupled with an appropriately selected, Fmoc protected compound of formula (XXXV), in an organic solvent such as DCM, DMF, and the like, to produce the corresponding compound of formula (XXXVI).

The compound of formula (XXXVI) is deprotected by removal of the Fmoc protecting group by known methods [for example by treating with piperidine in DMF], to produce the corresponding compound of formula (XXXVII).

The compound of formula (XXXVII) is reacted with a suitably substituted aldehyde of formula (XXX), wherein $R^{1A}$ is as previously defined, in the presence of a reducing agent such as sodium cyanoborohydride, and the like, under dehydrating conditions, for example in an acid alcohol solution such as acidic methanol or in a solution of titanium tetraisopropoxide in DCM, followed by addition of methanol and sodium cyanoborohydride, to produce the corresponding compound of formula (XXXVIII).

The compound of formula (XXXVIII) is coupled with an appropriately selected and suitably substituted isocyanate of formula (XXXII), wherein $R^{2A}$ is as previously defined, sulfonyl chloride of formula (XXXIII) or carbonyl chloride of formula (XXXIV), in an organic solvent such as DCM, and the like, in the presence of an organic base such as TEA, DIEA, and the like, to produce the corresponding compound of formula (Ie).

Optionally, the compound of formula (XXXVIII) may be further reacted with a second equivalent of the compound of formula (XXX) to yield a derivative of the compound of formula (XXXVIII), wherein the leftmost amine nitrogen is di-substituted with the —$CH_2$—$R^{1A}$ group, wherein $R^{1A}$ is as previously defined.

Compounds of formula (I), particularly those wherein $X^1$ and $X^3$ are each absent, $X^2$ is carbonyl and $X^4$ is carbonyl or sulfonyl may be prepared according to the process outlined in Scheme 7. This process is particularly preferred for preparation of compounds of formula (I) wherein A is contains a non-hydrogen substituent alpha to the right-hand most amine nitrogen.

SCHEME 7

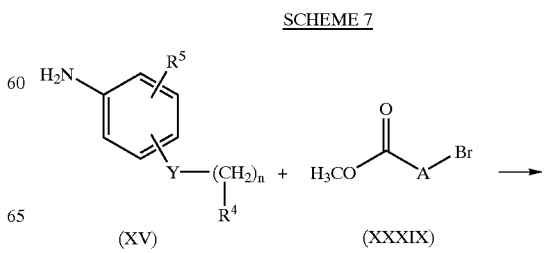

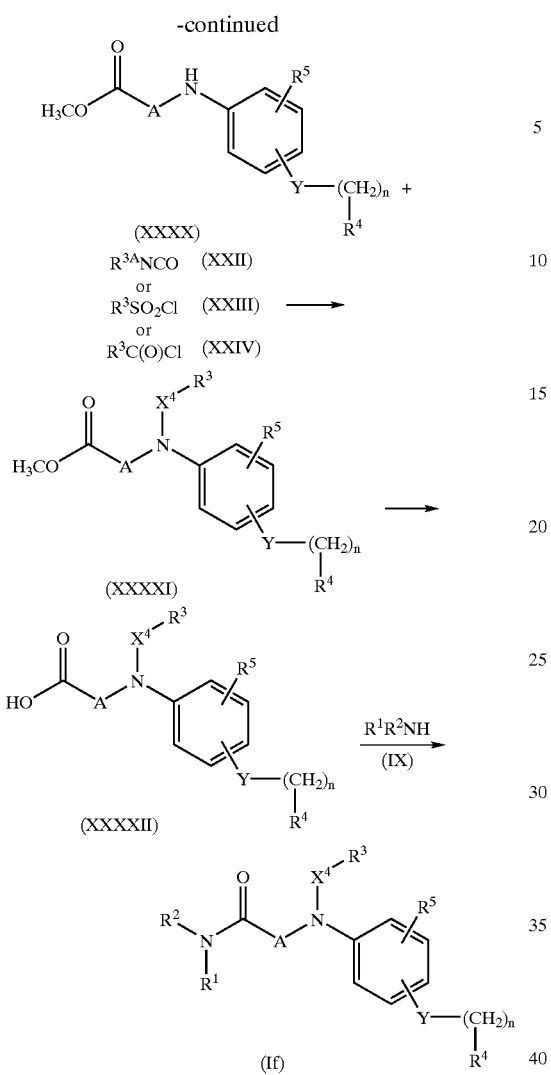

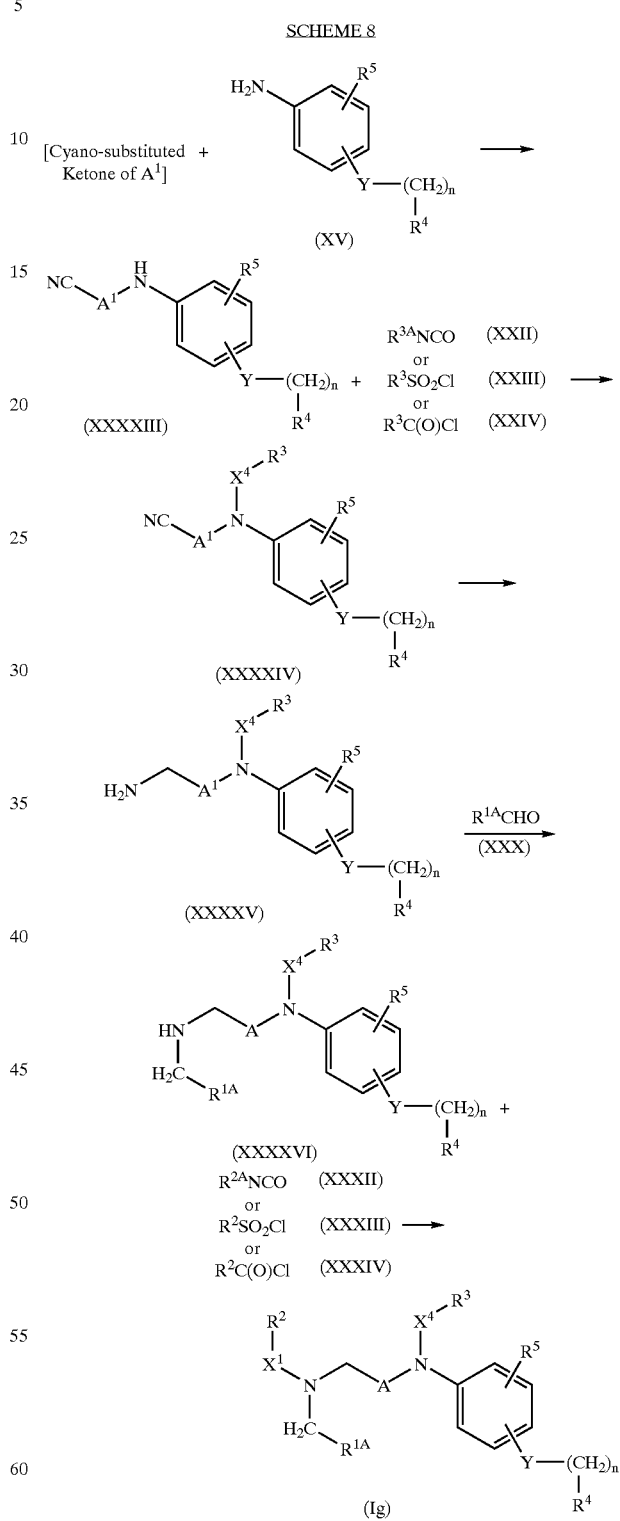

Compounds of formula (I), particularly those wherein $X^1$ and $X^4$ are each carbonyl or sulfonyl and $X^2$ and $X^3$ are each absent may be prepared according to the process outlined in Scheme 8

Accordingly, a suitably substituted compound of formula (XV), prepared as in Scheme 2 above, is alkylated with an appropriately selected compound of formula (XXXIX), ins an organic solvent such as DCM, chloroform, and the like, to produce the corresponding compound of formula (XXXX).

The compound of formula (XXXX) is coupled with an appropriately selected and suitably substituted isocyanate of formula (XXII), wherein $R^{3A}$ is as previously defined, sulfonyl chloride of formula (XXIII) or carbonyl chloride of formula (XXIV), in an organic solvent such as DCM, and the like, to produce the corresponding compound of formula (XXXXI). When the compound of formula (XXXX) is reacted with a sulfonyl chloride of formula (XXXIII) or a carbonyl chloride of formula (XXXIV), the reaction is run in the presence of an organic base such as TEA, DIEA, and the like.

The compound of formula (XXXXI) is subjected to hydrolysis of the methyl ester, in the presence of an inorganic base such as sodium hydroxide, and the like, to produce the corresponding compound of formula (XXXXII).

The compound of formula (XXXXII) is coupled with a suitably substituted amine of formula (IX), in the presence of a coupling agent such as PyBOP, and the like, in an organic solvent such as DCM, and the like, to produce the corresponding compound of formula (If).

Accordingly, wherein $A^1$ is an oxo and cyano substituted cycloalkyl, an oxo and cyano substituted cycloalkenyl, an oxo and cyano substituted cycloalkyl-alkyl, an oxo-alkyl and cyano substituted aryl or an oxo-alkyl and cyano-alkyl substituted aryl-alkyl, a known compound or compound prepared by known methods, is reacted with a compound of formula (XV), prepared as outlined in Scheme 2, in the presence of a reducing agent such as sodium cyanoborohydride, and the like, under dehydrating conditions, for example in an acid alcohol solution such as acidic methanol, to produce the corresponding compound of formula (XXXXIII).

The compound of formula (XXXXIII) is reacted with an appropriately selected and suitably substituted isocyanate of formula (XXII), wherein $R^{3A}$ is as previously defined, sulfonyl chloride of formula (XXIII) or carbonyl chloride of formula (XXIV), in an organic solvent such as DCM, and the like, to produce the corresponding compound of formula (XXXXIV). When the compound of formula (XXXXIII) is reacted with a sulfonyl chloride of formula (XXIII) or a carbonyl chloride of formula (XXIV), the reaction is run in the presence of an organic base such as TEA, DIEA, and the like.

The cyano functional group on the compound of formula (XXXXIV) is reduced by known methods, for example by treatment with lithium aluminum hydride, in an organic solvent such as THF, and the like, to produce the corresponding compound of formula (XXXXV).

The compound of formula (XXXXV) is reacted with a suitably substituted aldehyde of formula (XXX), wherein $R^{1A}$ is as previously defined, in the presence of a reducing agent such as sodium cyanoborohydride, and the like, under dehydrating conditions, for example in an acid alcohol solution such as acidic methanol or in a solution of titanium tetraisopropoxide in DCM, followed by addition of methanol and sodium cyanoborohydride, to produce the corresponding compound of formula (XXXXVI).

The compound of formula (XXXXVI) is reacted with an appropriately selected and suitably substituted isocyanate of formula (XXXII), wherein $R^{2A}$ is as previously defined, sulfonyl chloride of formula (XXXIII), or carbonyl chloride of formula (XXXIV), in an organic solvent such as DCM, and the like, to produce the corresponding compound of formula (Ig). When the compound of formula (XXXXVI) is reacted with a sulfonyl chloride of formula (XXXIII) or a carbonyl chloride of formula (XXXIV), the reaction is run in the presence of an organic base such as TEA, DIEA, and the like.

Compounds of formula (I) wherein $R^1$, $X^1$ and $R^2$ are taken together (with the amine nitrogen) to form an oxo substituted heterocyclyl group, may be prepared according to the process outlined in Scheme 9.

SCHEME 9

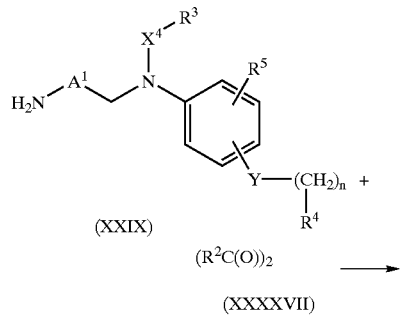

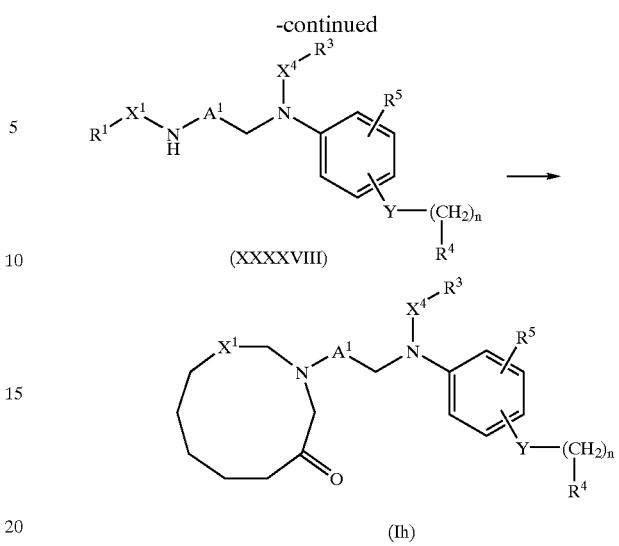

More particularly, the compound of formula (XXIX), prepared as in Scheme 5, is reacted with a suitably substituted symmetric or asymmetric anhydride, a compound of formula (XXXXVII), preferably a symmetric anhydride, in an organic solvent such as toluene, DCM, and the like, to yield the corresponding compound of formula (XXXXVIII).

The compound of formula (XXXXVIII) is heated at an elevated temperature in the range of about 40–180° C., or treated with addition of an anhydride such as acetic anhydride, trifluoroacetic anhydride, and the like, in an organic solvent such as methylene chloride, toluene, 1,2-dichlorobenzene, and the like, to yield the corresponding compound of formula (Ih), wherein

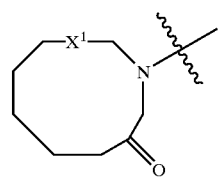

represents the group wherein $R^1$, $R^2$ and $X^1$ are taken together (with the amine nitrogen) to form a cyclic oxo substituted heterocyclyl.

Wherein the compound of formula (XXXXVII) is an asymmetric anhydride, (a compound of the formula $R^{2\prime}$—C(O)—C(O)—$R^{2\prime\prime}$, wherein $R^{2\prime}$ and $R^{2\prime\prime}$ are different), the $R^2$ group which is coupled onto the compound of formula (XXIX) may be readily determined by one skilled in the art, based on the relative reactivities of the carbonyl groups adjacent to the $R^{2\prime}$ and $R^{2\prime\prime}$ groups.

It is generally preferred that the respective product of each process step be separated from other components of the reaction mixture and subjected to purification before its use as a starting material in a subsequent step. Separation techniques typically include evaporation, extraction, precipitation and filtration. Purification techniques typically include column chromatography (Still, W. C. et. al., *J. Org. Chem.* 1978, 43, 2921), thin-layer chromatography, HPLC, acid-base extraction, crystallization and distillation.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved by enzymatic resolution or by using a chiral HPLC column.

To prepare the pharmaceutical compositions of this invention, one or more compounds or salts thereof, as the active ingredient, is intimately admixed with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed. Thus for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will preferably contain per dosage unit, e.g., tablet, capsule, powder, injection, teaspoonful and the like, from about 5 to about 500 mg of the active ingredient, although other unit dosages may be employed.

In therapeutic use for treating disorders of the gastrointestinal system in mammals, the compounds of this invention may be administered in an amount of from about 0.5 to 100 mg/kg 1–2 times per day orally. In addition the compounds may be administered via injection at 0.1–10 mg/kg per day. Determination of optimum dosages for a particular situation is within the capabilities of formulators.

In order to illustrate the invention, the following examples are included. These examples do not limit the invention. They are meant to illustrate and suggest a method of practicing the invention. Although there are other methods of practicing this invention, those methods are deemed to be within the scope of this invention.

EXAMPLE 1

N-trityl-cis-3-aminocyclohexanecarboxylic acid

Adapting the method of K. Barlos, D. Papaioannou and D. Theodoropoulos, JOC, 1982, 47, 1324–1326, cis-3-aminocyclohexanecarboxylic acid was protected as the N-trityl derivative.

TMSCI (26.1 ml, 0.205 mmol) was added to a suspension of cis-3-aminocyclohexanecarboxylic acid (29.4 g, 0.205 mmol) suspended in a 5:1 solution of $CH_2Cl_2$—$CH_3CN$ (500 ml) at room temperature. The mixture was heated at reflux for 2 hours and then allowed to cool to ambient temperature. TEA (57.2 ml, 0.410 mmol) was added dropwise to the mixture, followed immediately by portionwise addition of triphenylmethyl chloride (57.2 g, 0.205 mmol). After stirring for 18 h, MeOH was added to the mixture to give a homogeneous solution. The mixture was evaporated down to dryness and the resultant residue partitioned between $Et_2O$ and 10% citric acid (1:1, 800 ml total). The ether layer was collected and combined with an ether extraction (150 ml) of the citric acid layer. The combined ether fractions were then extracted with 2 M NaOH (3×250 ml) and water (1×100 ml). The aqueous layers were washed with ether (2×150 ml). After cooling to 0° C., the aqueous layer was acidified to pH 7 with concentrated HCl and extracted with ethyl acetate (3×200 ml). The combined extracts were dried over $MgSO_4$ and evaporated down to give a white foam, 67.4 g, 85% yield.

MS 384 (M⁻)

$^1$H NMR (CDCl$_3$) δ 0.44–0.95 (br m, 3H), 0.97–1.22 (br m, 2H), 1.30–1.48 (br m, 1H), 1.53–1.79 (br m, 2H), 1.8–2.04 (br m, 1H), 2.10–2.29 (br m, 1H), 6.95–7.24 (m, 9H), 7.36–7.59 (m, 6H).

EXAMPLE 2

1-(2-(3-nitrophenoxy)ethyl)pyrrolidine

Following the procedure disclosed in GB 924961; 1959; Chem. Abstr.; 59; 9883b; 1963.

3-nitrophenol (3.29 g, 23.7 mmol) in DMF (20 ml) was added dropwise to 60% NaH (2.65 g, 66.2 mmol) in 30 ml DMF at 0° C., under nitrogen. The reaction was stirred until $H_2$(g) evolution ceased. 1-(2-chloroethyl)pyrrolidine hydrochloride (5.63 g, 33.1 mmol) was then added portionwise. The mixture was stirred at room temperature for 18 h. The reaction mixture was quenched with 2N NaOH (50 ml) and the desired product extracted into ether (3×50 ml). The combined ether layers were washed (2×50 ml) with water, dried over $MgSO_4$, and evaporated to dryness in vacuo. The residue was purified through a silica gel plug using 10% ethyl acetate/hexane to remove the impurities and then the desired product was eluted off with 40% ethyl acetate/hexane containing 2% $Et_3N$ to yield a pale yellow oil.

MS 237 (MH⁺)

$^1$H NMR (CDCl$_3$) δ 1.78–1.88 (m, 4H), 2.55–2.66 (m, 4H), 2.94 (t, J=5.8 Hz, 2H), 4.18 (t, J=5.8 Hz, 2H), 7.23–7.28 (m, 1H), 7.42 (virtual t, J=8.2 Hz, 1H), 7.75–7.76 (m, 1H), 7.80–7.83 (m, 1H).

EXAMPLE 2B 2-(2-(3-aminophenoxy)ethyl)-1-methylpyrrolidine 3-aminophenol (0.74 g, 6.8 mmol) in DMF (10 ml) was added dropwise to 95% NaH (0.49 g, 20.4 mmol) in 10 ml DMF at 0° C., under nitrogen. The reaction was stirred until H$_2$(g) evolution ceased. 2-(2-chloroethyl)-1-methylpyrrolidine hydrochloride (1.25 g, 6.8 mmol) was then added portionwise. The mixture was stirred at room temperature for 18 h. The reaction mixture was quenched with 1N NaOH (50 ml) and the desired product extracted into ether (3×50 ml). The combined ether layers were washed (2×50 ml) with water, dried over MgSO$_4$, and evaporated to dryness in vacuo. The residue was purified on silica gel by flash chromatography using 2% TEA in ethyl acetate to give an oil.

MS 221 (MH$^+$)

$^1$H NMR (CDCl$_3$) δ 1.46–2.31 (m, 8H), 2.34 (s, 3H), 3.08 (ddd, J=8.3, 7.6, 2.4 Hz, 1H), 3.64 (br s, 2H), 3.89–4.08 (m, 2H), 6.20–6.36 (m, 3H), 7.04 (t, J=8.0 Hz, 1H).

EXAMPLE 2C 1-(2-(3-aminophenoxy)ethyl)piperidine

Following the procedure as described in Example 2B, 19.9 g (0.182 mol) of 3-aminophenol was converted into the title compound as a light yellow oil.

MS 221 (MH$^+$)

$^1$H NMR (CDCl$_3$) δ 1.38–1.50 (m, 2H), 1.52–1.66 (m, 4H), 2.43–2.56 (m, 4H), 2.75 (t, J=6.1 Hz, 2H), 3.65 (s br, 2H) 4.07 (t, J=6.1 Hz, 2H), 6.22–6.35 (m, 3H), 7.04 (t, J=7.9 Hz, 1H).

EXAMPLE 3

1-(2-(3-aminophenoxy)ethyl)pyrrolidine

A mixture of 1-(2-(3-nitrophenoxy)ethyl)pyrrolidine (3.49 g, 14.8 mmol), 10% palladium on carbon (400 mg) and ethyl acetate (20 ml) was reduced under 50 psi hydrogen for 10 h. The reaction mixture was filtered through Celite 545 and the product extracted into 1M HCl (3×20 ml). The acidic layer was washed with ether (2×20 ml) and then the pH adjusted to >10 with 2M NaOH. The aqueous layer was extracted with ether (3×20 ml), dried over MgSO$_4$ and concentrated in vacuo. The product was eluted through a silica gel pad (75% ethyl acetate/hexane/1% Et$_3$N) to yield the product as a pale yellow oil.

MS 207 (MH$^+$)

$^1$H NMR (CDCl$_3$) δ 1.72–1.80 (m, 2H), 2.54–2.71 (m, 2H), 2.88 (t, J=8.2 Hz, 2H), 3.48–3.79 (br s, 2H), 4.07 (t, J=8.2Hz, 2H), 6.22–6.39 (m, 3H), 7.05 (virtual t, J=9.1 Hz,1H).

EXAMPLE 4

N-(3-(2-(1-pyrrolidino)ethyloxy)phenyl)-cis-3-(triphenylmethylamino)cyclohexylcarboxamide Benzotriazole-1-yl-oxy-tris-pyrrolidino-phosphonium hexafluorophosphate (PyBop) (4.8 g, 9.3 mmol) was added to a mixture of N-trityl-cis-3-aminocyclohexanecarboxylic acid (3.3 g, 8.4 mmol), 1-(2-(3-aminophenoxy)ethyl)pyrrolidine (1.4 g, 7.0 mmol), DIEA (1.6 ml, 9.3 mmol) and dichloromethane (30 ml). After stirring overnight, the crude mixture was evaporated onto silica gel and purified by flash chromatography (20% EtOAc/2% Et$_3$N/hexane, then 60% EtOAc/2% Et$_3$N/hexane). The title compound was isolated as a white foam upon evaporation.

Yield: 3.2 g, 78%

MS 596 (MNa$^+$), 574 (MH$^+$), 332 (MH$^+$-trt), 243 (trt$^+$).

EXAMPLE 5

N-(3-(2-(1-pyrrolidino)ethyloxy)phenyl)-N-cis-3-(triphenylmethylamino)cyclohexylmethylamine LAH (220 mg, 5.8 mmol) was added to N-(3-(2-(1-pyrrolidino)ethyloxy)phenyl)-cis-(3-(triphenylmethyl)amino)cyclohexylmethylcarboxamide (2.1 g, 3.7 mmol) in THF (10 ml) under nitrogen at ambient temperature. The reaction was refluxed for 8 h, cooled to room temperature and quenched with a saturated solution of Rochelle's salt (potassium sodium tartrate). The precipitate was filtered away through Celite 545 leaving the crude product as an oil upon evaporation. The residue was dissolved in EtOAc (20 ml), washed with water (2×20 ml) and dried over MgSO$_4$. Evaporation of the solvent yielded the product as a white foam.

MS 582 (MNa$^+$), 560 (MH$^+$), 318 (MH$^+$-trt), 243 (trt$^+$).

EXAMPLE 6

N-(3-(2-(1-pyrrolidino)ethyloxy)phenyl)-N-[cis-3-(triphenylmethylamino)cyclohexylmethyl]-4-fluorophenylcarboxamide 4-fluorobenzoyl chloride (0.34 ml, 2.9 mmol) in dichloromethane (5 ml) was added dropwise to a solution of N-(3-(2-(1-pyrrolidino)ethyloxy)phenyl)-N-cis-3-(triphenylmethylamino)cyclohexylmethylamine (1.4 g, 2.6 mmol), triethylamine (0.40 ml, 2.9 mmol) and dichloromethane (10 ml). After 3 h the reaction was quenched with 2M NaOH (3 ml) and extracted with DCM (3×20 ml). The organic layers were combined, dried over MgSO$_4$ and evaporated onto silica gel in vacuo. The product was purified by chromatography on a silica gel column, preconditioned with Et$_3$N, using 50% EtOAc/2% Et$_3$N/hexane. The product was isolated as a white foam.

MS 682 (MH$^+$), 440 (MH$^+$-trt), 243 (trt$^+$).

EXAMPLE 7

N-(3-(2-(1-pyrrolidino)ethyloxy)phenyl)-N-[cis-(3-aminocyclohexyl)methyl]-4-fluorophenylcarboxamide 10% TFA/1% triethylsilane/DCM (35 ml) was added to N-(3-(2-(1-pyrrolidino)ethyloxy)phenyl)-N-[cis-3-(triphenylmethylamino)cyclohexylmethyl]-4-fluorophenylcarboxamide (1.75 g, 2.57 mmol). Upon completion, after 3 h, the desired product was extracted into 1 M HCl (3×20 ml). The extracts were washed with DCM (2×20 ml) and the aqueous layer (cooled to 0 C) made basic with NaOH. Extraction of the aqueous layer with EtOAc (3×20 ml) yielded, upon drying (MgSO$_4$) and evaporation, the product as a pale yellow oil.

MS 462 (MNa$^+$), 440 (MH$^+$).

EXAMPLE 8

(#214)

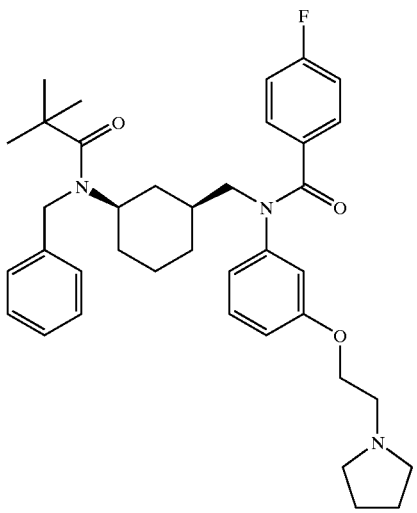

To a stirred solution of N-(3-(2-(1-pyrrolidino)ethyloxy)phenyl)-N-(cis-3-amino-cyclohexyl)methyl-4-fluorophenylcarboxamide (1.0 g, 2.3 mmol) and benzaldehyde (0.26 ml, 2.5 mmol) in toluene (4 ml) was added titanium(IV) isopropoxide (0.82 ml, 2.8 mmol) under nitrogen. After 18 h, EtOH (0.8 ml) was added followed by portionwise addition of sodium triacetoxyborohydride (0.63 g, 2.8 mmol). After an additional 4 h of stirring, the reaction was quenched with 2M NaOH. The precipitate was filtered off through Celite 545, then dried over MgSO$_4$ and evaporated in vacuo to yield crude N-(3-(2-(1-pyrrolidino)ethyloxy)phenyl)-N-(cis-3-(benzylamino)cyclohexyl)methyl-4-fluorophenylcarboxamide.

The crude residue (1.2 g) was taken up in DCM (4 ml), followed by addition of trimethylacetyl chloride (0.31 ml, 2.5 mmol). The reaction was complete in less than 2 h. The reaction was neutralized with a saturated solution of NaHCO$_3$, extracted with DCM (3×10 ml), dried over MgSO$_4$ and evaporated onto silica gel. The product was purified by flash chromatography (50% EtOAc/1% Et$_3$N/hexane) to yield a white foam (690 mg). Addition of 1M HCl (1.2 ml, 1.2 mmol) in ether to the free base in ether (5 ml) yielded the product.

MS 614 (MH$^+$); HPLC (RT 4.11 min.)

EXAMPLE 9

N-(3-(2-(1-pyrrolidino)ethyloxy)phenyl)-N-(cis-3-(triphenylmethylamino)cyclohexyl)methyl-N'-phenylurea Phenylisocyanate (0.31 ml, 2.9 mmol) was added dropwise to a solution of N-(3-(2-(1-pyrrolidino)ethyloxy)phenyl)-N-(cis-3-(triphenylmethylamino)-cyclohexyl)methylamine (1.4 g, 2.6 mmol) in dichloromethane (5 ml). After stirring for 18 h, the reaction mixture was evaporated onto silica gel. The title product was isolated by chromatography (50% EtOAc/hexane, then 60% EtOAc/2% Et$_3$N/hexane) as a white foam.

MS 679 (MH$^+$), 437 (MH$^+$-trt), 243 (trt$^+$).

EXAMPLE 10

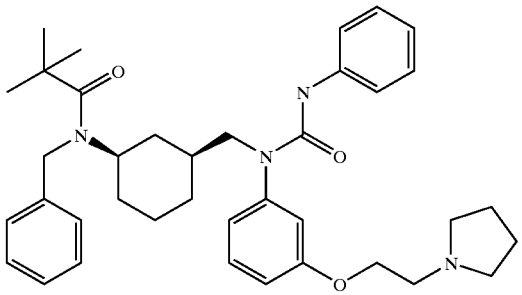

By the method of example 7 and 8, N-(3-(2-(1-pyrrolidino)ethyloxy)phenyl)-N-(cis-3-(triphenylmethyl)aminocyclohexyl)methyl-N'-phenylurea, benzaldehyde and trimethylacetyl chloride were reacted to yield the title compound.

MS 437 (MH$^+$).

EXAMPLE 11

N-(3-(2-(4-morpholino)ethyloxy)phenyl)-N-[(cis-3-(3-nitrobenzyl)aminocyclohexylmethyl]-4-fluorophenylcarboxamide To a stirred solution of N-(3-(2-(4-morpholino)ethyloxy)phenyl)-N-(cis-3-aminocyclohexyl)methyl-4-fluorophenylcarboxamide (5.3 g, 12 mmol) and 3-nitrobenzaldehyde (2.0 g, 13 mmol) in DCM (30 ml) was added titanium(IV) isopropoxide (4.6 ml, 16 mmol) under nitrogen. After 3 h, EtOH (20 ml) was added followed by portionwise addition of sodium cyanoborohydride (1.0 g, 16 mmol). The reaction was stirred overnight, then quenched with 2M NaOH. The resulting precipitate was filtered off through Celite 545, the filtrate was dried over MgSO$_4$ and evaporated in vacuo to yield crude product.

MS 591 (MH+).

EXAMPLE 12

(#93)

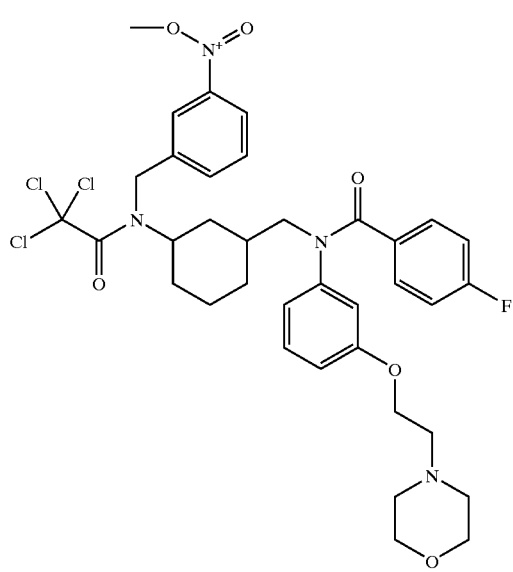

Trichloroacetyl chloride (0.93 ml, 8.3 mmol) was added to crude N-(3-(2-(4-morpholino)ethyloxy)phenyl)-N-[(cis-3-(3-nitrobenzyl)aminocyclohexylmethyl]-4-fluorophenylcarboxamide (4.9 g, 8.3 mmol) taken up in DCM (20 ml). The reaction was complete in less than 2 h. The reaction was neutralized with a saturated solution of NaHCO$_3$, extracted into DCM (3×15 ml), dried over MgSO$_4$ and evaporated onto silica gel. The product was purified by chromatography (50% EtOAc/2% Et$_3$N/hexane) to yield the title compound as a white foam.

MS 736 (MH$^+$); HPLC (RT 4.11 min.).

EXAMPLE 13

N-(3-(2-(4-morpholino)ethyloxy)phenyl)-N-{(cis3-(benzylamino)cyclohexyl)methyl}-N'-phenylurea By the method of example 11, N-(3-(2-(4-morpholino)ethyloxy)phenyl)-N-(cis-3-aminocyclohexyl)methyl-N'-phenylurea and benzaldehyde were converted into the title compound.

MS 543 (MH$^+$).

EXAMPLE 14

(#40)

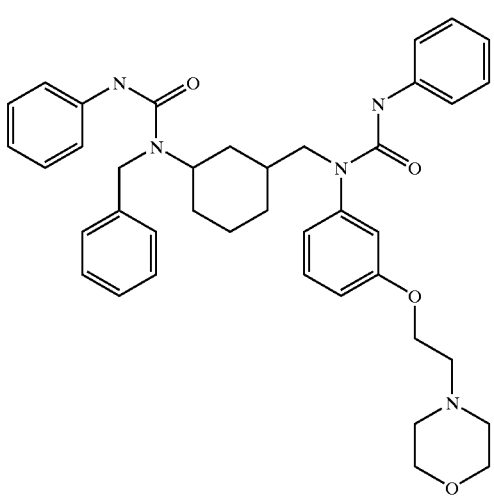

By the method of example 9, N-(3-(2-(4-morpholino)ethyloxy)phenyl)-N-{(cis-3-(benzylamino)cyclohexyl)methyl}-N'-phenylurea and phenylisocyanate were converted into the title compound.

MS 662 (MH$^+$); HPLC (RT 4.38 min.).

EXAMPLE 15

(#57)

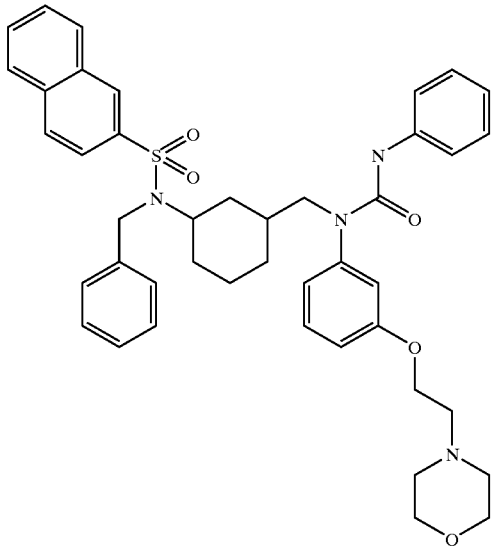

By the method of example 12, N-(3-(2-(4-morpholino)ethyloxy)phenyl)-N-{(cis-3-(benzylamino)cyclohexyl)methyl}-N'-phenylurea and 2-naphthalenesulfonyl chloride were converted into the title compound.

MS 733 (MH$^+$); HPLC (RT 4.97 min.).

EXAMPLE 16

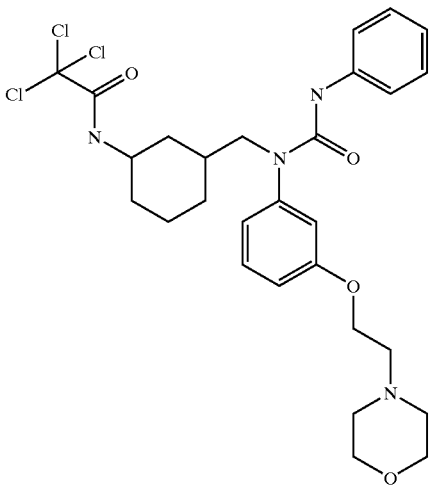

(#72)

By the method of example 12, N-{3-(2-(4-morpholino)ethyloxy)phenyl)-N-cis-3-(aminocyclohexyl)methyl}-N'-phenylurea and trichloroacetyl chloride were converted into the title compound.

MS 599 (MH+); HPLC (RT 3.59 min.).

EXAMPLE 17

1-(2-(3-amino-2-methylphenoxy)ethyl)pyrrolidine

By the method of examples 2 and 3, 1-(2-chloroethyl)pyrrolidine hydrochloride and 2-methyl-3-nitrophenol were converted into the title compound.

MS 221 (MH+)

$^1$H NMR (CDCl$_3$) δ 1.75–1.86 (m, 4H), 2.05 (s, 3H), 2.62–2.67 (m, 4H), 2.92 (t, J=6.0 Hz, 2H), 3.60 (br s, 2H), 4.09 (t, J=6.0 Hz, 2H), 6.33 (virtual d, J=8.1 Hz, 2H), 6.95 (virtual t, J=9.1 Hz, 1H).

EXAMPLE 18

4-(2-(3-aminophenoxy)ethyl)morpholine

By the method of examples 2 and 3, 4-(2-chloroethyl)morpholine hydrochloride and 3-nitrophenol were converted into the title compound.

MS 223 (MH+)

EXAMPLE 19

N-(4-fluorophenylmethyl)-4-(2-(3-aminophenoxy)ethyl)morpholine 4-fluorobenzaldehyde (1.3 ml, 12 mmol) was added to a stirred solution of 4-(2-(3-aminophenoxy)ethyl)morpholine (2.2 g, 10 mmol) in 2% AcOH/MeOH (40 ml). After 1 h, sodium cyanoborohydride (0.50 g, 12 mmol) was added portionwise to the mixture. After an additional 2 h, 2M NaOH (20 ml) was added and the mixture evaporated to give a tan residue. The residue was partitioned between 1N HCl and ether. The acid layer was washed 2×40 ml with ether and then adjusted to a pH>10 with NaOH. The product was extracted into ethyl acetate (3×50 ml), dried over magnesium sulfate and evaporated down to yield the title compound as a brown oil.

MS 331 (MH+)

$^1$H NMR (CDCl$_3$) δ 2.50–2.65 (m, 4H), 2.76 (t, J=5.8 Hz, 2H), 3.68–3.82 (m, 4H), 4.01–4.16 (m, 3H), 4.29 (d, J=5.3 Hz, 2H), 6.18 (s, 1H), 6.22–6.33 (m, 2H), 6.97–7.13 (m, 3H), 7.29–7.40 (m, 2H).

EXAMPLE 20

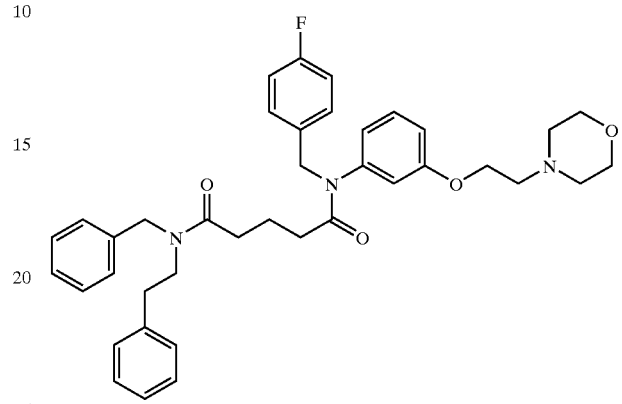

(#129)

N-(4-fluorophenylmethyl)-4-(2-(3-amino-phenoxy)ethyl)morpholine (260 mg, 0.79 mmol) and glutaric anhydride (95 mg, 0.79 mmol) were combined and refluxed in chloroform (3 ml) overnight. To the organic solution at ambient temperature was added, N-benzylphenethylamine (170 mg, 0.79 mmol), DIEA (0.28 ml, 1.6 mmol) and PyBOP (420 mg, 0.80 mmol). The sample was concentrated down upon completion (<3 h). Chromatography on silica gel with 1% MeOH in ethyl acetate provided the title compound.

MS 638 (MH+); HPLC (RT 4.32 min.)

$^1$H NMR (CDCl$_3$) (approximately 1:1 mixture of rotomers) δ 1.85–2.01 (m, 2H), 2.08–2.22 (m, 2H), 2.26–2.43 (m, 2H), 2.78 (t, J=7.4 Hz, 2H), 2.9–3.13 (m, 2H), 3.32–3.74 (m, 6H), 3.88–4.05 (m, 4H), 4.24–4.42 (m, 3H), 4.54 (s, 1H), 4.75–4.88 (m, 2H), 6.45 (s, 1H), 6.59 (t, J=6.2 Hz, 1H), 6.78–7.00 (m, 3H), 7.03–7.39 (m, 13H).

EXAMPLE 21

N-(3-nitrophenyl)methyl)phenethylamine

Sodium cyanoborohydride (0.18 g, 2.7 mmol) was added to a preformed imine of phenethylamine (0.28 g, 2.3 mmol) and 3-nitrobenzaldehyde (0.38 g, 2.5 mmol) in 2% AcOH-MeOH. The reaction was quenched after 4 h with a saturated solution of sodium bicarbonate and the solvent removed in vacuo. The resultant residue was partitioned between water and dichloromethane (20 ml total). The aqueous layer extracted with DCM (3×20 ml), the organic extracts were combined and dried over sodium sulfate. The crude material was used without further purification.

MS 257 (MH+).

EXAMPLE 22

N-(4-fluorophenyl)methyl)-N-[3-(2-(1-pyrrolidino)ethyloxy)-2-methylphenyl]-N'-(2-phenethyl)-1,5-pentyldiamide A solution of N-(4-fluorophenylmethyl)-1-(2-(3-amino-2-methylphenoxy)-ethyl)pyrrolidine (4.85 g, 14.8 mmol) and glutaric anhydride (2.02 g, 17.7 mmol) in toluene (30 ml)

was heated to reflux. After 12 h the reaction was concentrated in vacuo. PyBop (430 mg, 0.81 mmol)was added to the solution of crude N-(4-fluorophenylmethyl-N-3-(2-(1-pyrrolidino)ethyloxy)-2-methylphenylcarboxamidopentyric acid (330 mg, 0.74 mmol) and phenethylamine (90 mg, 0.74 mmol) in DMF (2 ml). The reaction mixture was stirred overnight, diluted with 2 M NaOH and then extracted with ether (3×20 ml). The combined extracts were washed with a brine solution and dried over MgSO$_4$. The crude material was purified by flash chromatography on silica gel using 80% ethyl acetate/2% Et$_3$N/hexane as eluent to yield the title compound as a brown oil.

MS 546 (MH$^+$).

EXAMPLE 23

(#215)

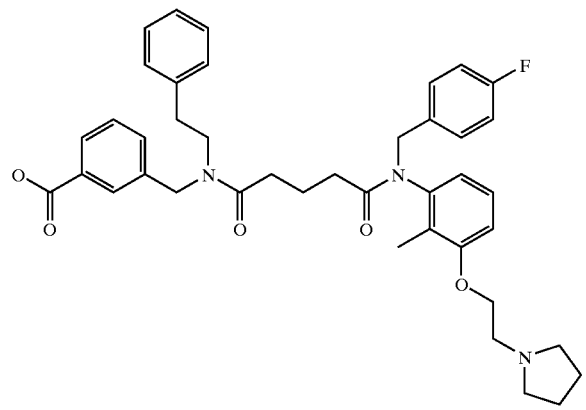

60% sodium hydride (~3 mg, 0.07 mmol) was added to N-(4-fluorophenyl)methyl)-N-[3-(2-(1-pyrrolidino)ethyloxy)-2-methylphenyl]-N'-(2-phenethyl)-1,5-pentyldiamide (30 mg, 0.06 mmol) in DMF (1 ml). After 10 min, methyl-3-(bromomethyl)benzoate (16 mg, 0.07 mmol) was added to the stirred solution. The reaction was quenched with sodium bicarbonate after 18 h and then extracted (3×15 ml) into ether. The title product was isolated by semi-prep HPLC (C-18 column, 30% CH$_3$CN/water/0.1% TFA to 60% CH$_3$CN/water/0.1% TFA). Note: the methyl ester was hydrolyzed under the acidic mobile phase conditions.

MS 680 (MH$^+$); HPLC (RT 3.53 min.)

EXAMPLE 24

N-(3-tert-butyldimethylsiloxyphenyl)4-fluorobenzylamine

By the method of example 19, 4-fluorobenzaldehyde (4.41 g, 35.5 mmol) and 3-aminophenol (3.60 g, 32.3 mmol) were reacted to yield a clear oil (6.75 g) upon silica gel purification (15% ethyl acetate/hexane).

MS 218 (MH+).

The resultant N-3-hydroxyphenyl-4-fluorobenzylamine (4.25 g, 19.6 mmol) and imidazole (1.33 g, 19.6 mmol) were combined in DMF (20 ml) and treated with tetrabutyldimethylsilyl chloride (3.05 g, 19.6 mmol). After 5 h, the reaction was diluted with saturated NaHCO$_3$ and extracted with ether. The ether layers were combined, washed with water and dried over MgSO$_4$. The title product was isolated by flash chromatography (15% EA/hexane) as a clear oil (3.75 g, 58%).

MS 332 (MH+)

$^1$H NMR (CDCl$_3$) δ 0.12 (s, 6H), 0.81 (s, 9H), 3.84 (br s, 1H), 4.12 (s, 2H), 5.96 (t, J=2.2 Hz, 1H), 6.10 (td, J=8.0, 2.2 Hz, 2H), 6.84–6.91 (m, 3H), 7.16–7.21 (m, 2H).

EXAMPLE 25

N-((4-fluorophenyl)methyl)-N-(3-hydroxyphenyl)-N'-(2-phenethyl)-N'-benzyl-1,5-pentyldiamide (#175)

N-(4-fluorophenyl)methyl)-N-(3-tert-butyldimethylsiloxyphenyl)-N'-(2-phenethyl)-N'-benzyl-1,5-pentyldiamide (4.2 g, 6.6 mmol), prepared by method of example 20, in THF (10 ml) was treated with 1 M TBAF (7.3 ml, 7.3 mmol). The reaction, complete in less than 15 h, was quenched with 0.1 M HCl. The aqueous layer was extracted with ethyl acetate (3×30 ml) and the organic layers dried over MgSO$_4$. The crude material was purified by flash chromatography using 50% ethyl acetate/hexane as eluent. The title compound was recovered as a clear oil.

MS 525 (MH$^+$)

$^1$H NMR (CDCl$_3$) (approximately 1:1 mixture of rotomers) δ 1.84–2.02 (m, 2H), 2.08–2.21 (m, 2H), 2.25 (t, J=7.3 Hz, 1H), 2.34 (t, J=7.3 Hz, 1H), 2.72–2.86 (m, 2H), 3.38–3.59 (m, 2H), 4.37 (s, 1H), 4.55 (s, 1H), 4.76 (s, 1H), 4.78 (s, 1H), 6.40 (t, J=7.7 Hz, 1H), 6.52 (m, 1H), 6.77–6.93 (m, 3H), 7.03–7.39 (m, 13H), 8.41 (s, 1H).

EXAMPLE 26

(#179)

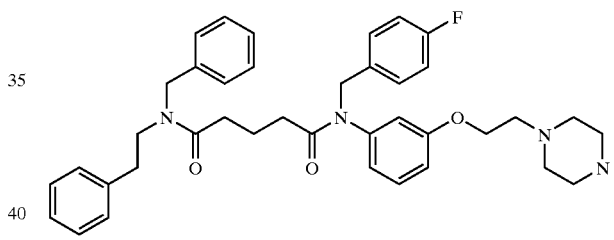

To N-(4-fluorophenyl)methyl)-N-(3-hydroxyphenyl)-N'-(2-phenethyl)-N'-benzyl-1,5-pentyldiamide (75 mg, 0.14 mmol) in THF (1 ml) was added 1-(2-hydroxyethyl)piperazine (22 mg, 0.17 mmol), tri-n-butylphosphine (0.14 ml, 0.57 mmol), and ADDP (86 mg, 0.34 mmol). After 18 h the reaction was diluted with a solution of saturated sodium bicarbonate and then extracted into ethyl acetate (3×15 ml). The combined organic layers were dried over MgSO$_4$ and evaporated down to an oil. The title product was isolated by semi-prep HPLC (C-18 column, 30% CH$_3$CN/water/0.1% TFA to 60% CH$_3$CN/water/0.1% TFA).

MS 637 (MH$^+$); HPLC (RT 3.34 min.).

EXAMPLE 27

N-[3-(2-(4-morpholino)ethoxy)phenyl]-N'-(2-phenethyl)-N'-benzyl-1,4-butyldiamide Applying the procedure used in Example 20, with substitution of 4-(2-(3-aminophenoxyethyl)morpholine and succinic anhydride for N-(4-fluorophenylmethyl)-4-(2-(3-aminophenoxy)ethyl)morpholine and glutaric anhydride respectively, yielded the title compound as a white solid.

MS 516 (MH$^+$)

EXAMPLE 28

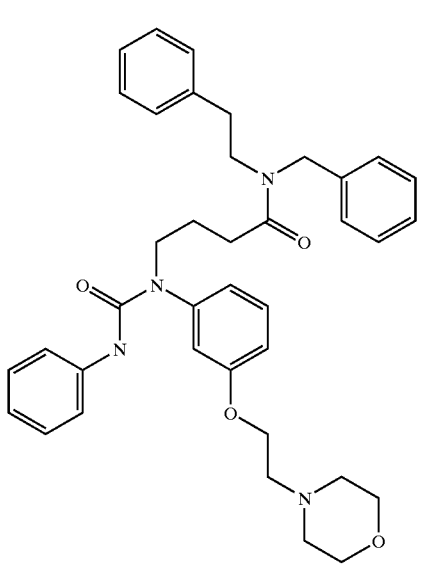

(#1)

N-[3-(2-(4-morpholino)ethoxy)phenyl]-N'-(2-phenethyl)-N'-benzyl-1,4-butyldiamide (0.39 g, 0.75 mmol) was dissolved in a solution of sodium borohydride (0.14 g, 3.8 mmol) in THF (4 mL). Acetic acid (0.22 ml, 3.75 mmol) was slowly added to the reaction mixture at 0° C. After 18 h, the reaction was quenched with 1N HCl, neutralized with saturated sodium bicarbonate and the THF layer collected. The organic layer was dried over $MgSO_4$, filtered and then treated with phenyl isocyanate (0.080 ml, 0.75 mmol) to yield crude solid product. The crude material was purified by flash chromatography using 50% ethyl acetate/hexane as eluent. The title compound was recovered as a clear oil.

MS 621 ($MH^+$);

$^1$H NMR ($CD_3OD$) (approximately 1:1 mixture of rotomers) δ 1.72–1.97 (m, 2H), 2.25 (t, J=6.8 Hz, 1H), 2.45 (t, J=6.8 Hz, 1H), 2.73–2.94 (m, 2H), 3.18–3.42 (m, 2H), 3.48–3.91 (m, 10H), 3.97–4.15 (m, 2H), 4.40 (t, J=4.9 Hz, 2H), 4.49 (s, 1H), 4.63 (s, 1H), 6.89–7.06 (m, 4H), 7.09–7.48 (m, 15H).

EXAMPLE 29

2,2-dimethylpropylbenzylamine

Step A: N-3-chlorobenzyltrimethylacetamide 3-chlorobenzylamine (3.54 g, 25 mmol) was added dropwise to trimethylacetyl chloride (2.65 ml, 21.5 mmol) and $Et_3N$ (3.5 ml, 25 mmol) in DCM (25 ml). After two hours, the reaction mixture was washed with 1 N HCl and the organic layer collected and dried over $MgSO_4$. N-3-chlorobenzyltrimethylacetamide was precipitated from DCM/hexane as a white solid, 3.95 g,

MS 192 ($MH^+$).

Step B:

N-benzyltrimethylacetamide (2.35 g, 12.3 mmol) in THF (10 ml) was refluxed with 1M borane-tetrahydrofuran (13.5 ml) for 15 hours. The reaction was quenched with 1N HCl, washed with ether, and the aqueous layer adjusted to a pH>10. The aqueous layer was extracted with EtOAc and the organic layers combined and dried over $MgSO_4$.

The title compound may be alternatively be prepared according to the procedure described in Overman, Larry E.; Burk, Robert M.; TELEAY; *Tetrahedron Lett.;* 25; 16; 1984; 1635–1638

EXAMPLE 30

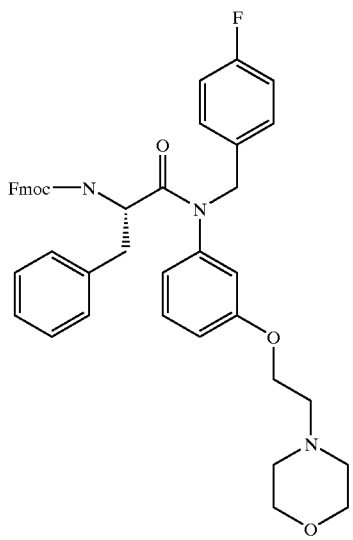

EDCl-MeI (0.33 g, 1.1 mmol) was added to N-(4-fluorophenylmethyl)-4-(2-(3-aminophenoxy)ethyl)morpholine (0.27 g, 0.83 mmol) (Prepared in Example 19), and Fmoc-L-Phe-OH (0.39 g, 1.0 mmol) in $CHCl_3$ (15 mL). After 8 h, the reaction was diluted with a saturated solution of $NaHCO_3$, extracted with DCM and dried over $MgSO_4$. The desired product was isolated by flash chromatography (50–100% EA/hexane) to yield a white solid.

MH+700.

EXAMPLE 31

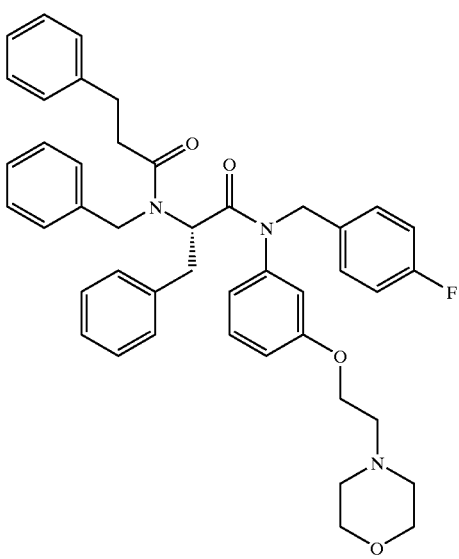

(#152)

The product prepared in Example 29, (31 mg, 0.044 mmol) was dissolved in DCM (1 mL) and deprotected with piperidine (7.4 µl, 0.082 mmol) to yield a white solid upon evaporation.

MH+478.

The crude product was then dissolved along with benzaldehyde (16 µl, 0.16 mmol) in 2% AcOH /MeOH (1 ml). To this solution was added NaBH₃CN (20 mg, 0.32 mmol) in two portions. After 1 h, the solvent was evaporated and the residue partitioned between 1N HCl and ether. The aqueous layer was washed with ether, adjusted to pH ~10 with 2N NaOH and extracted with DCM. The organic layer was dried over MgSO₄ and evaporated down. Hydrocinnamoyl chloride (12 µl, 0.08 mmol) was then added to the residue dissolved in DCM (2 ml) and DIEA (16 µl, 0.09 mmol). The title compound was isolated by semi-prep HPLC as the TFA salt.

MH+700; HPLC (RT 5.16 mins).

EXAMPLE 32

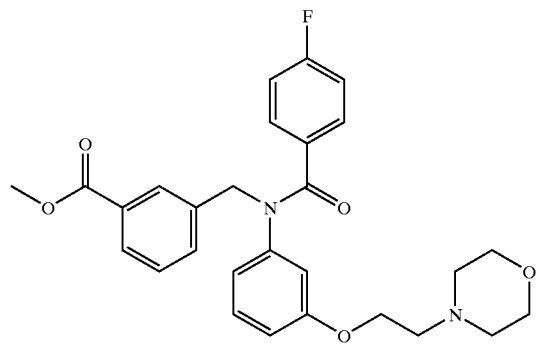

4-(2-(3-amino-phenoxy)ethyl)morpholine (389 mg, 1.75 mmol) and methyl 3-bromomethylbenzoate (482 mg, 2.1 mmol) were reacted in CHCl₃ (5 mL), that contained Et₃N (293 µl, 2.1 mmol). The reaction was refluxed for 16 h, until completion, as evidenced by disappearance of the starting aniline derivative on TLC (Rf 0.5 for product, ethyl acetate eluent)).

MS (MH+) 371

The reaction mixture was cooled and then treated with Et₃N (293 µl, 2.1 mmol) and 4-fluorobenzoyl chloride (207 µl, 1.75 mmol). Upon completion, the reaction mixture was quenched with 1N NaOH and extracted 3 times with DCM. The organic layer was dried over MgSO₄ and evaporated down onto silica gel. The title compound was isolated by flash chromatography (gradient from 80% EA/hexane to 100% EA) to yield a white solid.

MS (MH+) 493

EXAMPLE 33

(#138)

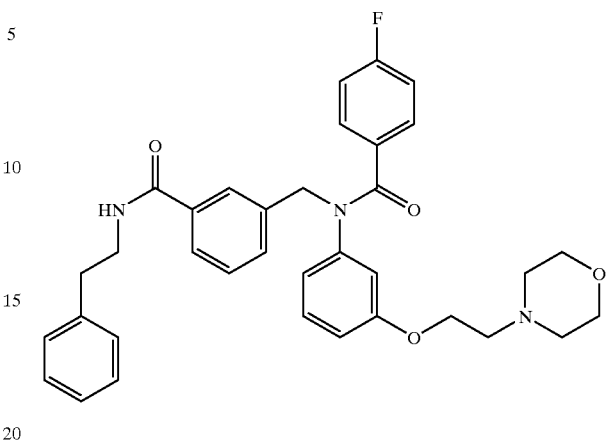

The compound prepared in Example 31 (375 mg, 0.82 mmol) was refluxed in a mixture of 10% NaOH/EtOH (30 ml). After 2 h, the EtOH was evaporated under vacuum. The residue was diluted with 2N NaOH and washed with ether. The aqueous layer was then acidified to pH 1 with concentrated HCl and extracted with DCM. The organic layer was dried over MgSO4 and evaporated down. The residue was dissolved in DCM (10 mL) and partitioned into ten aliquots. One aliquot was treated with phenethylamine (12 mg, 0.10 mmol) and EDCl-MeI (29 mg, 0.10 mmol). After 16 h, the reaction mixture was washed 2× with water and evaporated down to yield a brown residue. The title compound was isolated by semi-prep HPLC (reverse phase, C-18) as the TFA salt.

MH+582; HPLC (RT 3.41 mins).

EXAMPLE 34

N-3-cyanocyclopentyl-4-(2-(3-amino-phenoxy) ethyl)morpholine 4-(2-(3-aminophenoxy)ethyl)morpholine (2.15 g, 9.67 mmol) and 3-cyanocyclopentanone (1.06 g, 9.67 mmol) (prepared according to the process decsribed by Della, E.; Knill, A.; Aust. J. Chem.; 47; 10; 1994; 1833–1842) were combined in 1% AcOH/MeOH (50 ml). To this solution was added NaBH₃CN (925 mg, 14.5 mmol) in portions. After 12 h, the solvent was evaporated off and the residue partitioned between saturated NaHCO₃ and ethyl acetate. The aqueous layer was extracted with ethyl acetate, the combined organic layers were dried over MgSO₄ and evaporated down. The title compound was purified by flash chromatography with ethyl acetate as the eluent, 2.1 g

MS (MH+) 316.

EXAMPLE 35

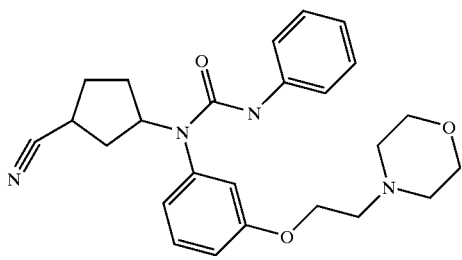

Phenylisocyanate (0.65 ml, 5.9 mmol) was added to N-3-cyanocyclopentyl4-(2-(3-amino-phenoxy)ethyl) morpholine (1.88 g, 5.95 mmol) partially dissolved in THF (25 ml) at room temperature. After 15 h, crude material was placed on a silica gel column and eluted with ethyl acetate to give 680 mg of a yellow oil.
MS (MH+) 435.

EXAMPLE 36

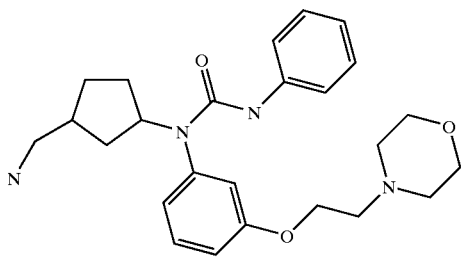

The product prepared in Example 34 (0.65 g, 1.5 mmol) dissolved in THF (10 ml) was added to 1M LAH (4.5 ml) at −78° C. and allowed to warm to room temperature. After 15 h, the reaction was quenched with a saturated solution of Rochelle's salt (potassium sodium tartrate). The precipitate was filtered away through Celite 545 to yield the crude product as an oil upon evaporation. The residue was dissolved in EtOAc, washed with water and dried over MgSO$_4$. Evaporation of the solvent yielded the product as an oil.
(MH+) 439

EXAMPLE 37

(#39)

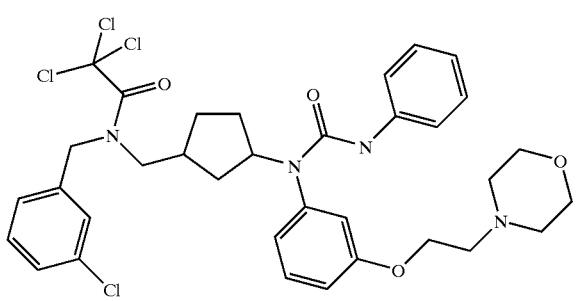

Sodium cyanoborohydride (34 mg, 0.54 mmol) was added to the product prepared in Example 35 (78 mg, 0.18 mmol) and 3-chlorobenzaldehyde (40 μl, 0.36 mmol) in 1% AcOH/MeOH (2 ml). After 6 hours the reaction was acidified with 1N HCl, then neutralized with 2N NaOH and extracted into dichloromethane.

(MH+) 563.

The organic layer was dried over MgSO$_4$, cooled to 0° C. and then treated with trichloroacetyl chloride (20 μl, 0.18 mmol). The final product was isolated by flash chromatography (ethyl acetate).

(MH+) 707

EXAMPLE 38

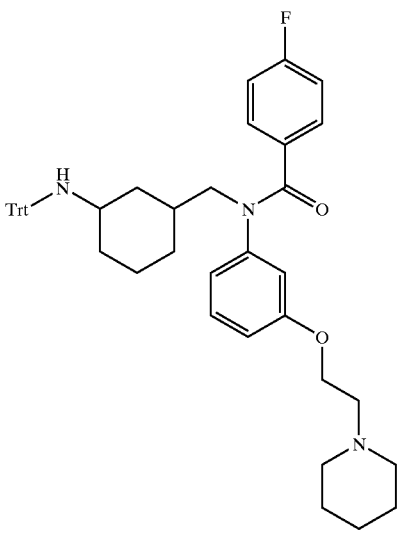

N-trityl-cis-3-aminocyclohexanecarboxylic acid (13.1 g, 34 mmol) was added to a solution of PyBop (17.7 g, 34 mmol) and DIEA (11.8 ml, 68 mmol) in DCM (70 mL) and stirred for 10 minutes. 1-(2-(3-aminophenoxy)ethyl) piperidine (6.8 g, 30.9 mmol) in DCM (30 mL) was added to the reaction mixture over the course of 20 mins. The coupled product was purified by flash chromatography (25% ethyl acetate/1% Et$_3$N/hexane) and evaporated down to yield a white foam.

The foam was dissolved in THF (100 mL), treated with LAH (1.3 g, 34 mmol) and refluxed for 7 hrs. Upon cooling, the reaction mixture was alternately quenched with NaOH and water to yield a granular solid. The heterogenous reaction mixture was then filtered through Celite 545. The reduced product was extracted into ether from water. The combined organic layers were dried over MgSO$_4$ and evaporated to dryness.

The crude product and Et$_3$N (4.7 ml, 34 mmol) were dissolved in DCM (100 mL). 4-fluorobenzoyl chloride (4.0 ml, 34 mmol) of was added dropwise to this solution. After 2 hours the reaction mixture was evaporated onto silica gel and then purified by flash chromatography (20% ethyl acetate/1% Et$_3$N/hexane) to yield the title compound.

EXAMPLE 39

(#239)

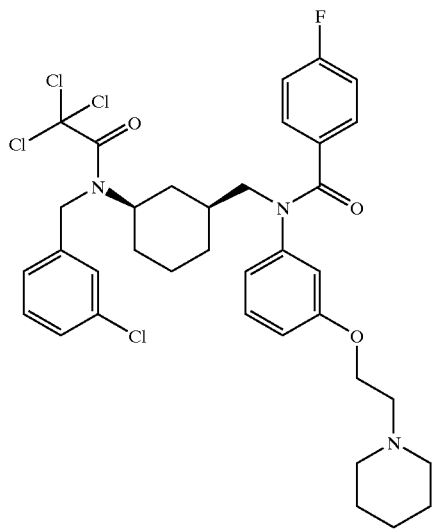

The compound prepared as in Example 38, was dissolved in 20% TFA/1% TES/DCM and stirred for 1 hr. The reaction mixture was evaporated down to dryness. The crude material was partitioned between ether and 1N HCl. The aqueous solution was washed twice with ether, cooled to 0° C. and the pH adjusted to 12 with NaOH. The deprotected amine was extracted into DCM and dried over MgSO$_4$.

Following the procedure as described in Example 8, the deprotected amine, 3-chlorobenzaldehyde and trichloroacetyl chloride were reacted to yield the title compound. The enantiomers were separated using a Chiralpak AD HPLC column.

EXAMPLE 40

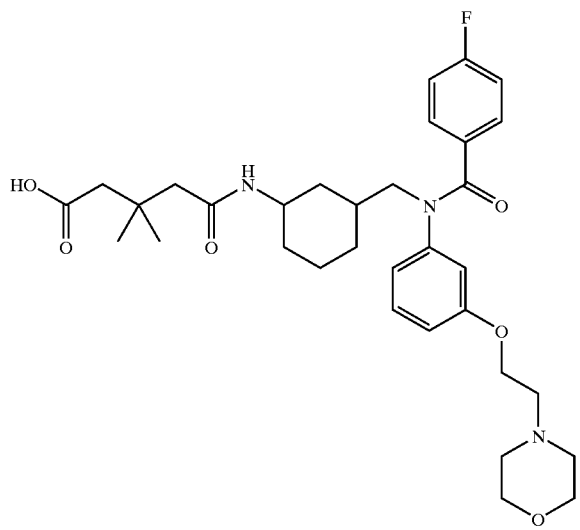

N-(3-(2-(4-morpholino)ethyloxy)phenyl)-N-(cis-3-aminocyclohexyl)methyl-4-fluorophenylcarboxamide (83 mg, 0.18 mmol) and 3,3-dimethylglutaric anhydride (28 mg, 0.20 mmol) were combined and heated at 90° C. in toluene (2 mL) for two hours. The reaction mixture was concentrated in vacuo and purified by semi-prep HPLC (C18 column, acetonitrile/water/0.1% TFA) to yield the title compound.

EXAMPLE 41

(#257)

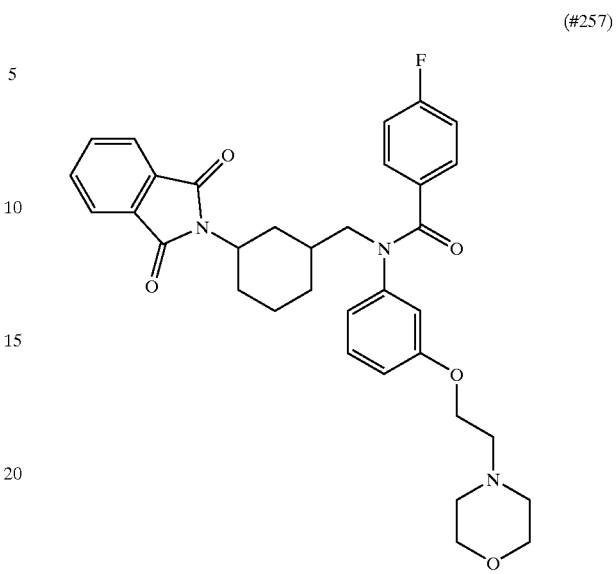

N-(3-(2-(4-morpholino)ethyloxy)phenyl)-N-(cis-3-aminocyclohexyl)methyl-4-fluorophenylcarboxamide (83 mg, 0.18 mmol) and phthalic anhydride (30 mg, 0.20 mmol) were dissolved in toluene (2 mL). The reaction was heated at 90° C. for two hours. To the reaction was then added acetic anhydride (0.2 ml, 2.1 mmol) and the reaction refluxed for an additional 15 hours. The reaction mixture was concentrated in vacuo and purified by semi-prep HPLC (C18 column, acetonitrile/water/0.1% TFA) to yield the title compound as a white solid.

EXAMPLE 42

In Vitro Testing

Motilin Receptor Binding

Rabbit colon was removed, dissected free from the mucosa and serosa, and diced into small pieces. The muscle tissue was homogenized in 10 volumes of 50 mM Tris-Cl, 10 mM MgCl$_2$, 0.1 mg/ml bacitracin, and 0.25 mM Peflabloc, at pH 7.5 in a Polytron (29000 rpm, 4×15 seconds). The homogenate was centrifuged at 1000×g for 15 minutes and the supernatant discarded. The pellet was washed twice before being suspended in homogenizing buffer. The crude homogenate was resuspended through a 23 gauge needle before storing at −80° C. In a total volume of 0.5 ml, the binding assay contained the following components: buffer (50 mM Tris-Cl, 10 mM MgCl$_2$, 1 mM EDTA, 15 mg/ml BSA, 5 mg/ml of pepstatin, leupeptin, aprotinin, and 0.15 mg/ml bacitracin), I$^{125}$ radio-labeled porcine motilin (50000–70000 cpm; specific activity 2000 Ci/mmole), test compound, and membrane protein. After 60 minutes at 30° C., the samples were cooled in ice, centrifuged in the cold at 13000×g for 1 minute. The pellet was washed twice with 1 ml of cold saline, the supernatant was aspirated, and the pellet at the bottom of the tube counted in a gamma counter. Non-specific binding was determined by the inclusion of 1 mM of unlabeled motilin. IC$_{50}$ values were determined from Kaleidograph curves.

EXAMPLE 43

In Vitro Testing
Human Antrum Tissue

Human antrum tissue from Analytical Biological Services (Wilmington, Del.) was prepared as a motilin receptor preparation in the following manner. The muscle tissue was homogenized in 10 volumes of 50 mM Tris-Cl, 10 mM $MgCl_2$, 0.1 mg/ml bacitracin, and 0.25 mM Peflabloc, pH 7.5) in a Polytron (29000 rpm, 4×15 seconds). The homogenate was centrifuged at 1000×g for 15 minutes and the supernatant discarded. The pellet was washed twice before being suspended in homogenizing buffer. The crude homogenate was resuspended through a 23 gauge needle before aliquoting and storing at −80° C. The human cloned receptor was prepared from HEK 293 cells overexpressed with the motilin receptor. Cell pellets were thawed and resuspended in 2–3 volumes of homogenizing buffer (10 mM Tris-Cl, 0.2 mM $MgCl_2$, 5 mM KCl, 5 $\mu$g/ml aprotinin, leupeptin, and pepstatin A, and 50 $\mu$g/ml bacitracin, pH 7.5) and allowed to sit on ice for 15–20 minutes. The suspension was homogenized on ice in a Dounce type homogenizer using 15 strokes. Sucrose and EDTA were added to a final concentration of 0.25M and 1 mM, respectively, and mixed with a few additional strokes. The material was centrifuged at 400×g for 5 minutes, and the supernatant saved. The pellet was re-resuspended twice with 5 ml homogenizing buffer and rehomogenized as before, and the supernatants combined. The supernatant was centrifuged at 100000×g for 1 hour. The pellet is retained and resuspended with 5 ml of homogenizing buffer through a 19 g and 25 g needle. The suspension is aliquoted and stored at −80° C. until used. The binding assay contains the following components (50 mM HEPES, 5 mM $MgCl_2$, and 1 mM EGTA, pH 7.0, 15 mg/ml BSA, 10 $\mu$g/ml aprotinin, leupeptin, and pepstatin A, 0.25 mg/ml bacitracin, and 10 mM benzamidine), 125I-radiolabelled porcine motilin (50000–70000 cpm; specific activity 2000 Ci/mmol), test compound, and membrane protein. After 60 minutes at 30° C., the samples are placed on ice and centrifuged for 1 minute at 13000×g. The pellet is washed twice with 1 ml cold saline, and after removal of the final supernatant, the pellet at the bottom of the tube is counted in a gamma counter. Non-specific binding is measured by the inclusion of 1 $\mu$M unlabelled motilin. $IC_{50}$ values were determined from Kaleidograph curves.

125I-Motilin Binding to Human Antral Stomach Membranes and the Human Cloned Receptor:

| | |
|---|---|
| Human Antrum $IC_{50}$(nM) | 1.0 ± 0.1 |
| Human Cloned Receptor $IC_{50}$(nM) | 3.55 ± 0.05 |

EXAMPLE 44

In Vivo Testing
Rabbit Tissue Bath Procedure

One New Zealand White rabbit (Covance) of either sex was euthanized with an IV injection of Sleepaway. The duodenum was quickly excised, the lumen rinsed with saline to clean, and the tissue placed in cold, aerated (95% $O_2$-5% $CO_2$) Tyrodes buffer (NaCl 136.9 mM, KCl 2.7 mM, $CaCl_2$ 1.8 mM, $MgCl_2$ 1.04 mM, $NaH_2PO_4$ 0.42 mM, $NaHCO_3$ 11.9 mM, Glucose 5.55 mM, pH 7.4). The duodenum, being kept moist at all times, was cleaned of any excess mesenteric tissue, and then cut into 3 cm segments starting at the proximal end. Sixteen tissue segments were usually prepared from each duodenum. These segments were tied on both ends with 3-0 silk suture (Ethicon). One end of the tissue was attached to an S-hook on a custom made glass support rod (Crown Glass Co., Somerville) and the rod plus tissue were placed in a 15 ml isolated tissue bath (Radnoti). The other end of the glass rod was attached to a Grass Force Displacement Transducer FT03. The tissue was maintained in room temperature Tyrodes buffer pH 7.4 and continually gassed with 95% $O_2$— 5% $CO_2$. The tissues were adjusted to 1.0 g resting tension and maintained at that tension throughout the equilibration period. An MI2 Tissue Bath Computer was used to record and analyze data.

The tissues were washed twice during a 30 minute equilibration period and readjusted to 1 g resting tension as necessary. After equilibration the tissues were challenged with 3 $\mu$M Carbachol (Carbamoyicholine Chloride-Sigma). After maximal contraction was attained, the tissues were washed 3 times with Tyrodes. The tissues were allowed a 20 minute resting/equilibration period, during which time they were washed once and readjusted to 1 g resting tension. The tissues were challenged a second time with 3 $\mu$M Carbachol, and this contraction was considered as maximal, or 100% contraction. The tissues were washed 3 times, equilibrated for 10 minutes, washed again and readjusted to 1 g resting tension. Vehicle or test compound in 30% DMSO-50 mM HEPES was added directly to the bath and the tissues were incubated for 20 minutes. Test compounds and vehicle were run in duplicate. The tissues were then challenged with 3 nM Porcine Motilin (Bachem) and when maximum contraction was attained another 3 $\mu$M aliquot of Carbachol was added to see if the test compound inhibited this contraction.

The percent inhibition by test compound of the motilin induced contraction was calculated by first determining the ratio of the vehicle contractions with Motilin compared to the Carbachol contractions. This Tissue Adjustment Factor (TAF) was used to determine the value for the potential uninhibited contraction with Motilin for each tissue. The percent inhibition was then determined by dividing the actual Motilin contraction in treated tissues by the potential uninhibited contraction and subtracting this number from 1. $IC_{50}$ values were determined by graphing results with Kaleidograph graphing program.

Tables 18 and 19 below list molecular weight, % Inhibition and $IC_{50}$ values measured for select compounds of the present invention.

TABLE 18

| | Mol. Wt. * | | Rabbit Colon | | Human Antrum | | Tissues |
|---|---|---|---|---|---|---|---|
| ID | Cal'd | (MH$^+$) | % Inh @ 1 mM | $IC_{50}$ ($\mu$M) | % Inh @ 1 $\mu$M | $IC_{50}$ ($\mu$M) | $IC_{50}$ ($\mu$M) |
| 1 | 621 | 621 | 35 | | | | |
| 2 | 656 | 656 | 9 | | | | |

TABLE 18-continued

| | Mol. Wt. * | | Rabbit Colon | | Human Antrum | | Tissues |
|---|---|---|---|---|---|---|---|
| ID | Cal'd | (MH+) | % Inh @ 1 mM | IC$_{50}$ ($\mu$M) | % Inh @ 1 $\mu$M | IC$_{50}$ ($\mu$M) | IC$_{50}$ ($\mu$M) |
| 3 | 620 | 620 | 35 | | | | |
| 4 | 624 | 624 | 75 | 0.69 | | | |
| 5 | 635 | 635 | 40 | | | | |
| 6 | 634 | 634 | 24 | | | | |
| 7 | 638 | 638 | 42 | | | | |
| 8 | 545 | 545 | 18 | | | | |
| 9 | 580 | 580 | 27 | | | | |
| 10 | 544 | 544 | 29 | | | | |
| 11 | 548 | 548 | 0 | | | | |
| 12 | 594 | 594 | 4 | | | | |
| 13 | 558 | 558 | 21 | | | | |
| 14 | 562 | 562 | 25 | | | | |
| 15 | 531 | 531 | 21 | | | | |
| 16 | 566 | 566 | 21 | | | | |
| 17 | 530 | 530 | 12 | | | | |
| 18 | 534 | 534 | 0 | | | | |
| 19 | 545 | 545 | 5 | | | | |
| 20 | 580 | 580 | 8 | | | | |
| 21 | 544 | 544 | 34 | | | | |
| 22 | 548 | 548 | 23 | | | | |
| 23 | 607 | 607 | 48 | | | | |
| 24 | 642 | 642 | 6 | | | | |
| 25 | 606 | 606 | 23 | | | | |
| 26 | 621 | 621 | 22 | | | | |
| 27 | 656 | 656 | 22 | | | | |
| 28 | 620 | 620 | 13 | | | | |
| 29 | 624 | 624 | 18 | | | | |
| 30 | 559 | 559 | 17 | | | | |
| 31 | 594 | 594 | 39 | | | | |
| 32 | 558 | 558 | 12 | | | | |
| 33 | 562 | 562 | 16 | | | | |
| 34 | 573 | 573 | 7 | | | | |
| 35 | 608 | 608 | 17 | | | | |
| 36 | 572 | 572 | 32 | | | | |
| 37 | 576 | 576 | 11 | | | | |
| 39 | 709 | 707 | 4 | | | | |
| 40 | 662 | 662 | 11 | | | | |
| 41 | 677 | 677 | 58 | | | | |
| 42 | 627 | 627 | 50 | | | | |
| 43 | 675 | 675 | 74 | 0.73 | | | |
| 44 | 697 | 697 | 4 | | | | |
| 45 | 692 | 692 | 67 | 1.16 | | | |
| 46 | 737 | 737 | 32 | | | | |
| 47 | 723 | 721 | 23 | | | | |
| 48 | 637 | 637 | 67 | 0.656 | | | |
| 49 | 817 | 817 | 37 | | | | |
| 50 | 757 | 757 | 32 | | | | |
| 51 | 711 | 711 | 73 | 0.65 | | | |
| 52 | 661 | 661 | 45 | | | | |
| 53 | 709 | 709 | 52 | | | | |
| 54 | 731 | 731 | 42 | | | | |
| 55 | 726 | 726 | 48 | | | | |
| 56 | 771 | 771 | 27 | | | | |
| 57 | 733 | 733 | 15 | | | | |
| 58 | 706 | 705 | 38 | | | | |
| 59 | 757 | 755 | 23 | | | | |
| 60 | 757 | 755 | 65 | 0.66 | | | |
| 61 | 718 | 717 | 55 | | | | |
| 62 | 756 | 755 | 58 | | | | |
| 63 | 723 | 721 | 55 | | | | |
| 64 | 738 | 737 | 32 | | | | |
| 65 | 733 | 732 | 80 | 0.035 | | | 0.027 |
| 66 | 757 | 755 | 39 | | | | |
| 67 | 688 | 687 | 75 | 0.957 | | | |
| 68 | 689 | 688 | 73 | 0.66 | | | |
| 69 | 572 | 572 | 0 | | | | |
| 70 | 547 | 547 | 0 | | | | |
| 71 | 643 | 643 | 43 | | | | |
| 72 | 598 | 597 | 40 | | | | |
| 73 | 549 | 549 | 25 | | | | |
| 74 | 693 | 693 | 29 | | | | |
| 75 | 633 | 633 | 19 | | | | |
| 76 | 587 | 587 | 26 | | | | |
| 77 | 537 | 537 | 19 | | | | |
| 78 | 585 | 585 | 10 | | | | |

TABLE 18-continued

| | Mol. Wt. * | | Rabbit Colon | | Human Antrum | | Tissues |
|---|---|---|---|---|---|---|---|
| ID | Cal'd | (MH⁺) | % Inh @ 1 mM | IC$_{50}$ ($\mu$M) | % Inh @ 1 $\mu$M | IC$_{50}$ ($\mu$M) | IC$_{50}$ ($\mu$M) |
| 79 | 607 | 607 | 39 | | | | |
| 80 | 602 | 602 | 34 | | | | |
| 81 | 647 | 647 | 56 | | | | |
| 82 | 783 | 783 | 0 | | | | |
| 83 | 723 | 723 | 3 | | | | |
| 86 | 697 | 697 | 16 | | | | |
| 90 | 692 | 691 | 95 | 0.49 | | | >0.3 |
| 91 | 601 | 600 | 36 | | | | |
| 92 | 760 | 758 | 80 | | | | |
| 93 | 736 | 735 | 100 | 0.09 | | | 0.0205 |
| 94 | 741 | 740 | 28 | | | | |
| 95 | 726 | 724 | 51 | | | | |
| 96 | 759 | 758 | 71 | 1.68 | | | >.03 |
| 97 | 721 | 720 | 56 | | | | |
| 98 | 760 | 758 | 75 | 0.76 | | | |
| 99 | 760 | 758 | 62 | 0.572 | | | |
| 100 | 709 | 708 | 78 | | | | |
| 101 | 774 | 774 | 59 | | | | |
| 102 | 729 | 729 | 47 | | | | |
| 103 | 734 | 734 | 2 | | | | |
| 104 | 712 | 712 | 30 | | | | |
| 105 | 664 | 664 | 80 | 0.39 | | | 0.03 |
| 106 | 714 | 714 | 69 | 1.05 | | | |
| 107 | 820 | 820 | 29 | | | | |
| 108 | 676 | 676 | 70 | 0.815 | | | |
| 109 | 760 | 760 | 27 | | | | |
| 110 | 718 | 718 | 35 | | | | |
| 111 | 726 | 724 | 72 | 0.88 | | | |
| 112 | 740 | 740 | 70 | 0.48 | | | |
| 113 | 695 | 695 | 51 | | | | |
| 114 | 700 | 700 | 49 | | | | |
| 115 | 678 | 678 | 26 | | | | |
| 116 | 630 | 630 | 61 | 0.772 | | | |
| 117 | 680 | 680 | 17 | | | | |
| 118 | 726 | 726 | 58 | | | | |
| 119 | 786 | 786 | 22 | | | | |
| 120 | 642 | 642 | 69 | 0.954 | | | |
| 121 | 684 | 684 | 37 | | | | |
| 122 | 691 | 690 | 64 | 0.84 | | | |
| 123 | 736 | 736 | 8 | | | | |
| 124 | 640 | 640 | 70 | 0.904 | | | |
| 125 | 665 | 665 | 25 | | | | |
| 128 | 624 | 624 | 75 | 0.23 | | | |
| 129 | 638 | 638 | 90 | 0.058 | | | |
| 130 | 610 | 610 | 8 | | | | |
| 131 | 623 | 622 | 19 | | | | |
| 132 | 658 | 658 | 10 | | | | |
| 133 | 672 | 672 | 6 | | | | |
| 134 | 626 | 626 | 0 | | | | |
| 135 | 694 | 694 | 8 | | | | |
| 136 | 672 | 672 | 43 | | | | |
| 137 | 644 | 644 | 30 | | | | |
| 138 | 582 | 582 | 36 | | | | |
| 139 | 586 | 586 | 13 | | | | |
| 140 | 638 | 638 | 45 | | | | |
| 141 | 672 | 672 | 21 | | | | |
| 142 | 670 | 670 | 17 | | | | |
| 143 | 596 | 596 | 0 | | | | |
| 144 | 638 | 638 | 54 | | | | |
| 145 | 590 | 590 | 35 | | | | |
| 146 | 654 | 654 | 32 | | | | |
| 147 | 688 | 688 | 61 | 0.49 | | | |
| 148 | 622 | 622 | 19 | | | | |
| 149 | 699 | 699 | 27 | | | | |
| 150 | 680 | 680 | 0 | | | | |
| 151 | 713 | 712 | 1 | | | | |
| 152 | 700 | 700 | 0 | | | | |
| 153 | 636 | 636 | 89 | 0.081 | | | 0.03 |
| 154 | 692 | 692 | 62 | 0.41 | | | |
| 155 | 676 | 676 | 34 | | | | |
| 156 | 554 | 554 | 18 | | | | |
| 157 | 642 | 642 | 16 | | | | |
| 158 | 601 | 600 | 37 | | | | |
| 159 | 652 | 652 | 83 | 0.275 | | | |
| 160 | 652 | 652 | 61 | 0.96 | | | |

TABLE 18-continued

| | Mol. Wt. * | | Rabbit Colon | | Human Antrum | | Tissues |
| | Cal'd | (MH⁺) | % Inh @ 1 mM | IC$_{50}$ ($\mu$M) | % Inh @ 1 $\mu$M | IC$_{50}$ ($\mu$M) | IC$_{50}$ ($\mu$M) |
|---|---|---|---|---|---|---|---|
| 161 | 664 | 664 | 22 | | | | |
| 162 | 672 | 672 | 85 | 0.178 | | | 0.021 |
| 163 | 658 | 658 | 85 | 0.174 | | | 0.019 |
| 164 | 624 | 624 | 84 | 0.194 | | | 0.048 |
| 165 | 624 | 624 | 63 | 0.55 | | | |
| 166 | 636 | 636 | 23 | | | | |
| 167 | 674 | 674 | 42 | | | | |
| 168 | 640 | 640 | 36 | | | | |
| 169 | 638 | 638 | 97 | 0.046 | | | 0.24 |
| 170 | 638 | 638 | 81 | 0.163 | | | 0.185 |
| 171 | 650 | 650 | 63 | 0.462 | | | 0.23 |
| 172 | 688 | 688 | 40 | | | | |
| 173 | 654 | 654 | 84 | 0.29 | | | 0.28 |
| 174 | 692 | 691 | 0 | | | | |
| 175 | 525 | 525 | 0 | | | | |
| 176 | 636 | 636 | 32 | | | | |
| 177 | 640 | 640 | 52 | >1.0 | | | |
| 178 | 624 | 624 | 100 | 0.07 | | | 0.015 |
| 179 | 637 | 637 | 85 | 0.24 | | | 0.023 |
| 180 | 622 | 622 | 99 | 0.014 | | | 0.011 |
| 181 | 596 | 596 | 100 | 0.093 | | | 0.012 |
| 182 | 636 | 636 | 94 | 0.022 | | | 0.053 |
| 183 | 661 | 661 | 2 | | | | |
| 184 | 711 | 711 | 6 | | | | |
| 185 | 671 | 671 | 0 | | | | |
| 186 | 722 | 722 | 0 | | | | |
| 187 | 610 | 610 | 100 | 0.229 | | | |
| 188 | 650 | 650 | 100 | 0.247 | | | 0.092 |
| 189 | 652 | 652 | 70 | 0.3 | | | |
| 190 | 666 | 666 | 99 | 0.2 | | | 0.067 |
| 191 | 622 | 622 | 27 | | | | |
| 192 | 638 | 638 | 15 | | | | |
| 193 | 650 | 650 | 7 | | | | |
| 194 | 596 | 596 | 23 | | | | |
| 195 | 624 | 624 | 62 | | | | |
| 196 | 636 | 636 | 100 | 0.006 | | | 0.004 |
| 197 | 667 | 667 | 85 | 0.009 | | | 0.0076 |
| 198 | 672 | 672 | 100 | 0.107 | | | |
| 199 | 691 | 690 | 91 | 0.1 | | | |
| 200 | 690 | 690 | 92 | 0.041 | | | |
| 201 | 657 | 657 | 93 | 0.057 | | | 0.0168 |
| 202 | 691 | 690 | 100 | 0.33 | | | 0.23 |
| 203 | 649 | 649 | 98 | 0.24 | | | |
| 204 | 662 | 662 | 89 | 0.029 | | | 0.003 |
| 205 | 683 | 683 | 76 | 0.1 | | | |
| 206 | 688 | 688 | 60 | 0.77 | | | |
| 207 | 636 | 636 | 87 | 0.064 | | | |
| 208 | 734 | 733 | 91 | 0.009 | | | 0.048 |
| 209 | 724 | 722 | 84 | 0.059 | | | 0.021 |
| 210 | 689 | 688 | 90 | 0.086 | | | 0.024 |
| 211 | 720 | 719 | 100 | 0.014 | | | 0.072 |
| 212 | 710 | 708 | 89 | 0.058 | | | 0.036 |
| 213 | 675 | 674 | 84 | 0.058 | | | 0.027 |
| 214 | 614 | 614 | 95 | 0.029 | | | 0.024 |
| 215 | 680 | 680 | 100 | 0.084 | | | |
| 216 | 600 | 600 | | | 100 | | |
| 217 | 634 | 634 | | | 98 | | |
| 218 | 661 | 660 | | | 98 | 0.024 | 0.035 |
| 219 | 706 | 705 | | | 98 | 0.0076 | |
| 220 | 636 | 636 | | | 92 | 0.042 | |
| 221 | 598 | 598 | | | 94 | | |
| 223 | 707 | 705 | 100 | 0.041 | | | |
| 224 | 672 | 671 | 98 | 0.039 | | | |
| 225 | 611 | 611 | 93 | 0.021 | | | |
| 226 | 648 | 648 | | | 100 | 0.032 | 0.009 |
| 227 | 683 | 682 | | | 100 | 0.025 | |
| 228 | 650 | 650 | | | 100 | 0.025 | |
| 229 | 614 | 614 | 100 | 0.01 | | | |
| 230 | 614 | 614 | 100 | 0.072 | | | |

TABLE 18-continued

| | Mol. Wt. * | | Rabbit Colon | | Human Antrum | | Tissues |
|---|---|---|---|---|---|---|---|
| ID | Cal'd | (MH+) | % Inh @ 1 mM | IC$_{50}$ ($\mu$M) | % Inh @ 1 $\mu$M | IC$_{50}$ ($\mu$M) | IC$_{50}$ ($\mu$M) |
| 231 | 661 | 660 | | | 88 | 0.13 | |
| 232 | 698 | 698 | 62 | | | | |
| 233 | 650 | 650 | 89 | 0.17 | | | |
| 234 | 652 | 652 | 86 | 0.218 | | | |
| 235 | 662 | | 61 | | | | |
| 236 | 724 | | 53 | | | | |
| 237 | 662 | | 96 | 0.168 | | | |
| 238 | 724 | | 98 | 0.097 | | | |
| 239 | 724 | | | 0.073 | | | |
| 240 | 724 | | | >0.70 | | | |
| 241 | 728 | | 14 | | | | |
| 242 | 704 | | 36 | | | | |
| 243 | 728 | | 35 | | | | |
| 244 | 698 | | 42 | | | | |
| 245 | 758 | | 40 | | | | |
| 246 | 678 | | 73 | | | | |
| 247 | 726 | | 41 | | | | |
| 248 | 704 | | 86 | 0.760 | | | |
| 249 | 716 | | 22 | | | | |
| 250 | 642 | | 0 | | | | |
| 251 | 604 | | 0 | | | | |
| 252 | 636 | | 15 | | | | |
| 253 | 600 | | 30 | | | | |
| 254 | 606 | | 25 | | | | |
| 255 | 655 | | 22 | | | | |
| 256 | 600 | | 27 | | | | |
| 257 | 586 | | 0 | | | | |
| 258 | 580 | | 34 | | | | |
| 259 | 665 | | 17 | | | | |
| 260 | 644 | | 30 | | | | |
| 261 | 654 | | 0 | | | | |
| 262 | 550 | | 18 | | | | |
| 263 | 655 | | 11 | | | | |
| 264 | 570 | | 6 | | | | |
| 265 | 638 | | 67 | | | | |
| 266 | 598 | | 5 | | | | |
| 267 | 624 | | 21 | | | | |
| 268 | 598 | | 17 | | | | |

* For compounds containing chlorine, listed Mol. Wt. values are provided for the most abundant isotope.

TABLE 19

| ID | Cal'd Mol. Wt. | MW (MH+) | % Inh @ 1 mM (Rabbit colon) | % Inh @ 1 mM (Human antrum) |
|---|---|---|---|---|
| 38 | 577.4 | 576 | 22 | |
| 84 | 542.7 | 543 | 12 | |
| 85 | 577.2 | 577 | 28 | |
| 87 | 611.6 | 611 | 22 | |
| 88 | 592.8 | 593 | 0 | |
| 89 | 561.7 | 562 | 3 | |
| 222 | 619.8 | 620 | 83 | 83 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:
1. A compound of formula (I):

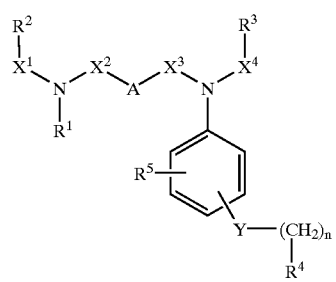

wherein:
R$^1$ is selected from the group consisting of hydrogen, aryl, aralkyl, heterocyclyl, diarylalkyl, heterocyclyl-alkyl, and lower alkyl; wherein the alkyl, aryl or heterocyclyl moieties in the foregoing groups may be substituted with one or more substituents independently selected from halogen, hydroxy, nitro, carboxy, cyano, amino, dialkylamino, lower alkoxy, lower alkyl, tri-halomethyl, alkylamino, carboxy and alkoxycarbonyl;
R$^2$ is selected from the group consisting of aryl, aralkyl, cycloalkyl, cycloalkyl-alkyl heterocyclyl, heterocyclyl-alkyl, diarylalkyl, aminoalkyl, tri-halomethyl, arylamino and lower alkyl; wherein the alkyl, aryl, heterocyclyl-alkyl, heterocyclyl, or amino moieties in the foregoing groups may be substituted with one or more substituents independently selected from halogen, hydroxy, nitro, cyano, amino, dialkylamino, lower alkoxy, lower alkyl, tri-halomethyl, alkylamino, phenyl, carboxy, carboxyalkyl and alkoxycarbonyl;

$X^1$, $X^2$, $X^3$ and $X^4$ are independently absent or selected from the group consisting of CO and $SO_2$; provided that at least one of $X^1$ or $X^2$ and at least one of $X^3$ or $X^4$ is CO or $SO_2$;

alternatively $R^1$, $R^2$ and $X^1$ can be taken together (with the amine nitrogen) to form a monocyclic or fused bicyclic or tricyclic secondary amine ring structure; wherein the monocyclic or fused bicyclic or tricyclic secondary amine ring structure may be optionally substituted with one or more substituents independently selected from halogen, oxo, nitro, cyano, amino, alkylamino, dialkylamino, trialkylamino, lower alkoxy, lower alkyl, tri-halomethyl, carboxy, acetyloxy, alkoxycarbonyl, aryl, aralkyl and heterocyclyl;

A is selected from the group consisting of lower alkyl, lower alkenyl, cycloalkyl, cycloalkyl-alkyl, alkyl-cycloalkyl, cycloalkenyl, cycloalkenyl-alkyl, alkyl-cycloalkenyl, alkyl-cycloalkyl-alkyl; alkyl-aryl-alkyl, alkyl-aryl, aryl-alkyl and phenyl; where, in each case, the A group may optionally be substituted with one or more substituents selected from $R^7$;

where $R^7$ is selected from alkyl, tri-halomethyl, cycloalkyl, aryl, aralkyl, heterocyclyl, heterocyclyl-alkyl, diarylalkyl, aminoalkyl, or arylamino; wherein the alkyl, aryl, heterocyclyl-alkyl, heterocyclyl, or amino moieties in the foregoing groups may be substituted with one or more substituents independently selected from halogen, hydroxy, nitro, cyano, amino, dialkylamino, lower alkoxy, lower alkyl, tri-halomethyl, alkylamino, phenyl, carboxy and alkoxycarbonyl;

provided that A is not -1,3-cyclopentyl-1-ene-alkyl;

$R^3$ is selected from the group consisting of hydrogen, aryl, heterocyclyl, aralkyl, diarylalkyl, heterocyclo-alkyl, tri-halomethyl, alkylamino, arylamino and lower alkyl; wherein the aryl, heterocyclyl, aralkyl, diarylalkyl, heterocyclyl-alkyl, alkylamino, arylamino or lower alkyl group may be substituted with one or more substituents independently selected from halogen, nitro, cyano, amino, dialkylamino, lower alkoxy, lower alkyl, tri-halomethyl, carboxy and alkoxycarbonyl;

Y is selected from the group consisting of —O—, —NH—, —S— and —$SO_2$—;

n is an integer from 0 to 5;

$R^4$ is selected from the group consisting of hydrogen, amino, alkylamino, dialkylamino, N-alkyl-N-aralkyl-amino, trialkylamino, dialkylaminoalkoxyalkyl, heterocyclyl, heterocyclyl-alkyl, oxo-substituted heterocyclyl and lower alkyl substituted heterocyclyl;

$R^5$ is selected from the group consisting of hydrogen, halogen, nitro, cyano, amino, alkylamino, dialkylamino, trialkylamino, lower alkoxy, lower alkyl, tri-halomethyl, carboxy and alkoxycarbonyl;

and the pharmaceutically acceptable salts and esters thereof.

2. A compound of claim 1 wherein:

$R^1$ is selected from the group consisting of hydrogen, aralkyl, heterocyclyl and heterocyclyl-alkyl; where the aralkyl, heterocyclyl or heterocyclyl-alkyl may be substituted with one or more substituents independently selected from halogen, lower alkyl, lower alkoxy, tri-halomethyl, hydroxy or nitro;

$R^2$ is selected from the group consisting of alkyl, tri-halomethyl, aryl, aralkyl, arylamino, biphenyl, cycloalkyl, cycloalkyl-alkyl, heterocyclyl and heterocyclyl-alkyl; where the aryl, aralkyl or heterocyclyl group may be substituted with one or more substituents independently selected from halogen, lower alkoxy, nitro, carboxy, carboxyalkyl, hydroxy, phenyl, diphenylmethyl, tri-halomethyl or trihaloalkylacetyl;

$X^1$, $X^2$, $X^3$ and $X^4$ are independently absent or selected from the group consisting of CO and $SO_2$; such that at least one of $X^1$ or $X^2$ and at least one of $X^3$ or $X^4$ is CO or $SO_2$;

A is selected from the group consisting of lower alkyl, alkyl-cycloalkyl, cycloalkyl-alkyl, -cycloalkyl, -cycloalkenyl-, cycloalkenyl-alkyl- and -aryl-alkyl-; where the alkyl moiety in the foregoing groups may be substituted with one or more substituents independently selected from aralkyl and cycloalkyl;

provided that A is not -1,3-cyclopentyl-1-ene-alkyl;

$R^3$ is selected from the group consisting of hydrogen, aryl, aralkyl and arylamino; where the aryl or aralkyl group may be substituted with one or more substituents independently selected from halogen, lower alkyl, lower alkoxy or tri-halomethyl;

Y is —O—;

n is an integer from 0 to 3;

$R^4$ is selected from the group consisting of hydrogen, heterocyclyl, oxo-substituted heterocyclyl, lower alkyl substituted heterocyclyl, di(lower alkyl)amino, N-lower alkyl-N-aralkyl-amino and di(lower alkyl) amino alkoxy alkyl;

$R^5$ is selected from the group consisting of hydrogen and lower alkyl;

and the pharmaceutically acceptable salts and esters thereof.

3. A compound of claim 1 wherein:

$R^1$ is selected from the group consisting of hydrogen, phenyl($C_1$–$C_6$)alkyl-, naphthyl($C_{1-6}$)alkyl-, and heterocyclyl($C_1$–$C_6$)alkyl- where the heterocyclyl group is selected from pyridyl and where the phenyl, naphthyl or heterocyclyl moiety is optionally substituted with one to three substituents selected from halogen, lower alkyl, lower alkoxy, tri-halomethyl, hydroxy and nitro;

$R^2$ is selected from the group consisting of ($C_1$–$C_6$) branched or unbranched alkyl, phenyl, phenyl($C_1$–$C_6$) alkyl-, tri-halomethyl, phenylamino-, biphenyl, diphenyl($C_1$–$C_6$)alkyl-, $C_{5-8}$cycloalkyl, $C_{5-8}$cycloalkyl ($C_{1-6}$)alkyl, heterocyclyl and heterocyclyl($C_1$–$C_6$) alkyl-wherein the heterocyclyl moiety is selected from naphthyl, furyl, pyridyl, pyrrolidinyl and thienyl and wherein the phenyl or heterocyclyl group may be substituted with one to four substituents selected from halogen, lower alkoxy, nitro, carboxy, carboxy($C_{1-4}$) alkyl, hydroxy, phenyl, diphenylmethyl, trihalomethyl and trihaloalkylacetyl;

$X^1$, $X^2$, $X^3$ and $X^4$ are independently absent or selected from the group consisting of CO and $SO_2$; such that at least one of $X^1$ or $X^2$ and at least one of $X^3$ or $X^4$ is CO or $SO_2$;

A is selected from the group consisting of lower alkyl, loweralkyl-cycloalkyl, cycloalkyl-loweralkyl, -cycloalkyl, -cycloalkenyl-, cycloalkenyl-loweralkyl- and -phenyl-loweralkyl- and -benzyl-loweralkyl, provided that A is not -1,3-cyclopentyl-1-ene-alkyl;

$R^3$ is selected from the group consisting of hydrogen, phenyl, benzyl and phenylamino-; where the phenyl or benzyl moieties may be substituted with one to three substituents selected from halogen, lower alkyl, lower alkoxy and trihalomethyl;

Y is —O—;

n is an integer from 0 to 3;

$R^4$ is selected from the group consisting of hydrogen, heterocyclyl, oxo substituted heterocyclyl, lower alkyl substituted heterocyclyl, di(loweralkyl) amino, N-lower alkyl-N—

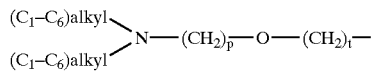

aralkyl-amino and a moiety of the formula:

where p and t are integers from 1–6;

$R^5$ is selected from hydrogen and lower alkyl;

and the pharmaceutically acceptable salts and esters thereof.

4. A compound as in claim 1 wherein $R^1$ is selected from the group consisting of hydrogen, benzyl, 2-(phenyl)ethyl, 4-methylbenzyl, 3-methoxybenzyl, 3-nitrobenzyl, 3-chlorobenzyl, 3-fluorobenzyl, 4-chlorobenzyl, 2,3-dichlorobenzyl, 3,4-dichlorobenzyl, 3,5-dichlorobenzyl, 3,4-difluorobenzyl, 3-trifluoromethylbenzyl, 1-naphthyl-methyl, 2-pyridyl-methyl and 4-(1-hydroxy)pyridyl;

$R^2$ is selected from the group consisting of methyl, ethyl, t-butyl, 2,2-dimethylpropyl, benzyl, 2-(phenyl)ethyl, 3-(phenyl)propyl, 1-(phenyl)propyl, 3-carboxy-n-propyl, 3-carboxy-3-methyl-n-butyl, 2,2-dimethyl-3-carboxy-n-propyl, trichloromethyl, trifluoromethyl, 2-naphthyl, phenylamino, 3-methoxyphenyl, 3-hydroxyphenyl, 4-fluorobenzyl, 3-carboxybenzyl, 3-methoxybenzyl, 4-methoxybenzyl, 3,4-dimethoxybenzyl, 2-(4-methoxyphenyl)ethyl, 4-fluorophenyl, 2-(4-chlorophenyl)ethyl, 3-nitrophenyl, 3,5-di(trifluoromethyl)phenyl, 3,3,3-trifluoropropan-2-oyl, diphenylmethyl, 4-biphenyl, 3-carboxymethyl-1,2,2-trimethyl-cyclopenlyl, cyclopentylethyl, (1-carboxymethyl-cyclopentyl)-methyl, 2-furyl, 2-pyridyl-(2-ethyl), 1-pyrrolidinyl-(2-ethyl), 2-thienylmethyl and 2-thienylethyl;

$X^1$, $X^2$, $X^3$ and $X^4$ are independently absent or selected from the group consisting of CO, and $SO_2$; such that one of $X^1$ or $X^2$ and one of $X^3$ or $X^4$ is CO or $SO_2$;

A is selected from the group consisting of 1,2-ethyl, 1,3-propyl, 1,4-butyl, 2-methyl-1,3-propyl, 1,1,-dimethyl-(1,3-propyl), 2-cyclopentyl-1,3-n-propyl, 1S,3R-cyclopentyl-methyl, 1,2-cyclopent-1-enyl, 1,4-cyclopentyl-2-ene-methyl, methyl-1,3-cyclohexyl, 1,2-cyclohexyl-methyl-, 1,3-cyclohexyl-methyl-, 1S,3R-cyclohexyl-methyl-, 1R,3S-cyclohexyl-methyl-, 1,4-cyclohexyl-methyl-, 1,2-cyclohex-4-enyl, 1,3-phenyl-methyl and 1-benzyl-methyl-;

$R^3$ is selected from the group consisting of hydrogen, phenylamino, 4-methylphenyl, 4-fluorophenyl, 2-fluorobenzyl, 3-fluorobenzyl, 4-fluorobenzyl, 4-chlorobenzyl, 4-methoxybenzyl and 4-trifluoromethylbenzyl;

Y is selected from the group consisting of -3-O— and -4-O—;

n is an integer selected from 0, 2 or 3;

$R^4$ is selected from the group consisting of hydrogen, 4-morpholinyl, 1-pyrrolidinyl, 2-oxo-pyrrolidin-1-yl, 2-(1-methylpyrrolidinyl), 1-piperazinyl, 1-piperidinyl, di(methyl)aminoethyloxyethyl, N-methyl-N-benzyl-amino, di(methyl)amino and diethylamino;

$R^5$ is selected from the group consisting of hydrogen, 2-methyl and 6-methyl;

and the pharmaceutically acceptable salts and esters thereof.

5. A compound as in claim 1 wherein $R^1$ is selected from the group consisting of benzyl, 2-(phenyl)ethyl, 3-nitrobenzyl, 3-chlorobenzyl, 3,4-dichlorobenzyl, 3,4-difluorobenzyl, 3,5-dichlorobenzyl, 3-trifluoromethylbenzyl and 2-pyridyl-methyl;

$R^2$ is selected from the group consisting of t-butyl, 2-(phenyl)ethyl, trichloromethyl, 3-carboxybenzyl, 3-methoxybenzyl, 2-(4-methoxyphenyl)ethyl, 2-(4-chlorophenyl)ethyl, diphenylmethyl, 2-(2-pyridyl) ethyl, 2-(1-pyrrolidinyl)ethyl and 2-(2-thienyl)ethyl;

$X^1$, $X^2$, $X^3$ and $X^4$ are independently absent or CO; such that one of $X^1$ or $X^2$ and one of $X^3$ or $X^4$ is CO;

A is selected from the group consisting of 1,2-ethyl, 1,3-propyl, 2-methyl-1,3-propyl, 1,1,-dimethyl-(1,3-propyl), 2-cyclopentyl-1,3-n-propyl, 1S,3R-cyclopentyl-methyl, 1,3-cyclohexyl-methyl, 1S,3R-cyclohexyl-methyl- and 1R,3S-cyclohexyl-methyl-;

$R^3$ is selected from the group consisting of phenylamino, 4-fluorophenyl, 3-fluorobenzyl, 2-fluorobenzyl, 4-fluorobenzyl, 4-chlorobenzyl, 4-methoxybenzyl and 4-trifluoromethylbenzyl;

Y is selected from the group consisting of -3-O— and -4-O—;

n is an integer selected from 2 or 3;

$R^4$ is selected from the group consisting of hydrogen, 4-morpholinyl, 1-pyrrolidinyl, 1-piperazinyl, 1-piperidinyl, di(methyl)amino and di(ethyl)amino;

$R^5$ is selected from the group consisting of hydrogen, 2-methyl and 6-methyl;

and the pharmaceutically acceptable salts and esters thereof.

6. A compound as in claim 1 wherein $R^1$ is selected from the group consisting of benzyl, 2-(phenyl)ethyl, 3-nitrobenzyl, 3-chlorobenzyl, 3,4-dichlorobenzyl, 3,4-difluorobenzyl, 3,5-dichlorobenzyl and 3-trifluoromethylbenzyl;

$R^2$ is selected from the group consisting of t-butyl, 2-(phenyl)ethyl, trichloromethyl, 3-carboxybenzyl, 3-methoxybenzyl, 2-(2-pyridyl)ethyl and 2-(2-thienyl) ethyl;

$X^1$, $X^2$, $X^3$ and $X^4$ are independently absent or CO; such that one of $X^1$ or $X^2$ and one of $X^3$ or $X^4$ is CO;

A is selected from the group consisting of 1,3-propyl, 1S,3R-cyclopentyl-methyl, 1,3-cyclohexyl-methyl-, 1S,3R-cyclohexyl-methyl- and 1R,3S-cyclohexyl-methyl-;

$R^3$ is selected from the group consisting of phenylamino, 4-fluorophenyl, 3-fluorobenzyl and 4-fluorobenzyl;

Y is -3-O—;

n is 2;

R$^4$ is selected from the group consisting of hydrogen, 4-morpholinyl, 1-pyrrolidinyl, 1-piperidinyl and di(methyl)amino;

R$^5$ is selected from the group consisting of hydrogen, 2-methyl and 6-methyl;

and the pharmaceutically acceptable salts and esters thereof.

7. A compound as in claim 1 wherein

R$^1$ is selected from the group consisting of benzyl, 3-nitrobenzyl, 3-chlorobenzyl, 3,4-dichlorobenzyl, 3,4-difluorobenzyl and 3-trifluoromethylbenzyl;

R$^2$ is selected from the group consisting of t-butyl, 2-(phenyl)ethyl, trichloromethyl, 2-(2-pyridyl)ethyl and 2-(2-thienyl)ethyl;

X$^1$, X$^2$, X$^3$ and X$^4$ are independently absent or CO; such that one of X$^1$ or X$^2$ and one of X$^3$ or X$^4$ is CO;

A is selected from the group consisting of 1,3-propyl, 1S,3R-cyclopentyl-methyl, 1,3-cyclohexyl-methyl-, 1S,3R-cyclohexyl-methyl- and 1R,3S-cyclohexyl-methyl-;

R$^3$ is selected from the group consisting of phenylamino, 4-fluorophenyl, 3-fluorobenzyl and 4-fluorobenzyl;

Y is -3-O—;

n is 2;

R$^4$ is selected from the group consisting of hydrogen, 4-morpholinyl, 1-pyrrolidinyl and 1-piperidinyl;

R$^5$ is selected from the group consisting of hydrogen and 2-methyl;

and the pharmaceutically acceptable salts and esters thereof.

8. A compound as in claim 7 wherein R$^1$ is 3-chlorobenzyl, R$^2$ is trichloromethyl, X$^1$ is CO, X$^2$ is absent, X$^3$ is absent, X$^4$ is CO, A is 1S,3R-cyclohexyl-methyl-, R$^3$ is 4-fluorophenyl, Y is -3-O—, n is 2, R$^4$ is 1-piperidinyl, R$^5$ is hydrogen and the pharmaceutically acceptable salts and esters thereof.

9. A compound as in claim 7 wherein R$^1$ is 3-chlorobenzyl, R$^2$ is trichloromethyl, X$^1$ is CO, X$^2$ is absent, X$^3$ is absent, X$^4$ is CO, A is 1R,3S-cyclohexyl-methyl-, R$^3$ is 4-fluorophenyl, Y is -3-O—, n is 2, R$^4$ is 1-piperidinyl, R$^5$ is hydrogen and the pharmaceutically acceptable salts and esters thereof.

10. A compound as in claim 1 wherein:

R$^1$, R$^2$ and X$^1$ are taken together (with the amine nitrogen) to form an optionally substituted, monocyclic, bicyclic or tricyclic secondary amine ring structure selected from the group consisting of 1-phenyl-1,2,3,4-tetrahydroisoquinolinyl, 4-[(4-chlorophenyl)phenylmethyl]piperazin-1-yl and 2-[1-benzyl-6-methoxy-1,2,3,4-tetrahydro]-naphthyl, 2-[1-benzyl-6-methoxy-1,2,3,4-tetrahydro]-naphthyl, isoindole-1,3-dione, 5-t-butyl-isoindole-1,3-dione, 5-fluoro-isoindole-1,3-dione, 5-methyl-isoindole-1,3-dione, 5,6-dichloro-isoindole-1,3-dione, 4,7-dichloro-isoindole-1,3-dione, 5-bromo-isoindole-1,3-dione, 5-acetyloxy-isoindole-1,3-dione, benzo[e]isoindole-1,3-dione, 8-fluorobenzo[e]isoindole-1,3-dione, 4,4-dimethyl-piperidine-2,6-dione, 3-aza-bicyclo[3.1.0]hexane-2,6-dione and 8-aza-siro[4.5]decane-7,9-dione; and the pharmaceutically acceptable salts and esters thereof.

11. A compound as in claim 8 wherein:

R$^1$, R$^2$ and X$^1$ are taken together (with the amine nitrogen) to form 1-phenyl-1,2,3,4-tetrahydroisoquinolinyl, X$^2$ is C(O), A is 1,3-propyl, X$^3$ is C(O), R$^3$ is 4-fluorobenzyl, Y is 3-O—, n is 2 and R$^4$ is 4-morpholinyl.

12. A compound as in claim 8 wherein:

R$^1$, R$^2$ and X$^1$ are taken together (with the amine nitrogen) to form 4-[(4-chlorophenyl)phenylmethyl] piperazin-1-yl, X$^2$ is C(O), A is 1,3-n-propyl, X$^3$ is absent, R$^3$ is 4-fluorophenyl, X$^4$ is C(O), Y is 3-O—, n is 2 and R$^4$ is 4-morpholinyl.

13. A compound as in claim 8 wherein:

R$^1$, R$^2$ and X$^1$ are taken together (with the amine nitrogen) to form 2-[1-benzyl-6-methoxy-1,2,3,4-tetrahydro]-naphthyl, X$^2$ is C(O), A is 1,3-n-propyl, X$^3$ is absent, R$^3$ is 4-fluorophenyl, X$^4$ is C(O), Y is 3-O—, n is 2 and R$^4$ is 4-morpholinyl.

14. A compound as in claim 1 wherein R$^1$ is benzyl, R$^2$ is benzyl, A is 1,3-cyclohexyl-methyl, X$^1$ is absent, X$^2$ is absent, X$^3$ is absent, X$^4$ is C(O), R$^3$ is 4-fluorophenyl, Y is 3-O—, n is 2, R$^4$ is 1-pyrrolidinyl and R$^5$ is hydrogen and pharmaceutically acceptable salts and esters thereof.

15. A pharmaceutical composition comprising a pharmaceutically acceptable carrier and a compound of claim 1.

16. A pharmaceutical composition made by mixing a compound of claim 1 and a pharmaceutically acceptable carrier.

17. A process for making a pharmaceutical composition comprising mixing a compound of claim 1 and a pharmaceutically acceptable carrier.

* * * * *